(12) United States Patent
Alihodzic et al.

(10) Patent No.: US 7,547,679 B2
(45) Date of Patent: Jun. 16, 2009

(54) ETHER LINKED MACROLIDES USEFUL FOR THE TREATMENT OF MICROBIAL INFECTIONS

(75) Inventors: Sulejman Alihodzic, Zagreb (HR); Drazen Pavlovic, Zagreb (HR); Eric Hunt, Harlow (GB); Andrew Keith Forrest, Harlow (GB); Ivana Palej, Zagreb (HR); Samra Kapic, Zagreb (HR); Vlado Stimac, Velika Gorica (HR)

(73) Assignees: GlaxoSmithKline istrazivacki center Zagreb d.o.o, Zagres (HR); Glaxo Group Limited, Greenford, Middlesex (GB)

( * ) Notice: Subject to any disclaimer, the term of this patent is extended or adjusted under 35 U.S.C. 154(b) by 362 days.

(21) Appl. No.: 11/431,696

(22) Filed: May 9, 2006

(65) Prior Publication Data

US 2006/0258600 A1 Nov. 16, 2006

Related U.S. Application Data

(60) Provisional application No. 60/679,779, filed on May 10, 2005.

(51) Int. Cl.
*A61K 31/70* (2006.01)
*C07H 17/08* (2006.01)

(52) U.S. Cl. .............................. 514/29; 536/7.2; 536/7.4

(58) Field of Classification Search ........................ None
See application file for complete search history.

(56) References Cited

U.S. PATENT DOCUMENTS

| 4,990,602 | A | 2/1991 | Morimoto et al. |
| 6,262,030 | B1 | 7/2001 | Wu et al. |
| 6,624,159 | B2 | 9/2003 | Anderson et al. |

FOREIGN PATENT DOCUMENTS

| EP | 248 279 | 12/1987 |
| EP | 307 177 | 3/1989 |
| EP | 503 932 | 9/1992 |
| EP | 507 595 | 10/1992 |
| EP | 508 699 | 10/1992 |
| EP | 284 203 | 9/1998 |
| EP | 0 895 999 | 10/1999 |
| EP | 1 167 375 | 1/2002 |
| WO | WO 97/42204 | 11/1997 |
| WO | WO 99/51616 | 10/1999 |
| WO | WO 00/63223 | 10/2000 |
| WO | WO 00/78773 | 12/2000 |
| WO | WO 02/00196 | 1/2002 |
| WO | WO 02/50091 | 6/2002 |
| WO | WO 02/50092 | 6/2002 |
| WO | WO 03/004228 | 5/2003 |
| WO | WO 2004/039822 | 5/2004 |
| WO | WO 2004/101585 | 11/2004 |
| WO | WO-2004/101586 | 11/2004 |
| WO | WO 2004/101587 | 11/2004 |
| WO | WO 2004/101588 | 11/2004 |
| WO | WO 2004/101589 | 11/2004 |
| WO | WO 2005/108412 | 11/2005 |
| WO | WO 2005/108413 | 11/2005 |

OTHER PUBLICATIONS

Clark, R.F., et al. 2000. Synthesis and Antibacterial Activity of Novel 6-*O*-Substituted Erythromycin A Derivatives, *Bioorganic & Medicinal Chemistry Letters* 10: 815-819.

Chung, S.J., et al. 1997. Synthesis and Evaluation of 3-Fluoro-2-piperazinyl-5,8,13-trihydro-5-oxoquino[1,2-α][3,1]benzoxazine-6-carboxylic Acids as Potential Antibacterial Agents. *Arch. Pharm. Pharm. Med. Chem.* 330: 63-66.

Cecchetti, V., et al. 1995. 6-Aminoquinolones: A New Class of Quinolone Antibacterials? *J. Med. Chem.* 38: 973-982.

Kobrehel, G., et al. 1992. Synthesis and Antibacterial Activity of *O*-Methylazithromycin Derivatives, *J. Antibiotics* 45: 527-532.

Debono, M., et al. 1989. Synthesis and Antimicrobial Evaluation of 20-Deoxo-20-(3,5-Dimethylpiperidin-1-yl)Mesmycosin (Tilmicosin, EL-870) and Related Cyclic Amino Derivatives. *J. Antibiot.* 42: 1253-1267.

(Continued)

*Primary Examiner*—Elli Peselev
(74) *Attorney, Agent, or Firm*—Reid S. Willis; John Lemanowicz

(57) ABSTRACT

The present invention relates to 14- or 15-membered macrolides substituted at the 4" position of formula (I)

(I)

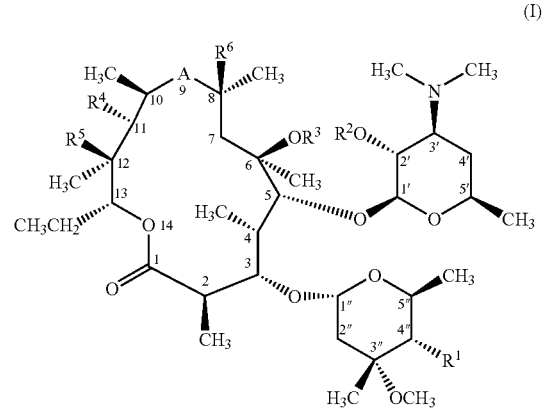

and pharmaceutically acceptable derivatives thereof, to processes for their preparation and their use in therapy or prophylaxis of systemic or topical microbial infections in a human or animal body.

18 Claims, No Drawings

OTHER PUBLICATIONS

Djokic, S., et al. 1988. Erythromycin Series. Part 13. Synthesis and Structure Elucidation of 10-Dihydro-10-deoxo-11-methyl-11-azaerythromycin A. *J. Chem. Res. (S)*: 152-153.

Baker, W.R., et al. 1988. Modification of Macrolide Antibiotics. Synthesis of 11-Deoxy-11-(carboxyamino)-6-*O*-methylerythromycin A 11,12-(cyclic esters) via an Intramolecular Michael Reaction of *O*-Carbamates with an α,β-Unsaturated Ketone. *J. Org. Chem.* 53: 2340-2345.

Houlihan, F., et al. 1985. Phase transfer catalysis in the *tert*-butyloxycarbonylation of alcohols, phenols, enols, and thiols with di-*tert*-butyl dicarbonate. *Can. J. Chem.* 63: 153-162.

Casara, P., et al. 1985. Stereospecific Synthesis of (2*R*,5*R*)-HepT-6-yne-2,5-diamine: A Potent and Selective Enzyme-activated Irreversible Inhibitor of Ornithine Decarboxylase (ODC). *J. Chem. Soc. Perkin Trans.* I: 2201-2208.

Ellis, J., et al. 1973. Synthesis of Some New Iodoquinolines. *Aust. J. Chem.* 26: 907-911.

ETHER LINKED MACROLIDES USEFUL FOR THE TREATMENT OF MICROBIAL INFECTIONS

The present invention claims priority to U.S. Provisional Application 60/679,779 filed May 10, 2005, herein incorporated by reference in its entirety.

FIELD OF THE INVENTION

The present invention relates to novel semi-synthetic macrolides having antimicrobial activity, in particular antibacterial activity. More particularly, the invention relates to 14- and 15-membered macrolides substituted at the 4" position, to processes for their preparation, to compositions containing them and to their use in medicine.

BACKGROUND OF THE INVENTION

Macrolide antibacterial agents are known to be useful in the treatment or prevention of bacterial infections. However, the emergence of macrolide-resistant bacterial strains has resulted in the need to develop new macrolide compounds. For example, EP 0 895 999 describes derivatives modified at the 4" position of the macrolide ring having antibacterial activity.

SUMMARY OF THE INVENTION

According to the present invention, we have now found novel 14- and 15-membered macrolides substituted at the 4" position which also have antimicrobial activity.

Thus, the present invention provides compounds of general formula (I)

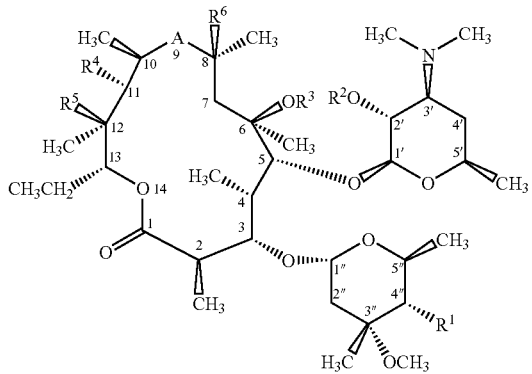

(I)

wherein
A is a bivalent radical selected from —C(O)—, —C(O)NH—, —NHC(O)—, —N($R^7$)—$CH_2$—, —$CH_2$—N($R^7$)—, —CH(N$R^8R^9$)— and —C(=N$R^{10}$)—;
$R^1$ is —O($CH_2$)$_d$X$R^{11}$;
$R^2$ is hydrogen or a hydroxyl protecting group;
$R^3$ is hydrogen, $C_{1-4}$alkyl, or $C_{3-6}$alkenyl optionally substituted by 9 to 10 membered fused bicyclic heteroaryl;
$R^4$ is hydroxy, $C_{2-6}$alkenyloxy optionally substituted by 9 to 10 membered fused bicyclic heteroaryl, or $C_{1-6}$alkoxy optionally substituted by $C_{1-6}$alkoxy or —O($CH_2$)$_e$N$R^7R^{12}$, $R^5$ is hydroxy, or
$R^4$ and $R^5$ taken together with the intervening atoms form a cyclic group having the following structure:

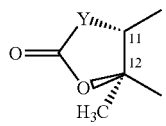

wherein Y is a bivalent radical selected from —$CH_2$—, —CH(CN)—, —O—, —N($R^{13}$)— and —CH(S$R^{13}$)—;
$R^6$ is hydrogen or fluorine;
$R^7$ is hydrogen or $C_{1-6}$alkyl;
$R^8$ and $R^9$ are each independently hydrogen, $C_{1-6}$alkyl, —C(=N$R^{10}$)N$R^{14}R^{15}$ or —C(O)$R^{14}$, or $R^8$ and $R^9$ together form =CH(C$R^{14}R^{15}$)$_f$aryl, =CH(C$R^{14}R^{15}$)$_f$heterocyclyl, =C$R^{14}R^{15}$ or =C($R^{14}$)C(O)O$R^{14}$, wherein the alkyl, aryl and heterocyclyl groups are optionally substituted by up to three groups independently selected from $R^{16}$;
$R^{10}$ is —O$R^{17}$, $C_{1-6}$alkyl, —($CH_2$)$_g$aryl, —($CH_2$)$_g$heterocyclyl or —($CH_2$)$_h$O($CH_2$)$_i$O$R^7$, wherein each $R^{10}$ group is optionally substituted by up to three groups independently selected from $R^{16}$;
$R^{11}$ is a heterocyclic group having the following structure:

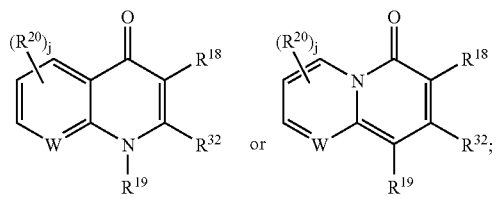

$R^{12}$ is hydrogen or $C_{1-6}$alkyl;
$R^{13}$ is hydrogen or $C_{1-4}$alkyl substituted by a group selected from optionally substituted phenyl, optionally substituted 5 or 6 membered heteroaryl and optionally substituted 9 to 10 membered fused bicyclic heteroaryl;
$R^{14}$ and $R^{15}$ are each independently hydrogen or $C_{1-6}$alkyl;
$R^{16}$ is halogen, cyano, nitro, trifluoromethyl, azido, —C(O)$R^{21}$, —C(O)O$R^{21}$, —OC(O)$R^{21}$, —OC(O)O$R^{21}$, —N$R^{22}$C(O)$R^{23}$, —C(O)N$R^{22}R^{23}$, —N$R^{22}R^{23}$, hydroxy, $C_{1-6}$alkyl, —S(O)$_k$$C_{1-6}$alkyl, $C_{1-6}$alkoxy, —($CH_2$)$_m$aryl or —($CH_2$)$_m$heteroaryl, wherein the alkoxy group is optionally substituted by up to three groups independently selected from —N$R^{14}R^{15}$, halogen and —O$R^{14}$, and the aryl and heteroaryl groups are optionally substituted by up to five groups independently selected from halogen, cyano, nitro, trifluoromethyl, azido, —C(O)$R^{24}$, —C(O)O$R^{24}$, —OC(O)O$R^{24}$, —N$R^{25}$C(O)$R^{26}$, —C(O)N$R^{25}R^{26}$, —N$R^{25}R^{26}$, hydroxy, $C_{1-6}$alkyl and $C_{1-6}$alkoxy;
$R^{17}$ is hydrogen, $C_{1-6}$alkyl, $C_{3-7}$cycloalkyl, $C_{3-6}$alkenyl or a 5 or 6 membered heterocyclic group, wherein the alkyl, cycloalkyl, alkenyl and heterocyclic groups are optionally substituted by up to three substituents independently selected from optionally substituted 5 or 6 membered heterocyclic group, optionally substituted 5 or 6 membered heteroaryl, —O$R^{27}$, —S(O)$_n$$R^{27}$, —N$R^{27}R^{28}$, —CON$R^{27}R^{28}$, halogen and cyano;
$R^{18}$ is hydrogen, —C(O)O$R^{29}$, —C(O)NH$R^{29}$, —C(O)$CH_2NO_2$, or —C(O)$CH_2SO_2R^7$;

$R^{19}$ is hydrogen; $C_{1-4}$alkyl optionally substituted by hydroxy, cyano, $C_{1-4}$alkoxy, $NH_2$, —$NH(C_{1-4}$alkyl) or —$N(C_{1-4}$alkyl)$_2$; $C_{2-4}$alkenyl optionally substituted by hydroxy, cyano, $C_{1-4}$alkoxy, $NH_2$, —$NH(C_{1-4}$alkyl) or —$N(C_{1-4}$alkyl)$_2$; $C_{1-4}$alkoxy; $C_{3-7}$cycloalkyl; —$NH_2$; —$NH(C_{1-4}$alkyl); —$N(C_{1-4}$alkyl)$_2$; $(C_{1-4}$alkyl)OC(O)N(C_{1-4}$alkyl); or optionally substituted phenyl or benzyl;

$R^{20}$ is halogen, $C_{1-4}$alkyl, $C_{1-4}$thioalkyl, $C_{1-4}$alkoxy, —$NH_2$, —$NH(C_{1-4}$alkyl) or —$N(C_{1-4}$alkyl)$_2$;

$R^{21}$ is hydrogen, $C_{1-10}$alkyl, —$(CH_2)_p$aryl or —$(CH_2)_p$heteroaryl;

$R^{22}$ and $R^{23}$ are each independently hydrogen, —$OR^{14}$, $C_{1-6}$alkyl, —$(CH_2)_q$aryl or —$(CH_2)_q$heterocyclyl;

$R^{24}$ is hydrogen, $C_{1-10}$alkyl, —$(CH_2)_r$aryl or —$(CH_2)_r$heteroaryl;

$R^{25}$ and $R^{26}$ are each independently hydrogen, —$OR^{14}$, $C_{1-6}$alkyl, —$(CH_2)_s$aryl or —$(CH_2)_s$heterocyclyl;

$R^{27}$ and $R^{28}$ are each independently hydrogen, $C_{1-4}$alkyl or $C_{1-4}$alkoxy$C_{1-4}$alkyl;

$R^{29}$ is hydrogen or $C_{1-6}$alkyl optionally substituted by up to three groups independently selected from halogen, $C_{1-4}$alkoxy, —$OC(O)C_{1-6}$alkyl and —$OC(O)OC_{1-6}$alkyl, or —$(CH_2)_q$heterocyclyl, —$(CH_2)_q$heteroaryl, —$(CH_2)_q$aryl, —$(CH_2)_qC_{3-7}$cycloalkyl;

$R^{30}$ is hydrogen, $C_{1-4}$alkyl, $C_{3-7}$cycloalkyl, optionally substituted phenyl or benzyl, acetyl or benzoyl;

$R^{31}$ is hydrogen or $R^{20}$, or $R^{31}$ and $R^{19}$ are linked to form the bivalent radical —$O(CH_2)_2$—, —$(CH_2)_t$—; —$NR^7(CH_2)_a$—, —$OCH_2NR^7$—, —$SCH_2NR^7$—, —$CH_2NR^7CH_2$—, —$CH_2OCH_2$—, —$CH_2SCH_2$—, —$(CH_2)_aNR^7$—;

$R^{32}$ is hydrogen, or $R^{32}$ and $R^{19}$ are linked to form the bivalent radical selected from the group —$S(CH_2)_b$—, —$N(R^7)(CH_2)_b$—, —$O(CH_2)_b$—;

$R^{33}$ is $C_{1-8}$alkyl, $C_{2-6}$alkenyl or $C_{2-6}$alkynyl;

X is —$U(CH_2)_vB(CH_2)_vD$-, —$U(CH_2)_vB$—$R^{33}$—, —$U(CH_2)_vB(CH_2)_vD(CH_2)_vE$-, or —$U(CH_2)_vB(CH_2)_vD$-$R^{33}$—, or X is a group selected from:

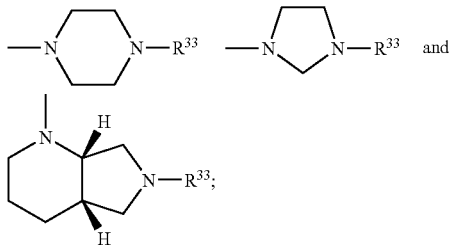

U, B, D and E are independently divalent radicals selected from —$N(R^{30})$—, —$O$—, —$S(O)_z$—, —$N(R^{30})C(O)$—, —$C(O)N(R^{30})$— and —$N[C(O)R^{30}]$—;

W is —$C(R^{31})$— or —$N$—;

a is 1 or 2 b is an integer from 1 to 3;

d is an integer from 2 to 6;

e is an integer from 2 to 4;

f, g, h, m, p, q, r and s are each independently integers from 0 to 4;

i is an integer from 1 to 6;

j, k, n and z are each independently integers from 0 to 2;

t is 2 or 3;

v is an integer independently selected for each occurance from 1 to 8;

and pharmaceutically acceptable derivatives thereof.

DETAILED DESCRIPTION OF THE INVENTION

The term "pharmaceutically acceptable" as used herein means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilised) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (e.g. methanesulphonate, ethanesulphonate, benzenesulphonate or p-toluenesulphonate) and isethionate. Representative examples include trifluoroacetate, acetate and formate salts, for example the bis or tris trifluoroacetate or acetate salts and the mono or diformate salts.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Compounds of the invention may have both a basic and an acidic centre may therefore be in the form of zwitterions.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formula (I) may form solvates (e.g. hydrates) and the invention also includes all such solvates.

The term "prodrug" as used herein means a compound which is converted within the body, e.g. by hydrolysis in the blood, into its active form that has medical effects. Pharmaceutically acceptable prodrugs are described in T. Higuchi and V. Stella, "Prodrugs as Novel Delivery Systems", Vol. 14 of the A.C.S. Symposium Series, Edward B. Roche, ed., "Bioreversible Carriers in Drug Design", American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

References hereinafter to a compound according to the invention include both compounds of formula (I) and their pharmaceutically acceptable derivatives.

With regard to stereoisomers, the compounds of structure (I) have more than one asymmetric carbon atom. In the general formula (I) as drawn, the solid wedge shaped bond indicates that the bond is above the plane of the paper. The broken bond indicates that the bond is below the plane of the paper.

It will be appreciated that the substituents on the macrolide may also have one or more asymmetric carbon atoms. Thus, the compounds of structure (I) may occur as individual enantiomers or diastereomers. All such isomeric forms are included within the present invention, including mixtures thereof.

Where a compound of the invention contains an alkenyl group, cis (Z) and trans (E) isomerism may also occur. The present invention includes the individual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallisation, chromatography or HPLC A stereoisomeric mixture of the agent may also be prepared from a corresponding optically pure intermediate or by resolution, such as HPLC of the corresponding mixture using a suitable chiral support or by fractional crystallisation of the diastereoisomeric salts formed by reaction of the corresponding mixture with a suitable optically active acid or base, as appropriate.

The compounds of structure (I) may be in crystalline or amorphous form. Furthermore, some of the crystalline forms of the compounds of structure (I) may exist as polymorphs, which are included in the present invention.

Compounds wherein $R^2$ represents a hydroxyl protecting group are in general intermediates for the preparation of other compounds of formula (I).

When the group $OR^2$ is a protected hydroxyl group this is conveniently an ether or an acyloxy group. Examples of particularly suitable ether groups include those in which $R^2$ is a trialkylsilyl (i.e. trimethylsilyl). When the group $OR^2$ represents an acyloxy group, then examples of suitable groups $R^2$ include acetyl or benzoyl.

$R^6$ is hydrogen or fluorine. However, it will be appreciated that when A is —C(O)NH— or —CH$_2$—N(R$^7$)—, $R^6$ is hydrogen.

When $R^{11}$ is a heterocyclic group having the following structure:

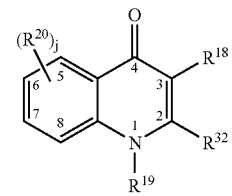

said heterocyclic is linked in the 6 or 7 position to the X group as above defined. When present, the $R^{20}$ group or groups may be attached at any position on the ring. In one embodiment, an $R^{20}$ group is attached at the 6 or 7 position.

When $R^{11}$ is a heterocyclic group having the following structure:

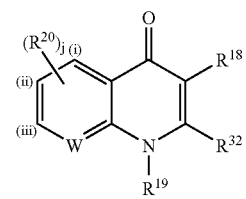

wherein W is —C(R$^{31}$)— where $R^{31}$ is $R^{20}$ or $R^{31}$ and $R^{19}$ are linked to form the bivalent radical —O(CH$_2$)$_2$—, —(CH$_2$)$_t$—, —NR$^7$(CH$_2$)$_a$—, —OCH$_2$NR$^7$—, —SCH$_2$NR$^7$—, —CH$_2$NR$^7$CH$_2$—, —CH$_2$OCH$_2$—, —CH$_2$SCH$_2$—, —(CH$_2$)$_a$NR$^7$—, said heterocyclic is linked in the (ii) or (iii) position to the X group as above defined.

When $R^{11}$ is a heterocyclic group having the following structure:

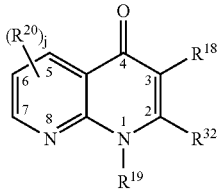

said heterocyclic is linked in the 6 or 7 position to the X group as defined above.

When $R^{11}$ is a heterocyclic group having the following structure:

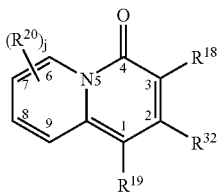

said heterocyclic is linked in the 7 or 8 position to the X group as above defined.

When $R^{11}$ is a heterocyclic group having the following structure:

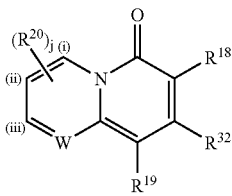

wherein W is —C($R^{31}$)— where $R^{31}$ is $R^{20}$ or $R^{31}$ and $R^{19}$ are linked to form the bivalent radical —O(CH$_2$)$_2$—, —(CH$_2$)$_t$—; —NR$^7$(CH$_2$)$_a$—, —OCH$_2$NR$^7$—, —SCH$_2$NR$^7$—, —CH$_2$NR$^7$CH$_2$—, —CH$_2$OCH$_2$—, —CH$_2$SCH$_2$—, —(CH$_2$)$_a$NR$^7$—, said heterocyclic is linked in the (i), (ii) or (iii) position to the X group as above defined. In one embodiment, the heterocyclic is linked to the (i) position. In another embodiment, the heterocyclic is linked in the (ii) or (iii) position.

When $R^{11}$ is a heterocyclic group having the following structure:

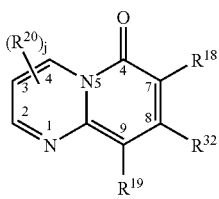

said heterocyclic is linked in the 2 or 3 position to the X group as above defined. In one embodiment, the heterocyclic is linked in the 2 or 3 position. In another embodiment, the heterocyclic is linked in the 4 position.

The term "alkyl" as used herein as a group or a part of a group refers to a straight or branched hydrocarbon chain containing the specified number of carbon atoms. For example, $C_{1-10}$alkyl means a straight or branched alkyl containing at least 1, and at most 10, carbon atoms. Examples of "alkyl" as used herein include, but are not limited to, methyl, ethyl, n-propyl, n-butyl, n-pentyl, isobutyl, isopropyl, t-butyl, hexyl, heptyl, octyl, nonyl and decyl. A $C_{1-4}$alkyl group is preferred, for example methyl, ethyl, n-propyl, isopropyl, n-butyl, isobutyl or t-butyl.

The term "$C_{3-7}$cycloalkyl" group as used herein refers to a non-aromatic monocyclic hydrocarbon ring of 3 to 7 carbon atoms such as, for example, cyclopropyl, cyclobutyl, cyclopentyl, cyclohexyl or cycloheptyl.

The term "alkoxy" as used herein refers to a straight or branched chain alkoxy group containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$alkoxy group is preferred, for example methoxy, ethoxy, propoxy, prop-2-oxy, butoxy, but-2-oxy or 2-methylprop-2-oxy.

The term "alkenyl" as used herein as a group or a part of a group refers to a straight or branched hydrocarbon chain containing the specified number of carbon atoms and containing at least one double bond. For example, the term "$C_{2-6}$alkenyl" means a straight or branched alkenyl containing at least 2, and at most 6, carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. It will be appreciated that in groups of the form —O—$C_{2-6}$alkenyl, the double bond is preferably not adjacent to the oxygen.

The term "alkynyl" as used herein as a group or a part of a group refers to a straight or branched hydrocarbon chain containing the specified number of carbon atoms and containing at least one triple bond. For example, the term "$C_{2-6}$alkynyl" means a straight or branched alkynyl containing at least 2, and at most 6, carbon atoms and containing at least one triple bond. Examples of "alkynyl" as used herein include, but are not limited to, ethynyl, 2-propynyl, 3-butynyl, 2-butynyl, 2-pentynyl, 3-pentynyl, 3-methyl-2-butynyl, 3-methylbut-2-ynyl, 3-hexynyl and 1,1-dimethylbut-2-ynyl. It will be appreciated that in groups of the form —O—$C_{2-6}$alkynyl, the triple bond is preferably not adjacent to the oxygen.

The term "aryl" as used herein refers to an aromatic carbocyclic moiety such as phenyl, biphenyl or naphthyl.

The term "heteroaryl" as used herein, unless otherwise defined, refers to an aromatic heterocycle of 5 to 10 members, having at least one heteroatom selected from nitrogen, oxygen and sulfur, and containing at least 1 carbon atom, including both mono and bicyclic ring systems. Examples of heteroaryl rings include, but are not limited to, furanyl, thiophenyl, pyrrolyl, pyrazolyl, imidazolyl, oxazolyl, isoxazolyl, thiazolyl, isothiazolyl, triazolyl, oxadiazolyl, tetrazolyl, thiadiazolyl, pyridyl, pyridazinyl, pyrazinyl, pyrimidinyl, triazinyl, quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl and benzothiophenyl.

The term "5 or 6 membered heteroaryl" as used herein as a group or a part of a group refers to a monocyclic 5 or 6 membered aromatic heterocycle containing at least one heteroatom independently selected from oxygen, nitrogen and sulfur Examples include, but are not limited to, furanyl, thiophenyl, pyrrolyl, pyrazolyl, imidazolyl, oxazolyl, isoxazolyl, thiazolyl, isothiazolyl, triazolyl, oxadiazolyl, tetrazolyl, pyridyl, pyridazinyl, pyrazinyl, pyrimidinyl and triazinyl.

The term "9 to 10 membered fused bicyclic heteroaryl" as used herein as a group or a part of a group refers to quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl or benzothiophenyl.

The term "heterocyclyl" as used herein, unless otherwise defined, refers to a monocyclic or bicyclic three- to ten-membered saturated or non-aromatic, unsaturated hydrocarbon ring containing at least one heteroatom selected from oxygen, nitrogen and sulfur. Preferably, the heterocyclyl ring has five or six ring atoms. Examples of heterocyclyl groups include, but are not limited to, pyrrolidinyl, tetrahydrofuranyl, tetrahydrothiophenyl, imidazolidinyl, pyrazolidinyl, piperidyl, piperazinyl, morpholino, tetrahydropyranyl and thiomorpholino.

The term "5 or 6 membered heterocyclic group" as used herein as a group or part of a group refers to a monocyclic 5 or 6 membered saturated hydrocarbon ring containing at least one heteroatom independently selected from oxygen, nitrogen and sulfur. Examples of such heterocyclyl groups include, but are not limited to, pyrrolidinyl, tetrahydrofuranyl, tetrahydrothiophenyl, imidazolidinyl, pyrazolidinyl, piperidyl, piperazinyl, morpholino, tetrahydropyranyl and thiomorpholino.

The term "halogen" refers to a fluorine, chlorine, bromine or iodine atom.

The terms "optionally substituted phenyl", "optionally substituted phenyl or benzyl", "optionally substituted 5 or 6 membered heteroaryl", "optionally substituted 9 to 10 membered fused bicyclic heteroaryl" or "optionally substituted 5 or 6 membered heterocyclic group" as used herein refer to a group which is substituted by 1 to 3 groups selected from halogen, $C_{1-4}$alkyl, $C_{1-4}$alkoxy, hydroxy, nitro, cyano, amino, $C_{1-4}$alkylamino or di$C_{1-4}$alkylamino, phenyl and 5 or 6 membered heteroaryl.

In one embodiment, A is —C(O)—, —C(O)NH—, —NHC(O)—, —N($R^7$)—$CH_2$—, —$CH_2$—N($R^7$)— or —CH(N$R^8R^9$)—. In another embodiment, A is —C(O)—, —C(O)NH—, —NHC(O)—, —$CH_2$—N($R^7$)—, —CH(N$R^8R^9$)— or —C(=N$R^{10}$)—. In a further embodiment, A is —C(O)—, —C(O)NH—, —NHC(O)—, —$CH_2$—N$R^7$— or —CH(N$R^8R^9$)—. Representative examples of A include —C(O)— and —N($R^7$)—$CH_2$—.

A representative example of $R^2$ is hydrogen.

Representative examples of $R^3$ include hydrogen and $C_{1-4}$alkyl, in particular hydrogen and methyl.

In one embodiment, $R^4$ is hydroxy or $C_{1-6}$alkoxy, in particular hydroxy or methoxy. In another embodiment, $R^5$ is hydroxy. Alternatively, $R^4$ and $R^5$ taken together with the intervening atoms form a cyclic group having the following structure:

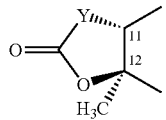

wherein Y is a bivalent radical selected from —O— and —N($R^{13}$)—.

A representative example of $R^6$ is hydrogen.

A representative example of $R^7$ is $C_{1-6}$alkyl, for example $C_{1-4}$alkyl, in particular methyl.

Representative examples of $R^{11}$ include heterocyclic groups having the following structures:

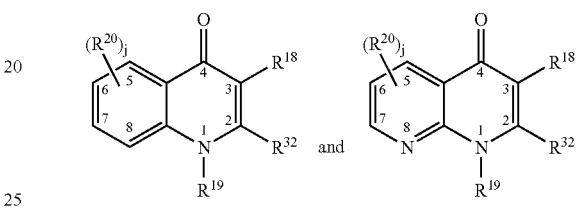

wherein the heterocyclic is linked in the 6 or 7 position to the X group as above defined, and heterocyclic groups having the following structure:

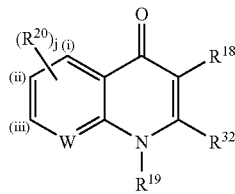

wherein W is —C($R^{31}$)— and $R^{31}$ and $R^{19}$ are linked to form the bivalent radical —$(CH_2)_t$—, and the heterocyclic is linked in the (ii) or (iii) position to the X group as above defined.

A representative example of $R^{13}$ is hydrogen and $C_{1-4}$alkyl, in particular methyl.

In one embodiment, $R^{18}$ is —C(O)O$R^{29}$, —C(O)NH$R^{29}$, —C(O)$CH_2$$NO_2$. or —C(O)$CH_2$$SO_2R^7$. A representative example of $R^{18}$ is —C(O)O$R^{29}$ such as —C(O)OH.

Representative examples of $R^{19}$ include $C_{1-4}$alkyl, such as ethyl, $C_{3-7}$cycloalkyl, such as cyclopropyl and —N($C_{1-4}$alkyl)$_2$ such as dimethylamine.

In one embodiment, $R^{20}$ is halogen, in particular chlorine or fluorine, or methoxy.

In one embodiment, $R^{30}$ is hydrogen or $C_{1-4}$alkyl. A representative example of $R^{30}$ is hydrogen or methyl.

A representative example of $R^{31}$ is hydrogen, or $R^{31}$ and $R^{19}$ are linked to form the bivalent radical —$(CH_2)_t$—.

A representative example of $R^{33}$ is $C_{1-4}$alkyl, such as ethyl or propyl. In one embodiment $R^{33}$ is $C_{2-6}$alkenyl such as —$CH_2CH=CH_2$.

A representative example of X is —U($CH_2$)$_v$B($CH_2$)$_v$D—, —U($CH_2$)$_v$B—$R^{33}$—, —U($CH_2$)$_v$B($CH_2$)$_v$D($CH_2$)$_v$E— or —U($CH_2$)$_v$B($CH_2$)$_v$D-$R^{33}$—.

Representative examples of U, B, D and E include the divalent radicals —N($R^{30}$)—, —O—, S(O)$_n$—, —N($R^{30}$)C(O)— and —C(O)N($R^{30}$)—. In one embodiment B may represent —O— or —N(R³⁰)— such as —NH—. In one embodiment D may represent —O— or —N(R³⁰)—. In one aspect of the invention E may represent —N(R³⁰)—. In one embodiment U may represent —N(R³⁰)— or —O—, such as —NH— or —N(CH₃)—. In another embodiment of the invention U may represent —N(R³⁰)C(O)—, such as —NHC(O)—. In another embodiment bU may represent —S(O)$_z$— such as —SO₂—.

A representative example of d is 2 to 4, for example 2 or 3.
A representative example of v is 1 to 4, for example 2 or 3.
In one embodiment, j is 0 to 2. A representative example of j is 0 or 1.
A representative example of t is 3.
A representative example of z is 0.

Particularly preferred compounds of the invention are:
4"-O-[2-(2-{2-[2-(3-Carboxy-7-chloro-1-cyclopropyl-4-oxo-1,4-dihydro-quinolin-6-ylamino)-ethoxy]-ethoxy}-ethylamino)-ethyl]-azithromycin 11,12-cyclic carbonate;
4"-O-(2-{2-[2-(3-Carboxy-7-chlorine-1-cyclopropyl-4-oxo-1,4-dihydro-quinolin-6-ylamino)-ethoxy]-ethylamino}-ethyl)-azithromycin 11,12-cyclic carbonate;
4"-O-[3-(2-{2-[2-(3-Carboxy-7-chloro-1-cyclopropyl-4-oxo-1,4-dihydro-quinolin-6-ylamino)-ethoxy]-ethoxy}-ethyl amino)-propyl]-azythromycin 11,12-cyclic carbonate;
4"-O-(3-{2-[3-(3-Carboxy-1-ethyl-4-oxo-1,4-dihydro-quinolin-6-yl)-propoxy]-ethylamnio}-propyl)-azithromycin;
4"-O-{2-[(2-{[3-(3-Carboxy-1-ethyl-4-oxo-1,4-dihydro-6-quinolinyl)-propyl]oxy}ethyl)-amino]ethyl}-6-O-methyl-erythromycin A;
4"-O-(3-{2-[(E)-3-(3-Carboxy-1-ethyl-4-oxo-1,4-dihydro-quinolin-6-yl)-allyloxy]-ethoxy}-propyl)-11-O-methyl azithromycin;
4"-O-(3-{2-[3-(3-Carboxy-1-ethyl-4-oxo-1,4-dihydro-quinolin-6-yl)-propoxy]-ethoxy}-propyl)-11-O-methyl azithromycin;
4"-O-(3-{3-[3-(3-Carboxy-1-dimethylamino-4-oxo-1,4-dihydro-quinolin-6-yl)-propoxy]-propionylamino}-propyl)-6-O-methyl-erythromycin A;
4"-O-[3-(3-{2-[2-(3-carboxy-7-chloro-1-cyclopropyl-4-oxo-1,4-dihydro-quinolin-6-ylamino)-ethoxy]-ethoxy}-propionylamino)-propyl]-azithromycin-11,12-cyclic carbonate;
4"-O-[3-(3-{2-[2-(3-carboxy-7-chloro-1-cyclopropyl-4-oxo-1,4-dihydro-quinolin-6-ylamino)-ethoxy]-ethoxy}-propionylamino)-propyl]-azithromycin;
4"-O-(3-{3-[3-(3-Carboxy-1-cyclopropyl-4-oxo-1,4-dihydro-quinolin-6-yl)-allyloxy]-propoxy}-propyl)-azithromycin;
4"-O-(3-{3-[3-(3-Carboxy-1-cyclopropyl-4-oxo-1,4-dihydro-quinolin-6-yl)-propoxy]-propoxy}-propyl)-azithromycin;
4"-O-(3-{2-[3-(3-Carboxy-1-dimethylamino-4-oxo-1,4-dihydro-quinolin-6-yl)-allyloxy]-ethoxy}-propyl)-azithromycin;
4"-O-(3-{2-[3-(3-Carboxy-1-dimethylamino-4-oxo-1,4-dihydro-quinolin-6-yl)-propoxy]-ethoxy}-propyl)-azithromycin;
4"-O-(2-{2-[2-(3-Carboxy-6-fluoro-1-cyclopropyl-4-oxo-1,4-dihydro-quinolin-7-ylamino)-ethoxy]-ethylamino}-ethyl)-azithromycin 11,12-cyclic carbonate;
4"-O-(2-{2-[2-(3-Carboxy-6-fluoro-1-cyclopropyl-4-oxo-1,4-dihydro-quinolin-7-ylamino)-ethoxy]-ethylamino}-ethyl)-azithromycin;
4"-O-{2-({2-[(2-{[2-(3-Carboxy-1-ethyl-4-oxo-1,4-dihydro-6-quinolinyl)ethyl]oxy}ethyl)oxy]ethyl}amino)ethyl}-6-O-methyl-erythromycin A formate;
4"-O-{2-({2-[(2-{[2-(3-Carboxy-1-ethyl-4-oxo-1,4-dihydro-6-quinolinyl)ethyl]oxy}ethyl)oxy]ethyl}methylamino)ethyl}-6-O-methyl-erythromycin A;
4"-O-(2-{[2-({3-[3-Carboxy-1-(dimethylamino)-4-oxo-1,4-dihydro-6-quinolinyl]propyl}-amino)ethyl]sulfonyl}ethyl)-6-O-methyl erythromycin A 11,12-carbonate;
4"-O-(3-{2-[3-(3-Carboxy-1-ethyl-4-oxo-1,4-dihydro-quinolin-6-yl)-allyloxy]-ethoxy}-propyl)-azithromycin;
4"-O-(3-{2-[3-(3-Carboxy-1-ethyl-4-oxo-1,4-dihydro-quinolin-6-yl)-propoxy]-ethoxy}-propyl)-azithromycin; and
4"-O-(3-{3-[2-(3-Carboxy-7-chloro-1-cyclopropyl-4-oxo-1,4-dihydro-quinolin-6-ylamino)-ethoxy]-propionylamino}-propyl)-6-O-methyl erythromycin A 11,12-cyclic carbamate, or pharmaceutically acceptable derivatives thereof.

Compounds according to the invention also exhibit a broad spectrum of antimicrobial activity, in particular antibacterial activity, against a wide range of clinical pathogenic microorganisms. Using a standard microtiter broth serial dilution test, compounds of the invention have been found to exhibit useful levels of activity against a wide range of pathogenic microorganisims. For example, the compounds of the invention may be active against strains of *Staphylococcus aureus, Streptopococcus pneumoniae, Moraxella catarrhalis, Streptococcus pyogenes, Haemophilus influenzae, Enterococcus faecalis, Chlamydia pneumoniae, Mycoplasma pneumoniae* and *Legionella pneumophila*. The compounds of the invention may also be active against resistant strains, for example erythromycin resistant strains. For example, the compounds of the invention may be active against erythromycin resistant strains of *Streptococcus pneumoniae, Streptococcus pyogenes* and *Staphylococcus aureus*.

The compounds of the invention may therefore be used for treating a variety of diseases caused by pathogenic microorganisms, in particular bacteria, in human beings and animals. It will be appreciated that reference to treatment includes acute treatment or prophylaxis as well as the alleviation of established symptoms.

Thus, according to another aspect of the present invention we provide a compound of formula (I) or a pharmaceutically acceptable derivative thereof for use in therapy.

According to a further aspect of the invention we provide a compound of formula (I) or a pharmaceutically acceptable derivative thereof for use in the therapy or prophylaxis of systemic or topical microbial infections in a human or animal subject.

According to a further aspect of the invention we provide the use of a compound of formula (I) or a pharmaceutically acceptable derivative thereof in the manufacture of a medicament for use in the treatment or prophylaxis of systemic or topical microbial infections in a human or animal body.

According to a yet further aspect of the invention we provide a method of treatment of the human or non-human animal body to combat microbial infections comprising administration to a body in need of such treatment of an effective amount of a compound of formula (I) or a pharmaceutically acceptable derivative thereof.

While it is possible that, for use in therapy, a compound of the invention may be administered as the raw chemical it is preferable to present the active ingredient as a pharmaceutical formulation eg when the agent is in admixture with a suitable pharmaceutical excipient, diluent or carrier selected with regard to the intended route of administration and standard pharmaceutical practice.

Accordingly, in one aspect, the present invention provides a pharmaceutical composition or formulation comprising at least one compound of the invention or a pharmaceutically acceptable derivative thereof in association with a pharmaceutically acceptable excipient, diluent and/or carrier. The excipient, diluent and/or carrier must be "acceptable" in the sense of being compatible with the other ingredients of the formulation and not deleterious to the recipient thereof.

In another aspect, the invention provides a pharmaceutical composition comprising, as active ingredient, at least one compound of the invention or a pharmaceutically acceptable derivative thereof in association with a pharmaceutically acceptable excipient, diluent and/or carrier for use in therapy, and in particular, in the treatment of human or animal subjects suffering from a condition susceptible to amelioration by an antimicrobial compound.

In another aspect, the invention provides a pharmaceutical composition comprising a therapeutically effective amount of the compounds of the present invention and a pharmaceutically acceptable excipient, diluent and/or carrier (including combinations thereof).

There is further provided by the present invention a process of preparing a pharmaceutical composition, which process comprises mixing at least one compound of the invention or a pharmaceutically acceptable derivative thereof, together with a pharmaceutically acceptable excipient, diluent and/or carrier.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable excipients, diluents and/or carriers. Acceptable excipients, diluents and carriers for therapetic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as—or in addition to—the excipient, diluent and/or carrier any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO 91/11172, WO 94/02518 and WO 98/55148.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

There may be different composition/formulation requirements depending on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution, which may contain other substances, for example enough salts or monosaccharides to make the solution isotonic with blood. For buccal or sublingual administration the compositions may be administered in the form of tablets or lozenges, which can be formulated in a conventional manner.

It is to be understood that not all of the compounds need be administered by the same route. Likewise, if the composition comprises more than one active component, then those components may be administered by different routes.

The compositions of the invention include those in a form especially formulated for parenteral, oral, buccal, rectal, topical, implant, ophthalmic, nasal or genito-urinary use. For some applications, the agents of the present invention are delivered systemically (such as orally, buccally, sublingually), more preferably orally. Hence, preferably the agent is in a form that is suitable for oral delivery.

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent; and/or by using infusion techniques.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g. eye ear or nose drops) or pour-ons.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water.

Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds may also be dermally or transdermally administered, for example, by use of a skin patch.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

As indicated, the compound of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134AT"") or 1,1,1,2,3,3,3-heptafluoropropane (HFA 227EA), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebuliser.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may for example be used for topical administration with other active ingredients such as corticosteroids or antifungals as appropriate.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compositions may contain from 0.01-99% of the active material. For topical administration, for example, the composition will generally contain from 0.01-10%, more preferably 0.01-1% of the active material.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses.

For systemic administration the daily dose as employed for adult human treatment will range from 2-100 mg/kg body weight, preferably 5-60 mg/kg body weight, which may be administered in 1 to 4 daily doses, for example, depending on the route of administration and the condition of the patient. When the composition comprises dosage units, each unit will preferably contain 200 mg to 1 g of active ingredient. The duration of treatment will be dictated by the rate of response rather than by arbitrary numbers of days.

Compounds of general formula (I) and pharmaceutically acceptable derivatives thereof may be prepared by the general methods outlined hereinafter, said methods constituting a further aspect of the invention. In the following description, the groups $R^1$ to $R^{33}$, A, B, D, E, X, Y, U, W, a, b, d, e, f, g, h, i, j, k, m, n, p, q, r, s, t, v and z are as defined for the compounds of formula (I) unless otherwise stated.

The group $X^aR^{11a}$ is $XR^{11}$ as defined for formula (I) or a group convertible to $XR^{11}$. Conversion of a group $X^aR^{11a}$ to a $XR^{11}$ group typically arises if a protecting group is needed during the reactions described below. In one preferred embodiment, convertible means that the group can be formed by cleaving a protecting group from the compound. A comprehensive discussion of the ways in which such groups may be protected and methods for cleaving the resulting protected derivatives is given by for example T. W. Greene and P. G. M Wuts in Protective Groups in Organic Synthesis $2^{nd}$ ed., John Wiley & Son, Inc 1991 and by P. J. Kocienski in Protecting Groups, Georg Thieme Verlag 1994 which are incorporated herein by reference. Examples of suitable amino protecting groups include acyl type protecting groups (e.g. formyl, trifluoroacetyl and acetyl), aromatic urethane type protecting groups (e.g. benzyloxycarbonyl (Cbz) and substituted Cbz, and 9-fluorenylmethoxycarbonyl (Fmoc)), aliphatic urethane protecting groups (e.g. t-butyloxycarbonyl (Boc), isopropyloxycarbonyl and cyclohexyloxycarbonyl) and alkyl type protecting groups (e.g. benzyl, trityl and chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate. Hydroxy groups may be protected by reaction of for example acetic anhydride, benzoic anhydride or a trialkylsilyl chloride in an aprotic solvent. Examples of aprotic solvents are dichloromethane, N,N-dimethylformamide, dimethylsulfoxide, tetrahydrofuran and the like.

The compound of Formula (I), wherein U is a divalent radical —N($R^{30}$)— and B, D, E, $R^{11}$, $R^{33}$ and are as defined above may be prepared by reductive amination of the aldehyde of Formula (II)

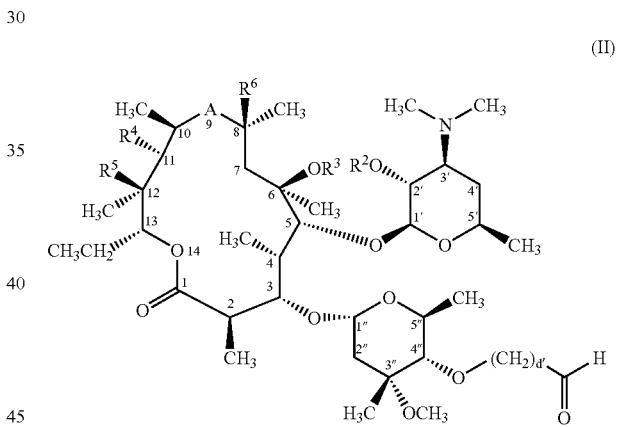

(II)

with a suitable amine (IIIa), (IIIb), (IIIc), or (IIId),

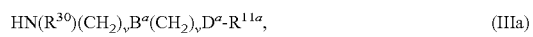 (IIIa)

 (IIIb)

 (IIIc)

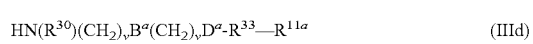 (IIId)

wherein $B^a$, $D^a$, $E^a$, $R^{33}$, $R^{11a}$ and v are as defined for Formula (I) or are groups convertible to B, D, E and $R^{11}$.

The reductive amination reaction is preferably carried out in a solvent such as methanol and DMF. A suitable reducing agent is, for example, sodium cyanoborohydride.

Compounds of formula (II) where d' is 1 or 2 may be prepared from suitably protected compounds of formula (IV)

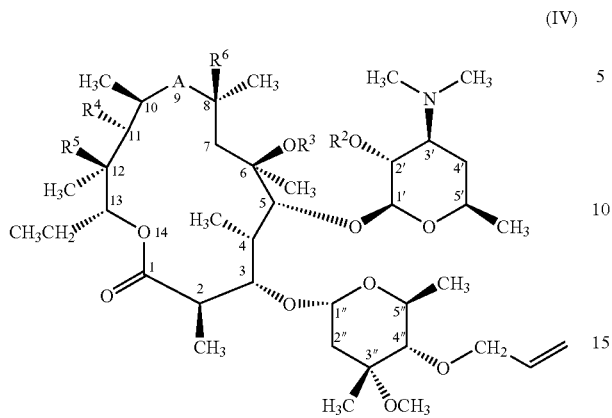

(IV)

by hydroboration with 9-BBN, or other suitable boranes, followed by treatment with peroxide and then oxidation (d'=2), or by osmium tetroxide/peridoate cleavage (d'=1).

Compound of formula (IV) can be formed by palladium-catalysed allylation of suitably 2' hydroxy protected compounds of Formula (VIII).

In a further embodiment the compound of Formula (I), wherein U is a group selected from —N($R^{30}$)—, —O— and —S— and d is an integer from 2 to 6, may be prepared by reaction of a compound of formula (V),

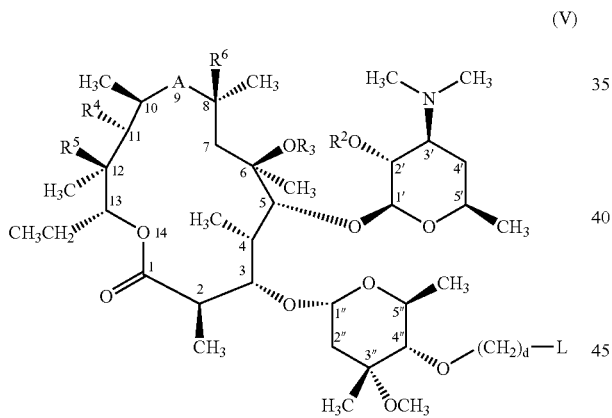

(V)

wherein L is a leaving group with a compound of formula (VI):

$X^a R^{11a}$ (VI)

wherein $X^a$ and $R^{11a}$ are as defined for Formula (I) or a group convertible to $R^{11}$ and X.

Leaving groups, L, are any leaving groups known in the art to be suitable for this type of reaction. Preferably, L is selected from chloride, bromide, iodide, tosyloxy and methanesulfonyloxy group.

The reaction is preferably carried out in a solvent such as a halohydrocarbon (e.g. dichloromethane), an ether (e.g. tetrahydrofuran or dimethoxyethane), acetonitrile or ethyl acetate and the like, dimethylsulfoxide, N,N-dimethylformamide or 1-methyl-pyrrolidone and in the presence of a base, followed, if desired, by removal of the hydroxyl protecting group $R^2$ and conversion of the $X^a R^{11a}$ group to $XR^{11}$.

Examples of the bases which may be used include organic bases such as diisopropylethylamine, triethylamine and 1,8-diazabicyclo[5.4.0]undec-7-ene (DBU), and inorganic bases such as potassium hydroxide, cesium hydroxide, tetraalkylammonium hydroxide, sodium hydride, potassium hydride and the like. Suitable leaving groups for this reaction include halide (e.g. chloride, bromide or iodide) or a sulfonyloxy group (e.g. tosyloxy or methanesulfonyloxy).

In a further embodiment of the invention, compounds of formula (I) wherein U is a group selected from —N($R^{30}$)—, —O—, —N($R^{30}$)C(O)— and —C(O)N($R^{30}$)—, and d is 2, may be prepared by reaction of suitable protected compound of formula (VII),

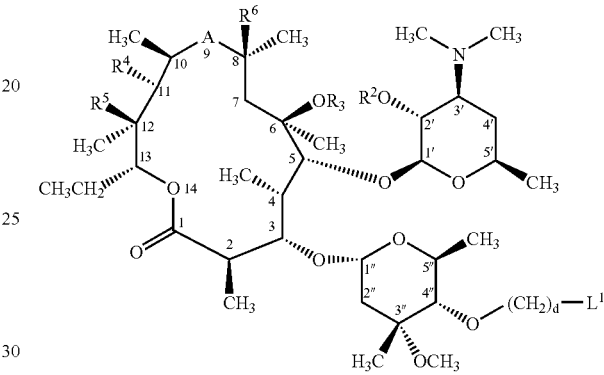

(VII)

wherein d is 2 and $L^1$ is suitable functional group such as —$NH_2$, —$CH_2OH$, CHO or —COOH with a suitable compound of formula (VI), as defined above.

Compound of formula (VII) wherein d is 2 and $L^1$ is suitable functional group such as —$NH_2$, —$CH_2OH$, CHO or —COOH may be prepared by reaction of suitable protected compound of formula (VIII)

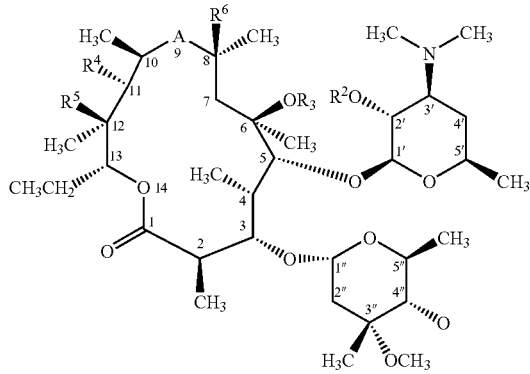

(VIII)

with acrylonitrile in the presence of strong base such as NaOH, KO$^t$Bu, NaO$^t$Bu or NaH in suitable solvent such as for example DMSO/t-BuOH, followed by reduction of cyano group to —$NH_2$, —$CH_2OH$ or CHO group, or by hydrolysis of cyano group to —COOH group.

In a yet further embodiment the compound of Formula (I), wherein d is 2 and X is —$SO_2(CH_2)_2N(R^{30})(CH_2)_vD^a$-$R^{11a}$, —$SO_2(CH_2)_2N(R^{30})(CH_2)_vR^{33}$—$R^{11a}$,  —$SO_2(CH_2)_2N$ (R$^{30}$)—(CH$_2$)$_v$D$^a$(CH$_2$)$_v$E$^a$-R$^{11a}$, or —SO$_2$(CH$_2$)$_2$N(R$^{30}$)(CH$_2$)$_v$D$^a$-R$^{33}$—R$^{11a}$ may be prepared by reaction of suitably protected compound of Formula (IX)

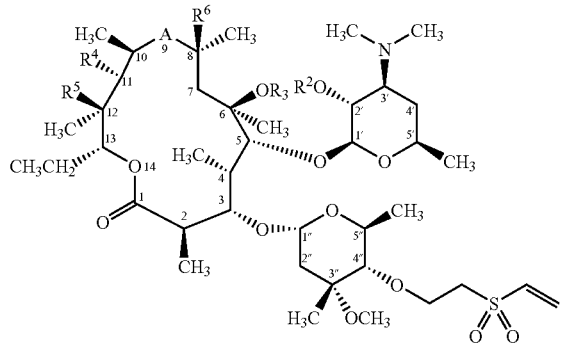

(IX)

with an amine (IIIe), (IIIf), (IIIg), or (IIIh),

HN(R$^{30}$)(CH$_2$)$_v$D$^a$-R$^{11a}$, (IIIe)

HN(R$^{30}$)(CH$_2$)$_v$R$^{33}$—R$^{11a}$, (IIIf)

HN(R$^{30}$)(CH$_2$)$_v$D$^a$(CH$_2$)$_v$E$^a$-R$^{11a}$, or (IIIg)

HN(R$^{30}$)(CH$_2$)$_v$D$^a$-R$^{33}$—R$^{11a}$ (IIIh)

wherein D$^a$, E$^a$, R$^{33}$, R$^{11a}$ and v are as defined for Formula (I) or are independently groups convertible to D, E and R$^{11}$.

The reaction is suitably carried out in a solvent such as dimethylsulfoxide, N,N-dimethylformamide, 1-methyl-pyrrolidinone, a halohydrocarbon (e.g. dichloromethane), an ether (e.g. tetrahydrofuran or dimethoxyethane), acetonitrile or alcohol (e.g methanol or isopropanol) and the like, and in the presence of a base, followed, if desired, by removal of protecting groups.

Compound of Formula (IX) may be prepared by reaction of suitable protected compound of Formula (VIII) with divinyl sulfone in the presence of base, for example an in-organic base (such as sodium hydride) and suitable solvent (e.g. DMSO, acetonitrile, and tert-butanol).

In one embodiment, the compound of formula (I) is prepared by reacting a compound of formula (II) or (IX) with a suitable amine of a formula (III) or reacting a compound of formula (V) or (VII) with a compound of the formula (VI), wherein each of B$^a$, D$^a$, E$^a$, R$^{33}$, X$^a$, R$^{11a}$ and v is as defined for formula (I) or is a protecting group which may be cleaved to form the variable as defined in formula (I).

Compounds of formula (I) may be converted into other compounds of formula (I). Thus compounds of formula (I) wherein U or B is —S(O)$_z$— and z is 1 or 2 may be prepared by oxidation of the corresponding compound of formula (I) wherein z is 0. The oxidation is preferably carried out using a peracid, e.g. peroxybenzoic acid, followed by treatment with a phosphine, such as triphenylphosphine. The reaction is suitably carried out in an organic solvent such as methylene chloride.

Compounds of formula (I) wherein U, B, D or E is —N(R$^{30}$)— and R$^{30}$ is C$_{1-4}$alkyl can be prepared from corresponding compounds wherein R$^{30}$ is hydrogen by reductive alkylation.

Compounds of Formula (I), if required, can be converted into a pharmaceutically acceptable derivative thereof.

Compounds of formula (II) wherein A is —C(O)NH— or —NHC(O)—, R$^4$ or R$^5$ are hydroxy, R$^3$ is hydrogen and R$^6$ is hydrogen are known compounds or they may be prepared by analogous methods to those known in the art. Thus they can be prepared according to the procedures described in EP 507595 and EP 503932.

Compounds of formula (II), wherein A is —C(O)NH— or —NHC(O)—, R$^4$ or R$^5$ are hydroxy and R$^3$ is C$_{1-4}$alkyl or C$_{3-6}$alkenyl optionally substituted by 9 to 10 membered fused bicyclic heteroaryl and R$^6$ is hydrogen are known compounds or they may be prepared by analogous methods to those known in the art. Thus they can be prepared according to the procedures described in WO 9951616 and WO 0063223.

Compounds of formula (II), wherein A is —C(O)NH—, R$^4$ and R$^5$ taken together with the intervening atoms form a cyclic group having the following structure:

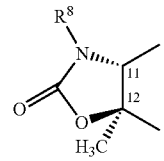

R$^3$ is C$_{1-4}$alkyl, or C$_{3-6}$alkenyl optionally substituted by 9 to 10 membered fused bicyclic heteroaryl and R$^6$ is hydrogen are known compounds or they may be prepared by analogous methods to those known in the art. Thus they can be prepared according to the procedures described in U.S. Pat. No. 6,262,030.

Compounds of formula (II), wherein A is —C(O)—, —C(O)NH—, —NHC(O)—, —N(R$^7$)—CH$_2$—, —CH$_2$—N(R$^7$)— or —CH(NR$^8$R$^9$)—, R$^4$ or R$^5$ are hydroxy or R$^4$ and R$^5$ taken together with the intervening atoms form a cyclic group having the following structure:

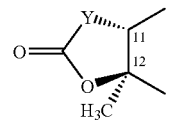

wherein Y is a bivalent radical selected from —O— and —N(R$^{13}$)—, and R$^3$ is C$_{1-4}$alkyl, or C$_{3-6}$alkenyl optionally substituted by 9 to 10 membered fused bicyclic heteroaryl are known compounds or they may be prepared by analogous methods to those known in the art. Thus they can be prepared according to the procedures described in EP 307177, EP 248279, WO 0078773, WO 9742204.

Compounds of formula (II), wherein A is —C(O)NH—, —NHC(O)—, —N(CH$_3$)—CH$_2$— or —CH$_2$—N(CH$_3$)—, R$^4$ or R$^5$ are hydroxy or R$^4$ and R$^5$ taken together with the intervening atoms form a cyclic group having the following structure:

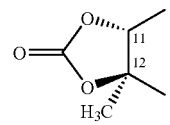

and R$^6$ is hydrogen are known compounds or they may be prepared by analogous methods to those known in the art.

Thus they can be prepared according to the procedures described in EP 508699 and J. Chem. Res. Synop (1988 pages 152-153), U.S. Pat. No. 6,262,030.

Compounds of formula (II), wherein A is —C(=NR$^{10}$)—, R$^4$ or R$^5$ are hydroxy or R$^4$ and R$^5$ taken together with the intervening atoms form a cyclic group having the following structure:

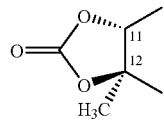

and R$^6$ is hydrogen, are known compounds or they may be prepared by analogous methods to those known in the art. Thus, they can be prepared according to the procedures described in EP 284203.

Compounds of formula (II), wherein A is —C(O)—, R$^4$ and R$^5$ taken together with the intervening atoms form a cyclic group having the following structure:

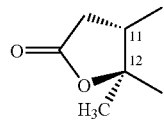

R$^6$ is hydrogen and R$^3$ is C$_{1-4}$ alkyl may be prepared by decarboxylation of a compound of formula (X),

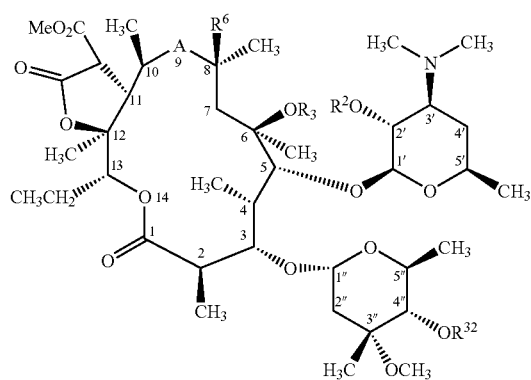

(X)

wherein R$^{32}$ is amino protecting group followed, if required, by removal of the protecting group R$^2$ or R$^{32}$.

The decarboxylation may be carried out in the presence of a lithium salt such as lithium chloride, preferably in an organic solvent such as dimethylsulfoxide.

Compounds of formula (II), wherein A is —C(O)—, R$^4$ and R$^5$ taken together with the intervening atoms form a cyclic group having the following structure:

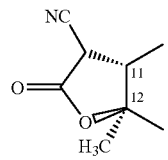

and R$_3$ is C$_{1-4}$ alkyl may be prepared according to the procedures described in WO 02/50091 and WO 02/50092.

Compound of formula (XI):

$$R^{11a}L \quad (XI)$$

wherein L is a suitable leaving group such as chlorine, fluorine or bromine, and R$^{31}$ and R$^{19}$ are linked to form the bivalent radical —O(CH$_2$)$_2$—, —(CH$_2$)$_t$—, —NR$^7$(CH$_2$)$_a$—, —OCH$_2$NR$^7$—, —SCH$_2$NR$^7$—, —CH$_2$NR$^7$CH$_2$—, —CH$_2$OCH$_2$—, —CH$_2$SCH$_2$— or —(CH$_2$)$_a$NR$^7$— are known compounds or they may be prepared by analogous methods to those known in the art. Thus, they can be prepared according to the procedures described in U.S. Pat. No. 6,624,159.

Compound of formula R$^{11a}$L (XI), wherein L is a suitable leaving group such as chlorine, fluorine or bromine, and R$^{32}$ and R$^{19}$ are linked to form the bivalent radical selected from the group —S(CH$_2$)$_b$—, —N(R$^7$)(CH$_2$)$_b$— or —O(CH$_2$)$_b$— are known compounds or they may be prepared by analogous methods to those known in the art. Thus, they can be prepared according to the procedures described in Arch. Pharm. Pharm. Med. Chem. 330, 63 (1997).

The following abbreviations are used in the text: 9-BBN for 9-borabicyclo[3.3.1]nonane, DBU for 1,8-diazabicyclo[5.4.0]undec-7-ene, DCM for dichloromethane, DMAP for 4-dimethylaminopyridine, DMF for N,N-dimethylformamide, DMSO for dimethyl sulfoxide, EDC.HCl for 1-(3-dimethylaminopropyl)-3-ethylcarbodiimide hydrochloride, EtOAc for ethyl acetate, EtOH for ethanol, KO$^t$Bu for potassium tert-butoxide, NaOtBu for sodium tert-butoxide, MeOH for methanol, TEA for triethylamine, MeCN for acetonitrile, BOC for di-tert-butyl-dicarbonate and THF for tetrahydrofuran, TOTF for o-tolyl triphenylphosphine, and HOBt for 1-hydroxy benzotriazole hydrate.

In order that the invention may be more fully understood the following examples are given by way of illustration only. In the structures shown herein, the pendent oxygens shown as —O are meant to include hydroxyl substitutions (i.e., —OH).

All references in this application are herein incorporated by reference in their entireties.

EXAMPLES

2'-O-Acetyl-6-O methyl-erythromycin A may be prepared by the procedure described by W. R. Baker et al. in *J. Org. Chem.* 1988, 53, 2340, 2'-O-acetyl-azithromycin and 2'-O-acetyl-azithromycin-11,12-carbonate may be prepared by the procedures described by S. Djokic et al. in *J. Chem. Res. (S)* 1988, 152 and 11-O-methyl-azithromycin may be prepared by the procedure described by G. Kobrehel et al. in J. Antibiotics 45; 1992, 527-532. 9(E)-Ethoxyimino-erythromycin A may be prepared by the procedures described in EP 1 167 375. 6-O-Ethyl erythromycin A, 6-O-propyl erythromycin A and 9-(1-isopropoxycyclohexyl)oximino erythromycin A may be prepared by procedure described in U.S. Pat. No. 4,990,602 and *Bioorg. Med. Chem. Lett.* 2000, 10, 815-819. 1-Cyclopropyl-6-iodo-4-oxo-1,4-dihydro-qunoline-3-carboxylic acid ethyl ester, 7-chloro-1-isopropyl-6-fluoro-4-oxo-1,4-dihydro-qunoline-3-carboxylic acid, 7-chloro-1-tert-butyl-6-fluoro-4-oxo-1,4-dihydro-qunoline-3-carboxylic acid, 1-dimethylamino-6-iodo-4-oxo-1,4-dihydro-qunoline-3-carboxylic acid may be prepared according to the procedure described in *J. Med. Chem.* 1995, 38, 973. 1-Ethyl-6-iodo-4-oxo-1,4-dihydro-qunoline-3-carboxylic acid ethyl ester my be prepared by procedure described in *Aust. J. Chem.*, 1973, 26, 907.

Intermediate 1:

7-{2-[2-(2-Carboxy-ethoxy)-ethoxy]-ethylamino}-1,2,3,6-tetrahydro-6-oxo-[1,3]-oxazino-[3,2a]-quinoline-5-carboxylic acid

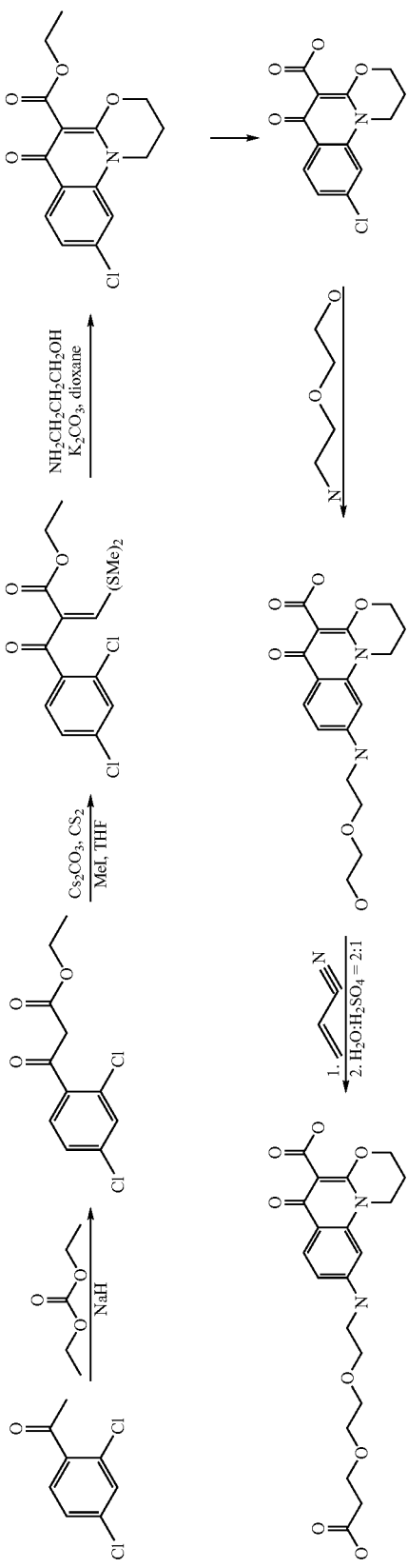

a) 3-(2,4-Dichlorophenyl)-3-oxo-propionic acid ethyl ester

Synthesis of Intermediate 1a was done by standard procedure starting from 2,4-dichloroacetophenone, diethylcarbonate (25 eq) and NaH (2 eq) at 80° C. for 60 minutes.
MS (ES+) m/z: [MH]$^+$=262 b) 2-[Bis(methylthio)methylene]-3-(2,4-dichlorophenyl)-3-oxo-propionic acid ethyl ester To a mixture of Intermediate 1a (15.7 g) and Cs$_2$CO$_3$ (2.5 eq) in THF (230 mL) CS$_2$ (4.6 eq) was added with stirring at −10° C. After 5 minutes, a single portion of CH$_3$I (2.5 eq) was added and the reaction was stirred at room temperature overnight. The reaction was diluted with ether (50 mL) and filtered. Filtrate was concentrated in vacuo.
MS (ES+) m/z: [MH]$^+$=366 c) 7-Chloro-1,2,3,6-tetrahydro-6-oxo-[1,3]oxazino[3,2a]quinoline-5-carboxylic acid ethyl ester A mixture of Intermediate 1b (18.08 g), 3-amino-1-propanole (1.2 eq) and K$_2$CO$_3$ (2.4 eq) was stirred) in dioxane (500 mL) at room temperature for 1 hour and refluxed overnight. The reaction mixture was filtered and the resulting filtrate was concentrated to dryness under reduced pressure. The crude product was precipitated from MeOH affording the title compound (2.6 g).
MS (ES+) m/z: [MH]$^+$=308 d) 7-Chloro-1,2,3,6-tetrahydro-6-oxo-[1,3]oxazino[3,2a]quinoline-5-carboxylic acid To a solution of Intermediate 1c (1.4 g) in THF (15 mL), a solution of NaOH (4.6 eq) in water (15 mL) was added and the reaction mixture was stirred at 80° C. overnight. THF was evaporated, HCl (0.6 M) was added to reach pH value of about 4 and extracted with 3×10 mL of DCM. The organic layers were washed with brine, dried over Na$_2$SO$_4$, filtered and DCM was evaporated under reduced pressure affording the title compound (1.16 g).
MS (ES+) m/z: [MH]$^+$=280 e) 7-[2-(2-Hydroxy-ethoxy)-ethylamino]-1,2,3,6-tetrahydro-6-oxo-[1,3]oxazino[3,2a]-quinoline-5-carboxylic acid Intermediate 1d (1 g) was diluted in 5 mL of methylpyrrolidone, 1.8 mL (5 eq) of 2-(2-aminoethoxy)ethanol was added and stirred at 110° C. for 24 hours. EtOAc was added to the reaction mixture; the pH was adjusted to 6 and the resultant was extracted with 3×15 mL of H$_2$O. The organic layers were washed with brine, dried over Na$_2$SO$_4$, filtered and EtOAc was evaporated under reduced pressure affording the title compound (600 mg).
MS (ES+) m/z: [MH]$^+$=349 f) 7-{2-[2-(2-Carboxy-ethoxy)-ethoxy]-ethylamino}-1,2,3,6-tetrahydro-6-oxo-[1,3]-oxazino-[3,2a]-quinoline-5-carboxylic acid Intermediate 1e (600 mg) was diluted in 7.4 mL of C$_3$H$_3$N, 0.515 mL of DBU was added and the mixture was stirred at 80° C. for 24 hours. C$_3$H$_3$N was evaporated under reduced pressure, residue dissolved in EtOAc and the pH was adjusted to 3 and extracted with 3×15 mL of H$_2$O. EtOAc was evaporated under reduced pressure affording 650 mg of cyano derivative. The cyano derivative was dissolved in 40 mL of H$_2$O/H$_2$SO$_4$ (2:1) and stirred for 24 h at 75° C. affording the title compound.
MS (ES+) m/z: [MH]$^+$=421

Intermediate 2

1-Cyclopropyl-6-fluoro-7-chloro-4-oxo-1,4-dihydroquinoline-3-(2-nitroacetyl)

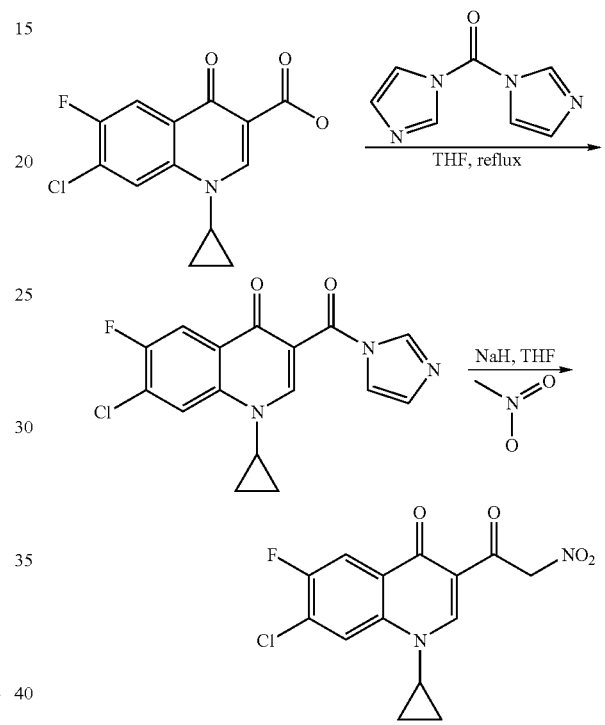

A mixture of 7-chloro-1-cyclopropyl-6-fluoro-4-oxo-1,4-dihydro-quinoline-3-carboxylic acid (1 g, 3.55 mmol) and 1,1-carbonyldiimidazole (2.88 g, 17.75 mmol) in 15 ml CCl$_3$ was heated to reflux and refluxed over night. The mixture was cooled and the solvent was removed under reduced pressure. A small amount of diethyl ether was added to the residue and the resulting solid was collected by filtration and washed with diethyl ether to give an imidazolide intermediate in a quantitative yield.

To the mixture of NaH (0.26 g, 0.0108 mol, 60% disperse oil) and nitromethane (0.58 m,1 0.0108 mol) in 20 ml of anhydrous THF a solution of imidazolide intermediate (0.9 g, 0.289 mmol) in 20 ml of anhydrous THF was added dropwise and heated to reflux for 18 h. The mixture was cooled and 20 ml of H$_2$O was slowly added and neutralized by HCl, and then extracted with CH$_2$Cl$_2$. The organic layer was washed with H$_2$O and brine, dried by anhydrous Na$_2$SO$_4$ and evaporated. The product was precipitated and filtrated off yielding 0.4 g of title compound. (90.6% pure compound according to LC-MS).
MS (ES+) m/z: [MH]$^+$=325.1

Intermediate 3

1-Cyclopropyl-6,7-difluoro-8-methoxy-4-oxo-1,4-dihydro-quinoline-3-(2-nitroacetyl)

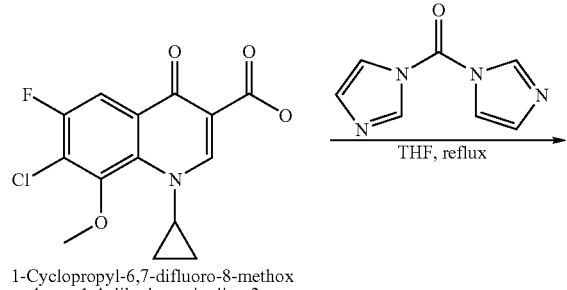

1-Cyclopropyl-6,7-difluoro-8-methoxy-4-oxo-1,4-dihydro-quinoline-3-carboxylic acid

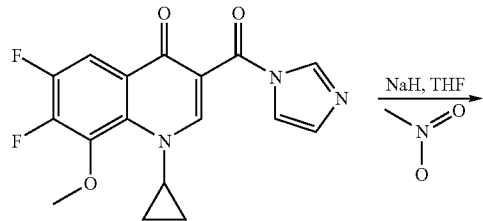

1-Cyclopropyl-6,7-difluoro-3-(imidazole-1-carbonyl)-8-methoxy-1H-quinolin-4-one

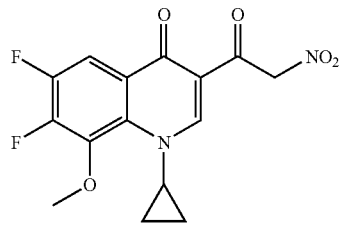

1-Cyclopropyl-6,7-difluoro-8-methoxy-4-oxo-1,4-dihydro-quinoline-3-(2-nitroacetyl)

A mixture of 1-cyclopropyl-6,7-difluoro-8-methoxy-4-oxo-1,4-dihydro-quinoline-3-carboxylic acid (1 g, 3.38 mmol) and 1,1-carbonyldiimidazole (2.19 g, 13.54 mmol) in 15 ml CCl₃ was heated to reflux and refluxed overnight. The mixture was cooled and the solvent was removed under reduced pressure. To the residue a small amount of diethyl ether was added and the resulting solid was collected by filtration and washed with diethyl ether to give an imidazolide intermediate in a quantitative yield.

To the mixture of NaH (0.28 g, 0.0116 mmol, 60% disperse oil) and nitromethane (0.62 ml, 0.01158 mol) in 20 ml of anhydrous THF, a solution of imidazolide intermediate (1 g, 2.89 mmol) in 20 ml of anhydrous THF was added dropwise and heated to reflux for 18 h. The mixture was cooled and 20 ml of H₂O was slowly added and neutralized by HCl, and then extracted with CH₂Cl₂. The organic layer was washed with H₂O and brine, dried by anhydrous Na₂SO₄ and evaporated. The product was precipitated and filtrated off yielding 0.56 g of title product. (93.46% pure compound according to LC-MS).

MS (ES+) m/z: [MH]⁺=339.1

Intermediate 4

7-[2-(2-Cyano-ethoxy)-ethylamino]-1-cyclopropyl-6-fluoro-8-methoxy-4-oxo-1,4-dihydro-quinoline-3-(2-nitroacetyl)

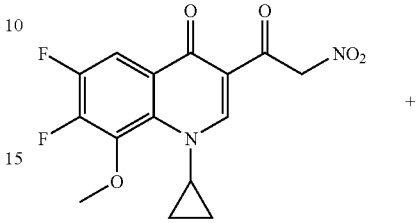

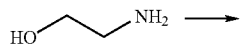

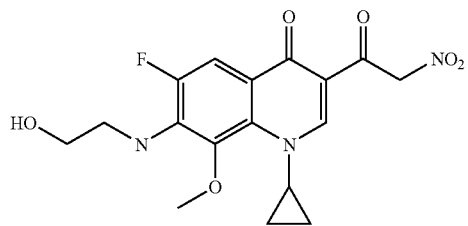

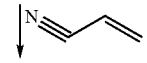

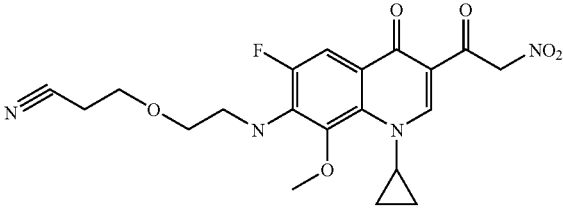

To a solution of Intermediate 3 (250 mg) in DMSO (15 ml) ethanolamine (0.425 ml) was added and the reaction mixture was stirred at 90° C. for 1.5 hours. pH Value of mixture was adjusted to 4.5 and product was precipitated. After filtration, 190 mg of 1-cyclopropyl-6-fluoro-7-(2-hydroxy-ethylamino)-8-methoxy-4-oxo-1,4-dihydro-quinoline-3-(2-nitroacetyl) was obtained. A solution of 1-cyclopropyl-6-fluoro-7-(2-hydroxy-ethylamino)-8-methoxy-4-oxo-1,4-dihydro-quinoline-3-(2-nitroacetyl) (180 mg) in acrylonitrile and DBU was stirred at 80° C. under N₂ for 5 hours. CH₃CN was evaporated under reduced pressure yielding oily title product.

Intermediate 5

6-[3-piperazin-1-yl)-propyl]-1-ethyl-4-oxo-1,4-dihydro-quinoline-3-carboxylic acid ethyl ester

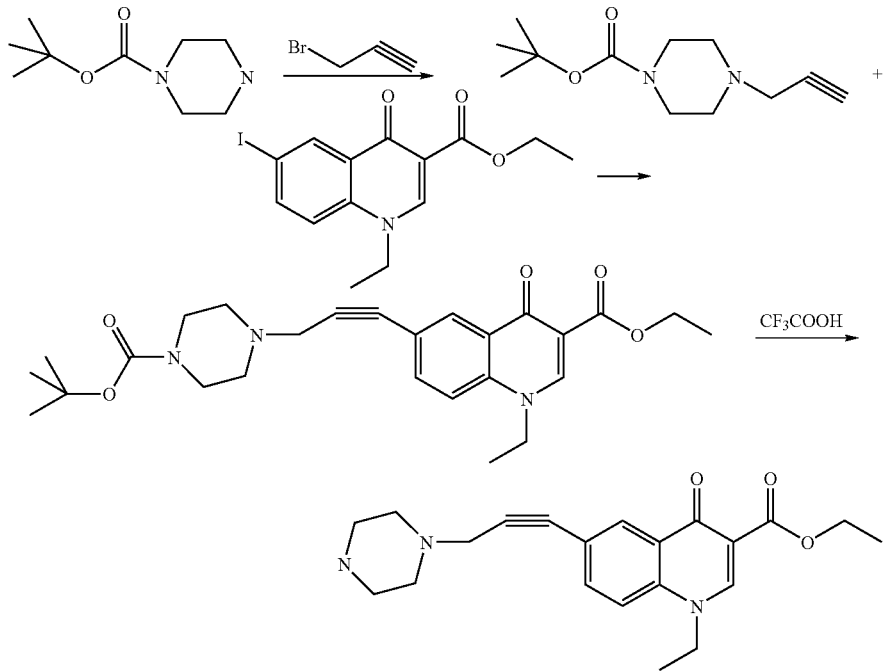

a) 4-Prop-2-ynyl-piperazine-1-carboxylic acid tert-butyl ester

To the degassed solution of piperazine-1-carboxylic acid tert-butyl ester (1.0 g, 5.37 mmol) in acetonitrile (10 ml) were added $Na_2CO_3$ (1.708 g, 16.11 mmol) and mixture was stirred for 20 min. The suspension was heated to 50° C. and 3-bromo-propyne (0.9 mL, 8.055 mmol) was added. The solvent was evaporated and the residue was extracted with Et-Ac and water (2×50 mL). Organic layer was washed with NaCl and $NaHCO_3$ (2×50 ml). The organic layer was dried over $K_2CO_3$ and evaporated in vacuum yielding (0.70 g) oil title intermediate.

MS (ES+) m/z: $[MH]^+$=225.1 b) 6-[3-(4-tert-Butoxycarbinyl-piperazin-1-yl)-prop-1-ynyl]-1-ethyl-4-oxo-1,4-dihydro-quinoline-3-carboxylic acid ethyl ester 1-Ethyl-6-iodo-4-oxo-1,4-dihydro-quinoline-3-carboxylic acid ethyl ester (0.7 g, 3.125 mmol), copper (I) iodide (42.47 mg, 0.223 mmol) and triethylamine (10.809 mL, 78.05 mmol) were suspended in dry acetonitrile (20 ml). The suspension was heated to 50° C. and $N_2$ bubbled through. After 20 min, dichlorobis(triphenylposphine)palladium (II) (46.96 mg, 0.0669 mmol) and Intermediate 5a (0.7 g 3.125 mmol) were added and dark red suspension was heated at 50° C. for 3 hours. The solvent was evaporated and the residue was extracted with EtOAc and water (2×50 mL). Organic layer was washed with NaCl and NaHCO3 (2×50 mL), dried over $K_2CO_3$ and evaporated in vacuum yielding (1.24 g) oil red title product.

MS (ES+) m/z: $[MH]^+$=468.3 c) 6-[3-piperazin-1-yl)-propyl]-1-ethyl-4-oxo-1,4-dihydro-quinoline-3-carboxylic acid ethyl ester To the solution of Intermediate 5b (1.2 g, 2.57 mmol) in DCM (1.2 mL) was added $CF_3COOH$ (1.2 mL) and mixture was stirred at room temperature for 48 h. To the reaction mixture was added water (pH=1.2) and layers were separated (pH=9.6). The organic layer was dried over $K_2CO_3$ and evaporated in vacuum yielding (1.7 g) oil red title product.

MS (ES+) m/z: $[MH]^+$=368.3

Intermediate 6

1-Cyclopropyl-6-fluoro-7-[2-(2-hydroxy-ethoxy)-ethylamino]-4-oxo-1,4-dihydro-quinoline-3-carboxylic acid (A) and 7-Chloro-1-cyclopropyl-6-[2-(2-hydroxy-ethoxy)-ethyl amino]-4-oxo-1,4-dihydro-quinoline-3-carboxylic acid (B)

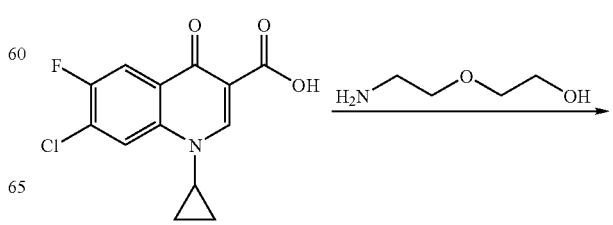

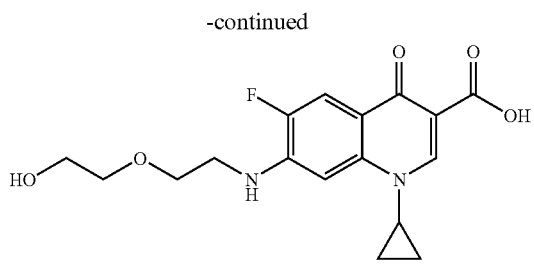

+

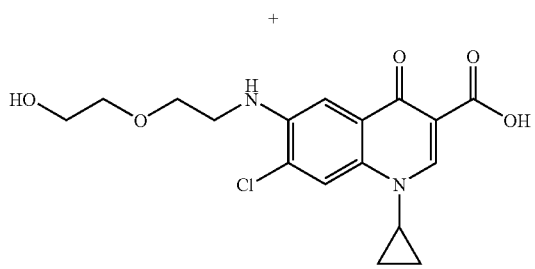

To a mixture of 7-chloro-1-cyclopropyl-6-fluoro-4-oxo-1,4-dihydro-quinoline-3-carboxylic acid (10 g, 0.035 mol) in 1-methyl-2-pirolidone (70 mL) 2-(2-amino-ethoxy)-ethanol (18 mL, 0.18 mol, 5 eq.) was added, the reaction mixture was stirred at 110° C. for 24 hours. Then was diluted with water (200 mL) and CH$_2$Cl$_2$ (60 mL) and the pH was adjusted to 10. The aqueous layer was extracted with CH$_2$Cl$_2$ (5×50 mL) and then the pH was adjusted to 6.7. After 10 minutes first product precipitated. Filtrated off yielding 2.7 g of crude 7-chloro-1-cyclopropyl-6-[2-(2-hydroxy-ethoxy)-ethylamino]-4-oxo-1,4-dihydro-quinoline-3-carboxylic acid. (according to LC-MS 100% pure Intermediate 6B) Over night second product precipitated. Filtrated off yielding 7.7 g of yellow product (according to LC-MS a mixture of Intermediate 6A and Intermediate 6B in a 1:1 ratio).

Intermediate 7

6-{2-[2-(2-carboxy-ethoxy)ethoxy]ethylamino}-1-cyclopropyl-7-chloro-4-oxo-1,4-dihydro-quinoline-3-carboxylic acid

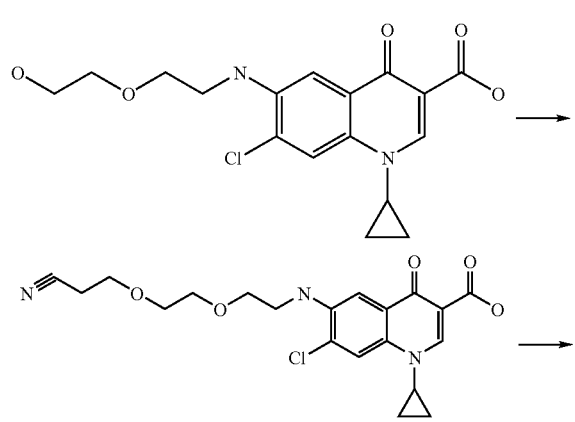

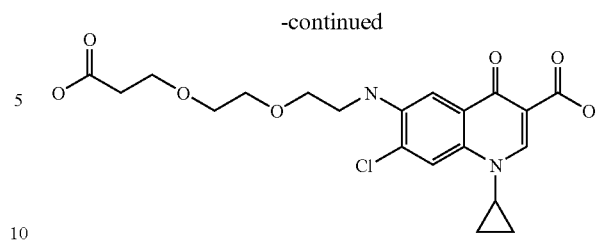

Intermediate 6B (2 g, 5.45 mmol) was diluted in 25 mL of acrylonitrile, DBU (2.0 mL) was added and stirred at 80° C. for 24 hours. Acrylonitrile was evaporated under reduced pressure, residue was dissolved in DCM and the pH was adjusted to pH 3 and extracted with 3×20 mL H$_2$O. The organic layers were washed with brine, dried over Na$_2$SO$_4$, filtered and DCM was evaporated under reduced pressure affording 1.9 g of 6-{2-[2-(2-cyano-ethoxy)ethoxy]ethylamino}-1-cyclopropyl-7-chloro-4-oxo-1,4-dihydro-quinoline-3-carboxylic acid. This product was dissolved in 40 mL of mixture H$_2$O/H$_2$SO$_4$ (1:1) and stirred for 24 hours at 75° C. The obtained precipitate was filtered and dried under reduced pressure for 1 h affording 1.7 g of title product.

Intermediate 8

1-Cyclopropyl-6-fluoro-7-chloro-4-oxo-1,4-dihydro-3-[(2-methanesulfonyl)acetyl]-quinoline

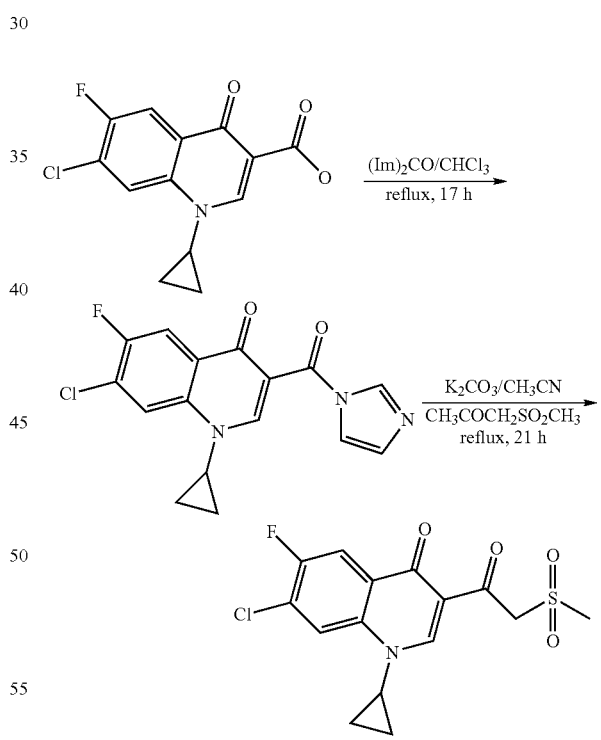

A mixture of 1-cyclopropyl-6-fluoro-7-chloro-4-oxo-1,4-dihydro-quinoline-3-carboxylic acid (2 g, 0.0071 mol) and 1,1'-carbonyldiimidazole (5.76 g, 0.035 mol) in 15 mL CHCl$_3$ was heated to reflux for 17 hours. The solvent was removed by reduced pressure. To the residue ether was added and then stirred at room temperature for 30 min. The solid was filtered and dried affording 1.64 g of 3-imidazolide derivative. Imidazolide derivative (1 g, 0.003 mol) was dissolved in 40 mL acetonitrile, then methanesulphonylacetone (2 g, 0.015 mol) and K$_2$CO$_3$ were added and the mixture was heated to reflux for 21 hours. The solvent was removed under reduced pressure and 120 mL of H$_2$O was added. The solution was acidified by 2N HCl (pH ~3) and extracted with EtOAc. The organic layer was dried and concentrated to give a crude solid product. The crude product was purified by column chromatography (DCM-EtOH—NH$_4$OH=90:9:1.5) to give pure product 1-cyclopropyl-6-fluoro-7-chloro-4-oxo-1,4-dihydro-3-[(2-methanesulfonyl)acetyl]-quinoline.

MS (ES+) m/z: [MH]$^+$=358.1.

Intermediate 9

9-(2-hydroxy-ethylamino)-1-oxo-6,7-dihydro-1H,5H-pyrido[3,2,1-ij]quinoline-2-carboxylic acid b) 9-(Benzhydrylidene-amino)-1-oxo-6,7-dihydro-1H,5H-pyrido[3,2,1-ij]quinoline-2-carboxylic acid ethyl ester Tris(dibenzylideneacetone)dipalladium chloroform complex (50 mg, 0.05 mmol), rac-2,2'-bis(diphenylphosphino)-1,1'-binaphthyl (100 mg, 0.16 mmol), Intermediate 9a (3 g, 8.9 mmol) and benzophenone imine (1.2 ml) were diluted in THF (45 ml). The air of atmosphere was replaced with N$_2$, and Cs$_2$CO$_3$ (2.5 g) was added. The mixture was stirred under reflux. Another two portions of Tris(dibenzylideneacetone)dipalladium chloroform complex (50 mg, 0.05 mmol), rac-2, 2'-bis(diphenylphosphino)-1,1'-binaphthyl (100 mg, 0.16 mmol), benzophenone imine (1.2 ml) and Cs$_2$CO$_3$ (2.5 g) was added every 2.5 h. The mixture was stirred under reflux over

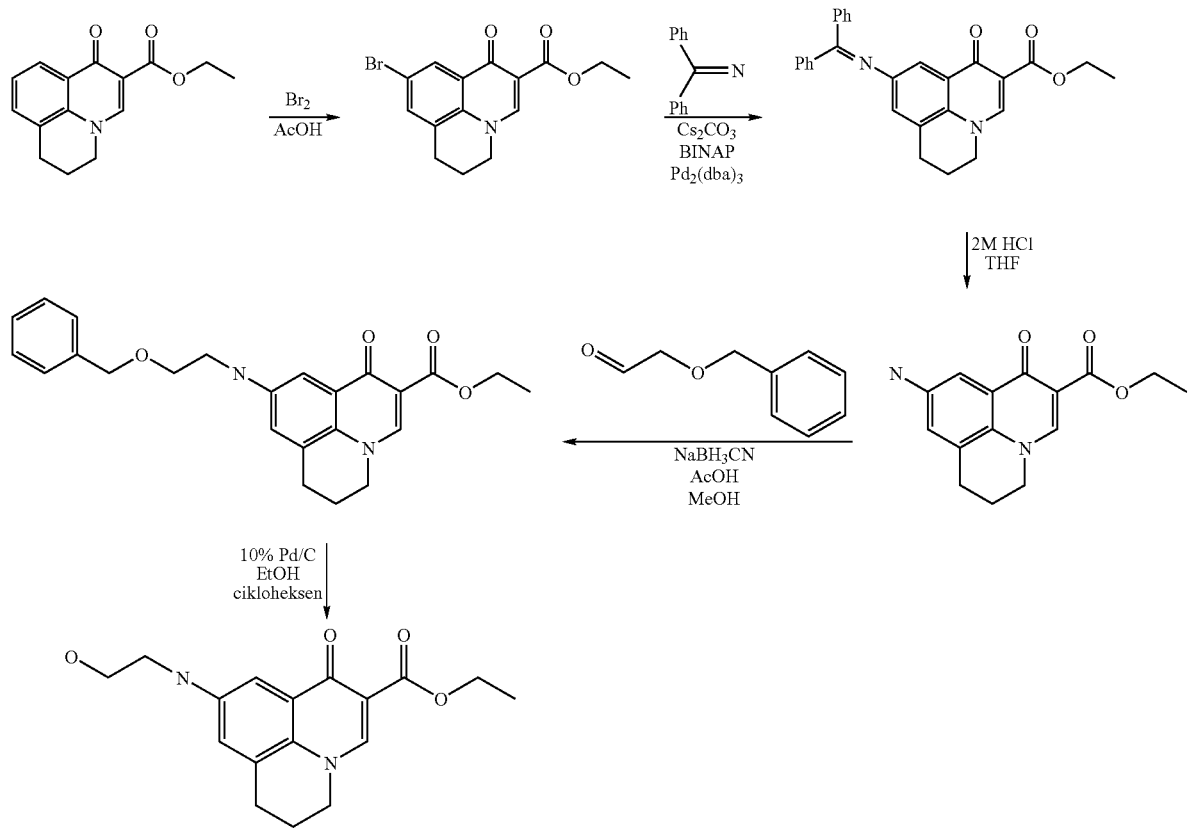

a) 9-Bromo-1-oxo-6,7-dihydro-1H,5H-pyrido[3,2,1-ij]quinoline-2-carboxylic acid ethyl ester To the solution of 1-Oxo-6,7-dihydro-1H,5H-pyrido[3,2,1-ij]quinoline-2-carboxylic acid ethyl ester (7.5 g, 29 mmol) in glacial acetic acid (120 mL) was added bromine (1.6 ml, 32 mmol). The mixture was stirred over night at room temperature, and new portion of bromine (1.6 mL, 32 mmol) was added. After 24 h, reaction mixture was diluted with 100 mL of H$_2$O and pH was adjusted to 2.9. Precipitate was filtered and dried. The crude product was precipitated from CH$_2$Cl$_2$/Diisoprophylether and dried in vacuum drier yielding 13.07 g of the crude title product.

MS (ES+) m/z: [MH]$^+$=338.0.

night and then cooled to room temperature and filtered. HPLC/MS indicated the presents of product 9b.

MS (ES+) m/z: [MH]$^+$=437.3.

c) 9-Amino-1-oxo-6,7-dihydro-1H,5H-pyrido[3,2,1-ij]quinoline-2-carboxylic acid ethyl ester To the mixture of Intermediate 9b 5% HCl was added dropwise until appearance of precipitate. Precipitate was filtered and dried in vacuum drier yielding 2 g of the crude title product.

MS (ES+) m/z: [MH]$^+$=273.2 $^{13}$C-NMR(125 MHz, DMSO) δ: 13.81, 19.90, 25.57, 51.37, 59.24, 108.39, 115.66, 124.99, 128.06, 129.06, 129.91, 130.51, 133.95, 147.54, 163.98, 171.63.

d) 9-(2-Benzyloxy-ethylamino)-1-oxo-6,7-dihydro-1H,5H-pyrido[3,2,1-ij]quinoline-2-carboxylic acid ethyl ester To the solution of Intermediate 9c (200 mg, 0.73 mmol) in MeOH (75 mL), benzyloxyacetaldehyde (110 mg, 0.73 mmol), NaBH$_3$CN (137 mg, 2.2 mmol) and AcOH (250 µl) was added. Reaction mixture was stirred for 20 minutes and evaporated in vacuum. Oil product was purified by column chromatography in system CH$_2$Cl$_2$-(MeOH—NH$_4$OH=9:1.5)=9:(1.5) yielding 159 mg of the title product.

MS (ES+) m/z: [MH]$^+$=407.2.

e) 9-(2-hydroxy-ethylamino)-1-oxo-6,7-dihydro-1H,5H-pyrido[3,2,1-ij]quinoline-2-carboxylic acid To the solution of Intermediate 9d (159 mg, 0.39 mmol) in EtOH (41.6 mL) cyclohexene (12.8 mL) and 10% Pd/C (243 mg) were added. The mixture was stirred under reflux over night, filtered through celite and evaporated in vacuum yielding 80 mg of the title product.

Intermediate 10

6-{2-[2-(2-Carboxy-ethoxy)-ethoxy]-ethoxy}-7-chloro-1-cyclopropyl-4-oxo-1,4-dihydro-quinolone-3-carboxylic acid Mixture of 50 mL diethylene glycole and 50 mL DMSO was prepared and heated on 70° C. Into mixture 8 g of KO-t-Bu portionwise was added. Then, 5 g of fluoro-chloro quinolonic acid (17.8 mmol) was added portionwise. The temperature was increased to 105° C. After 5 hours, the 25 mL of H$_2$O was added and the mixture was extracted with 2×20 mL of DCM. Water layer was adjusted to pH 4. The obtained precipitate was filtered off and dried under reduced pressure affording 500 mg of 7-chloro-1-cyclopropyl-6-[2-(2-hydroxy-ethoxy)-ethoxy]-4-oxo-1,4-dihydro-quinolone-3-carboxylic acid.

7-Chloro-1-cyclopropyl-6-[2-(2-hydroxy-ethoxy)-ethoxy]-4-oxo-1,4-dihydro-quinolone-3-carboxylic acid (500 mg) was dissolved in 12.5 mL of acrylonitrile, then 1 mL of DBU was added and the mixture was stirred for 24 hours at 80° C. Acrylonitrile was evaporated under reduced pressure, residue was dissolved in 300 mL of 2-propanol and the pH of the mixture was adjusted to pH 3.5. The precipitate was obtained after 12 hours, filtered off and washed with water (pH 3.5). The precipitate was dissolved in 20 mL H$_2$O:H$_2$SO$_4$ (1:1) and stirred for 24 hours at room temperature. The obtained precipitate was filtered off and dried under reduced pressure affording 300 mg of the title Intermediate 11

6-{2-[2-(2-amino-ethoxy)-ethoxy]-ethylamino}-1-cyclopropyl-7-chloro-4-oxo-1,4-dihydro-quinoline-3-carboxylic acid (A) and 7-{2-[2-(2-amino-ethoxy)-ethoxy]-ethylamino}-1-cyclopropyl-6-fluoro-4-oxo-1,4-dihydro-quinoline-3-carboxylic acid (B)

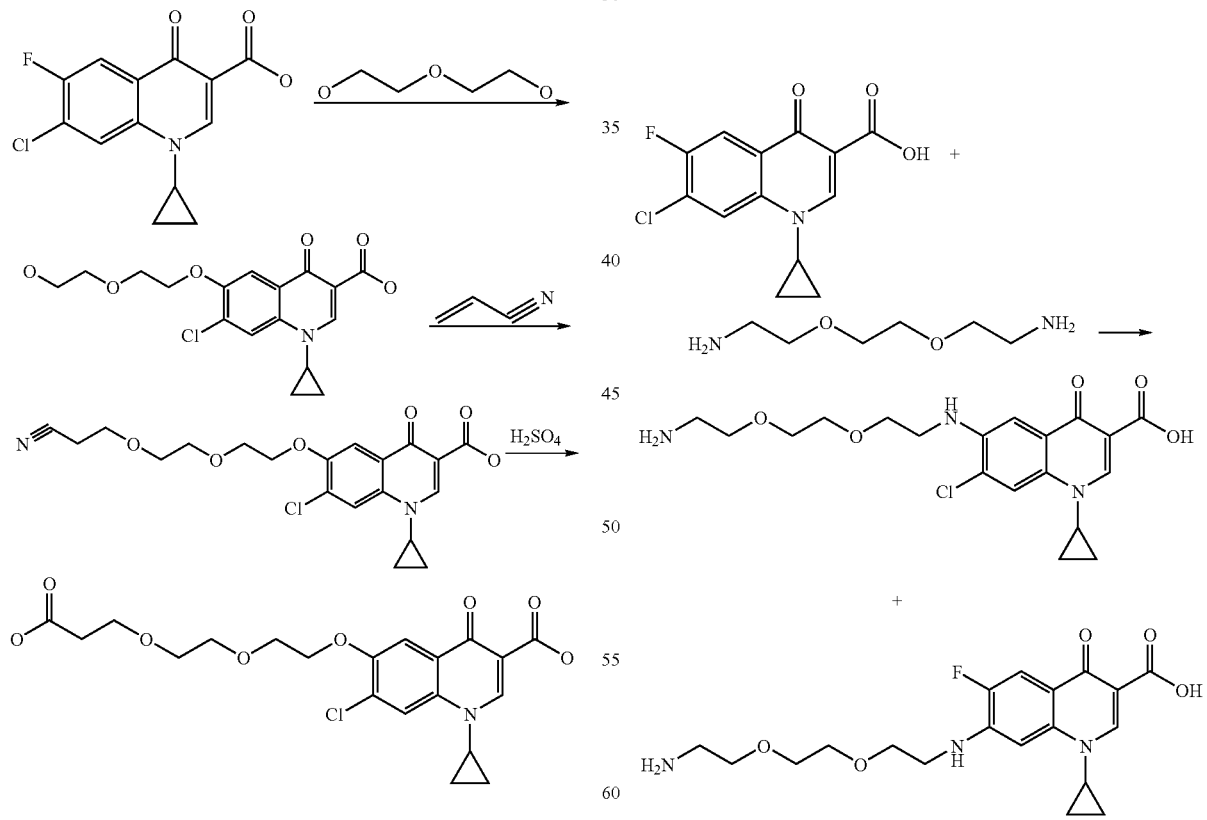

-continued

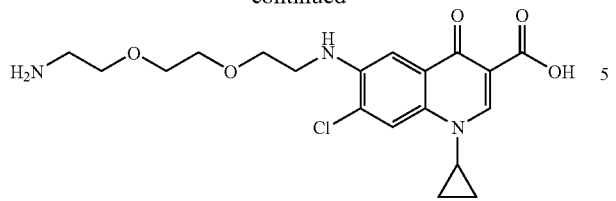

A mixture of 7-chloro-1-cyclopropyl-6-fluoro-4-oxo-1,4-dihydro-quinoline-3-carboxylic acid (5 g, 0.018 mol), 2,2'-(ethylenedioxy)bis-(ethylamine) (26 mL, 0.18 mol, 10 eq.) in 1-methyl-2-pyrrolidone was heated at 110° C. for 24 hours. Reaction mixture was diluted with water (70 mL) pH was adjusted to 11 and extracted with $CH_2Cl_2$ (9×40 mL). Water layer was then acified to pH 6.8 with $H_2SO_4$, extracted with $CH_2Cl_2$ (50 mL) and evaporated. 2-Propanol was added (200 mL) and stirred at 82° C. for 30 minutes. The reaction mixture was then filtered and 2-propanol was evaporated in vacuum yielding 8 g of oily product, according to LC-MS 50% of chloro derivative (A) and 30% of fluoro derivative. Product was purified by column chromatography (eluent $CH_2Cl_2$-2-propanol=1:1) yielding pure chloro derivative (A).

MS (ES+) m/z: $[MH]^+$=409.9 (A) MS (ES+) m/z: $[MH]^+$=393.4 (B).

Intermediate 12

1-Oxo-9-(3-piperazin-1-yl)-prop-1-ynyl)-6,7-dihydro-1H,5H-pyrido[3,2,1-ij]quinoline-2-carboxylic acid ethyl ester a) 4-Prop-2-ynyl-piperazine-1-carboxylic acid tert-butyl ester To the degassed solution of piperazine-1-carboxylic acid tert-butyl ester (0.5 g, 2.69 mmol) in acetonitrile (5 mL) was added $Na_2CO_3$ (0.854 g, 8.05 mmol) and mixture was stirred for 20 min. The suspension was heated to 50° C. and 3-bromo-propyne (448.65 µl, 4.03 mmol) was added. The solvent was evaporated and the residue was extracted with EtOAc and water. Organic layer was washed with NaCl and $NaHCO_3$ (2×20 ml), dried over $K_2CO_3$ and evaporated in vacuum yielding 0.45 g of the title product as yellowish oil.

MS (ES+) m/z: $[MH]^+$=247.2.

b) 9-[3-(4-tert-Butoxycarbinyl-piperazin-1-yl)-prop-1-ynyl]-1-oxo-6,7-dihydro-1H,5H-pyrido[3,2,1-ij]quinoline-2-carboxylic acid ethyl ester Intermediate 14 (0.2 g, 0.524 mmol), copper (I) iodide (9.98 mg, 0.0524 mmol) and triethylamine (2.54 ml, 18.34 mmol) were suspended in dry acetonitrile (10 mL). The suspension was heated to 50° C. and $N_2$ bubbled through. After 20 min, dichlorobis(triphenylposphine) palladium (II) (11.03 mg, 0.0157 mmol) and Intermediate 12a (0.164 g 0.733 mmol) were added and dark red suspension was heated for 3 hours at 50° C. The solvent was evaporated and the residue was extracted with EtOAc and water (2×20 ml). Organic layer was washed with NaCl and $NaHCO_3$ (2×20 ml), dried over $K_2CO_3$ and evaporated in vacuum yielding 0.34 g of the title product as red oil.

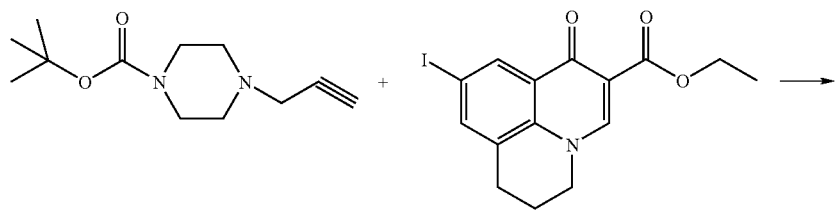

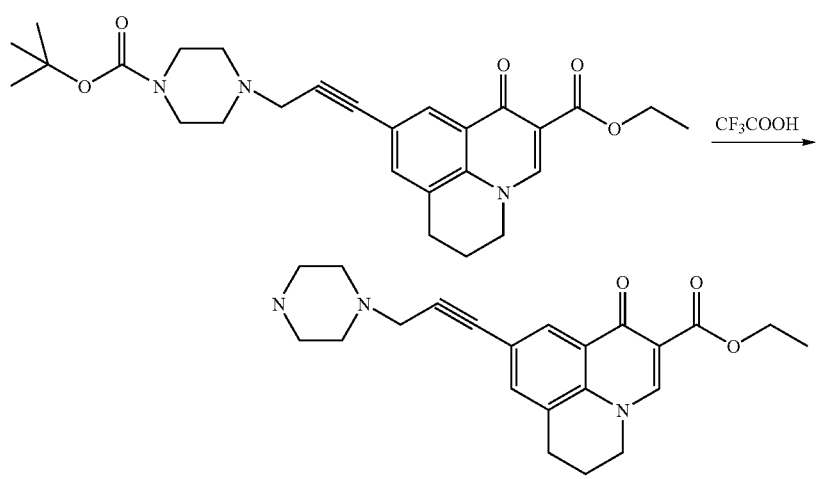

c) 1-Oxo-9-(3-piperazin-1-yl)-prop-1-ynyl)-6,7-dihydro-1H,5H-pyrido[3,2,1-ij]quinoline-2-carboxylic acid ethyl ester To the solution of Intermediate 12b (0.34 g, 0.71 mmol) in DCM (3.4 mL) was added CF$_3$COOH (3.4 mL) and mixture was stirred for 48 hours at room temp. To the reaction mixture was added water (pH 1.2) and layers were separated (pH 9.6). The organic layer was dried over K$_2$CO$_3$ and evaporated in vacuum yielding 0.22 g of the title product as red oil.

MS (ES+) m/z: [MH]$^+$=380.2.

Intermediate 13

10-Amino-1-Oxo-6,7-dihydro-1H,5H-pyrido[3,2,1-ij]quinoline-2-carboxylic acid ethyl ester

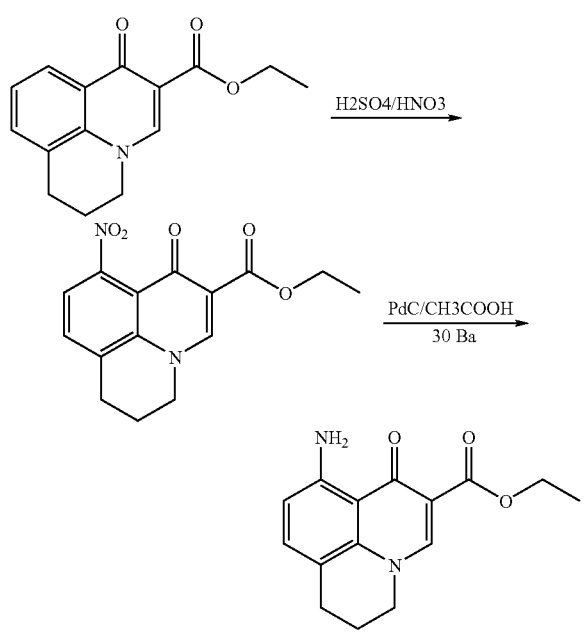

a) 10-Nitro-1-Oxo-6,7-dihydro-1H,5H-pyrido[3,2,1-ij]quinoline-2-carboxylic acid ethyl ester 1-Oxo-6,7-dihydro-1H,5H-pyrido[3,2,1-ij]quinoline-2-carboxylic acid ethyl ester (1.0 g) was placed in round bottom flask and to that, mixture of H$_2$SO$_4$/HNO$_3$ (1:1) was added and stirred for 3 hours at 0° C. The reaction mixture was poured on ice and precipitate was filtered off affording 900 mg of title product (LC/MS: 95%).

b) 10-Amino-1-Oxo-6,7-dihydro-1H,5H-pyrido[3,2,1-ij]quinoline-2-carboxylic acid ethyl ester Intermediate 13a (9oo mg) was diluted in 35 mL of acetic acid and to this mixture 800 mg of 10% Pd/C was added and stirred for 15 h at room temperature and at 30 Ba. The reaction mixture was filtered to remove catalyst and then acetic acid was evaporated under reduced pressure affording 700 mg of the title product. (LC/MS: 95%).

Intermediate 14

9-Iodo-1-oxo-6,7-dihydro-1H,5H-pyrido[3,2,1-ij]quinoline-2-carboxylic acid ethyl ester

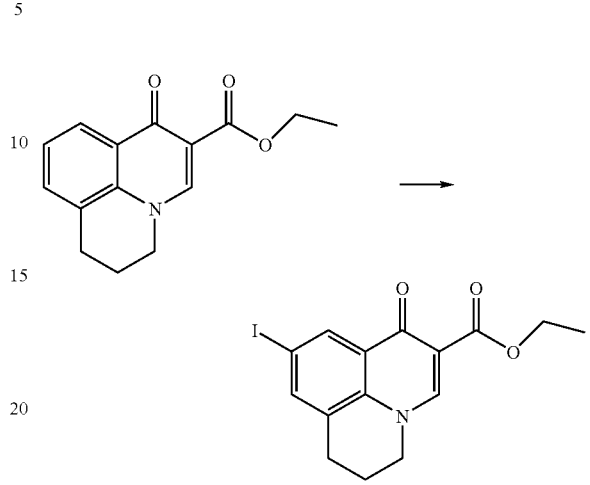

To a 0° C. cooled trifluoromethansulfonic acid (3 mL, 33.31 mmol) 1-Oxo-6,7-dihydro-1H,5H-pyrido[3,2,1-ij]quinoline-2-carboxylic acid ethyl ester (1.53 g, 5.95 mmol) was added and to that solution N-Iodosuccinimide (1.6 g, 714 mmol) was added. The mixture was allowed to warm from 0° C. to room temperature while stirring. Reaction mixture was poured in ice and precipitate was filtered off affording 1 g of the title product (LC/MS: 57%).

Intermediate 15

3-(2-tert-butoxycarbonylethyl)-imidazolidine-1-carboxylic acid tert-butyl ester

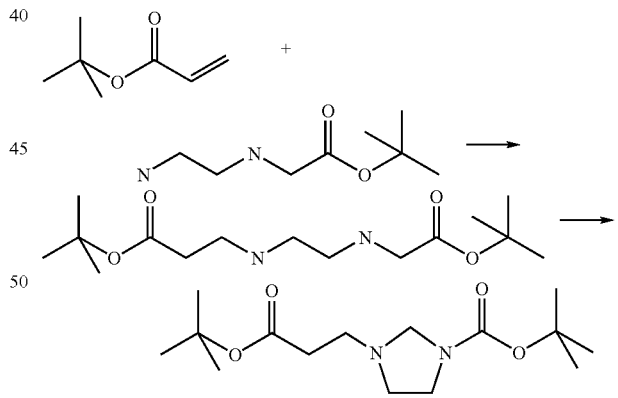

a) 3-[2-(tert-butoxycarbonylmethyl-amino)-ethylamino]-propionic acid tert-butyl ester To the solution of (2-amino-ethylamino)-acetic acid tert-butyl ester (1.0 mL, 6.32 mmol) in i-PrOH (50 mL) was added acrylic acid tert-butyl ester (309.1 μL, 2.11 mmol). The suspension was heated for 48 hours at 60° C. The solvent was evaporated and product was purificated by column chromatography (DCM-MeOH—NH$_3$=90:3:0.5) yielded the title product as colorless oil (0.45 mg)

MS (ES+) m/z: [MH]$^+$=289.2. .

b) 3-(2-tert-butoxycarbonylethyl)-imidazolidine-1-carboxylic acid tert-butyl ester To the solution of Intermediate 15a (0.45 mg, 1.56 mmol) in chloroform (20 mL) were added HCOOH (0.218 mL, 5.78 mmol) and HCHO (0.24 mL, 8.69 mmol) and stirred at room temperature for 2 hours. To the reaction mixture was added water (pH 1.3) and layers were separated (pH 2.5). The organic layer was dried over $K_2CO_3$ and evaporated in vacuum yielding 034 g of oil colorless product.

MS (ES+) m/z: $[MH]^+$=301.2.

Intermediate 16

4"-O-Allyl-2'-O-acetylazithromycin-11,12-cyclic carbonate

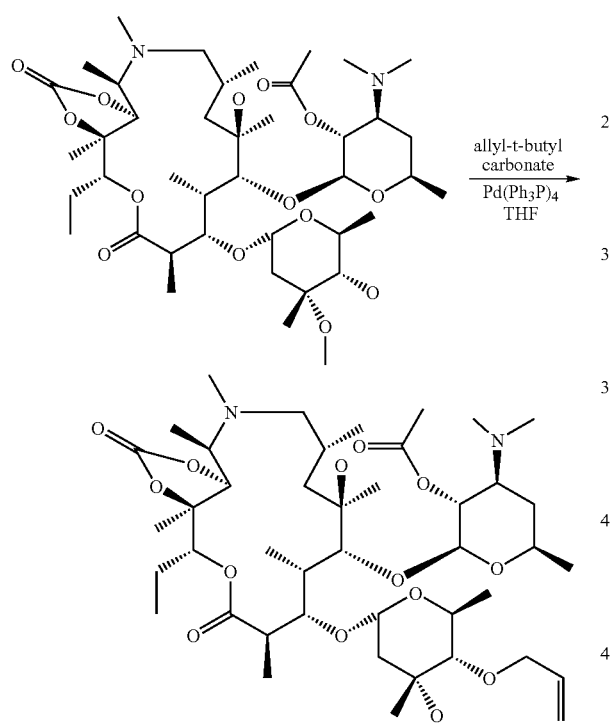

To a solution of 2'-O-acetyl azithromycin-11,12-cyclic carbonate (0.408 g, 0.5 mmol) in dry THF (4 mL) under an atmosphere of nitrogen was added tetrakistriphenylphosphine palladium (0.057 g, 0.05 mmol) and allyl t-butyl carbonate (0.30 g, 1.9 mmol). The resulting mixture was stirred under reflux. After 18 hours of reflux TLC indicated 50% conversion of the desired product. The solvent was evaporated and the crude product dissolved in 4 mL of methanol. The mixture was stirred overnight at room temperature and then concentrated under reduced pressure.

The crude product was purified by flash chromatography over silica gel eluting with the system (DCM-MeOH—aq.$NH_3$=90:9:0.5) to yield 0.24 g (56%) of a pale yellow crystals.

Intermediate 17

4"-Acetaldehyde-azithromycin 11,12-cyclic carbonate

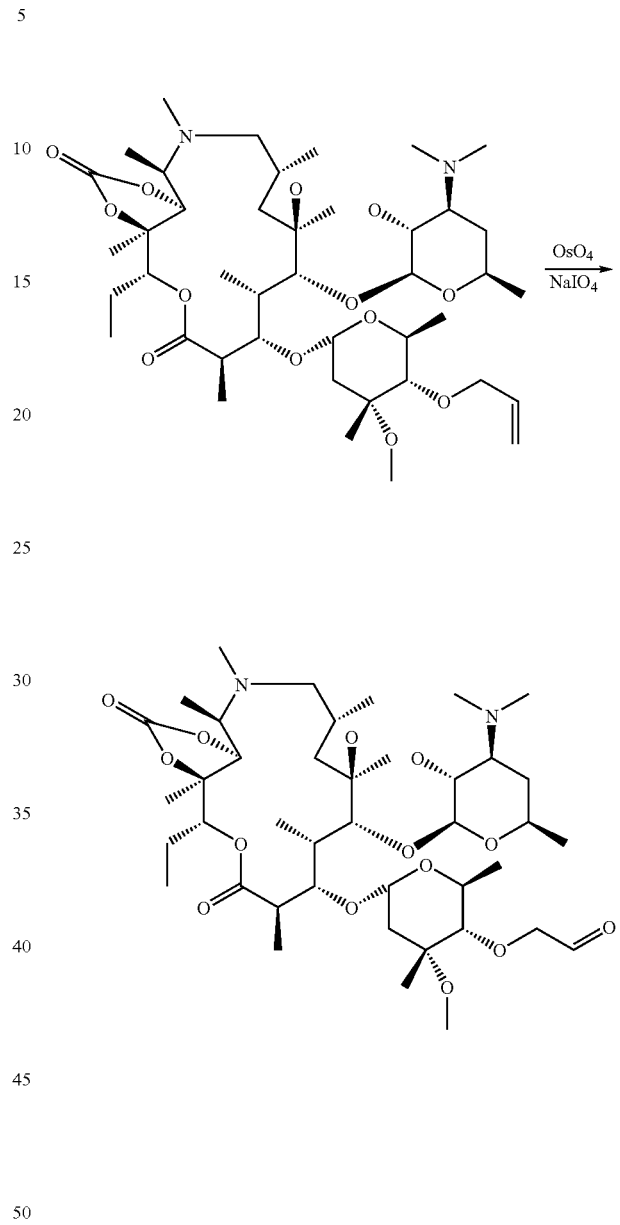

To a solution of the Intermediate 16 (0.20 g, 0.23 mmol) in THF (1 mL) and water (1 mL) was added osmium tetraoxide (2.0 mL of a 2.5% solution in THF). After stirring for 5 minutes sodium periodate (0.213 g, 1 mmol) was added in one portion. The mixture was vigorously stirred for 12 hours at 25° C. before being quenched with saturated aqueous $Na_2CO_3$ (10 mL). The resulting solution was stirred at 25° C. for 2 hours and then partitioned between EtOAc (22 mL) and water (5.0 mL). The organic phase was separated and the aqueous phase was extracted with EtOAc (2×10 mL). The combined organic extracts were dried ($K_2CO_3$), the solvent was removed under reduced pressure. Flash column chromatography ((DCM-MeOH— aq.$NH_3$=90:9:0.5) provided the corresponding aldehyde as a bright yellow solid (ca. 160 mg; 81% yield).

Intermediate 18

4''-O-(3-Methoxycarbonyl-allyl)-azithromycin 11,12-cyclic carbonate

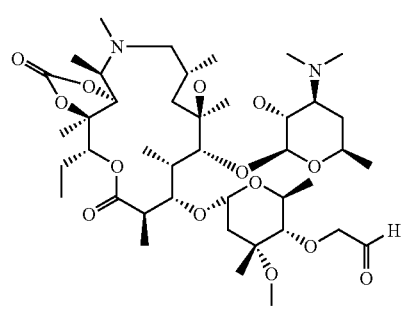

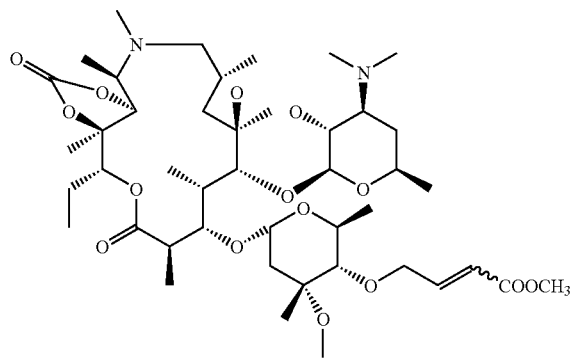

A mixture of Intermediate 17 (587.6 mg, 0.719 mmo) and stabilized ylide (360 mg, 1.08 mmol, 1.5 mol equiv.) in benzene (7.2 mL) was heated at reflux for 18 hours. After cooling to 25° C. the solvent was removed under reduced pressure. Flash column chromatography (silica gel, DCM-MeOH— aq. NH$_3$=90:9:0.5) furnished unsaturated methylester (313.8 mg, 50%) as a mixture of Z and E isomers in 1:1 ratio according LC/MS analyses.

Intermediate 19

4''-O-(3-Methoxycarbonyl-propyl)-azithromycin 11,12-cyclic carbonate

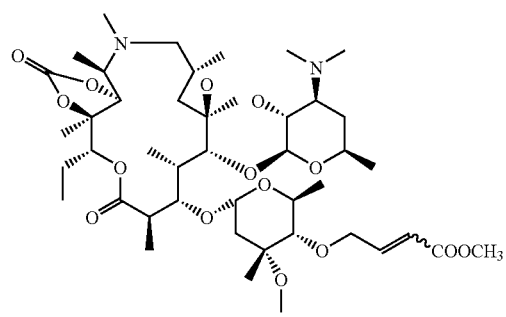

-continued

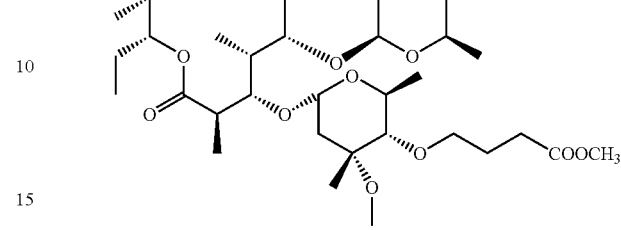

The mixture of Intermediate 18 (200 mg) was dissolved in MeOH (5 mL), treated with Pd/C (50 mg, 10% Pd) and catalytically hydrogenated in Parr apparatus for 5 ours. After filtration through a Celite pad, the filtrate was concentrated in vacuo and the residue purified by column chromatography (DCM-MeOH— aq. NH$_3$=90:9:0.5) to give 125 mg of pure title compound as a colourless crystalline solid.

Intermediate 20

4''-O-(3-Carboxy-propyl)-azithromycin

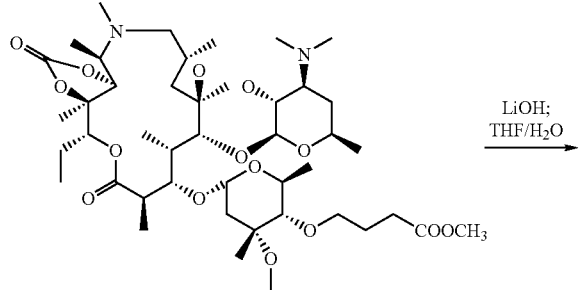

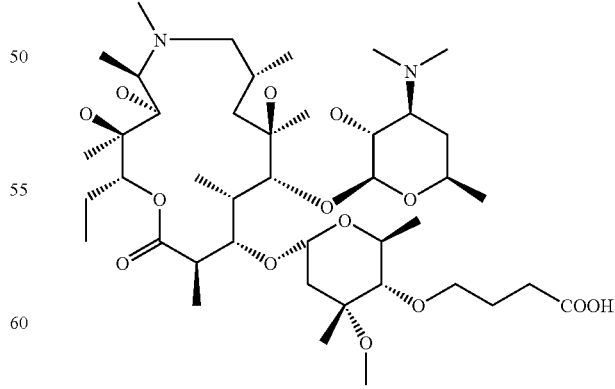

Intermediate 19 was dissolved in a mixture of THF/H$_2$O, then lithium hydroxide was added and the mixture was stirred at room temperature for 3 hours affording the title compound.

Intermediate 21

6-Amino-1-ethyl-4-oxo-1,4-dihydro-quinoline-3-carboxylic acid ethyl ester

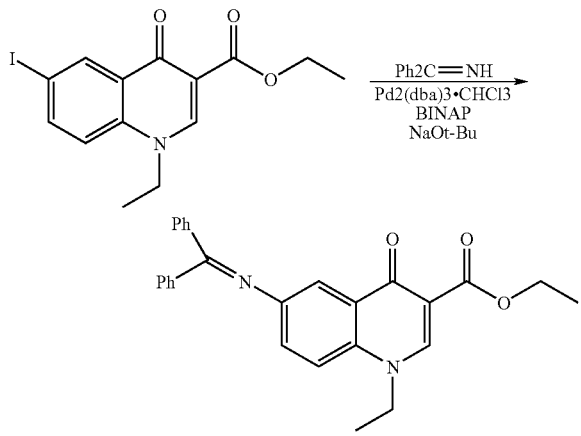

a) 6-(Benzhydrylidene-amino)-1-ethyl-4-oxo-1,4-dihydro-quinoline-3-carboxylic acid ethyl ester A Pyrex tube was charged with sodium tert-butoxide (1.4 mmol), Pd$_2$(dba)$_3$ (0.00125 mmol), and BINAP (0.00375 mmol). The Pyrex tube was fitted with a septum and after the air atmosphere was replaced with argon, toluene (4 mL), 1-ethyl-6-iodo-4-oxo-1,4-dihydro-quinoline-3-carboxylic acid ethyl ester (1.0 mmol), and benzophenone imine (1.2 mmol) were added by syringe. The reaction was sealed and heated to 80° C. with stirring until starting material was consumed as judged by GC analysis. The reaction mixture was cooled to room temperature, diluted with ether (40 mL), filtered, and concentrated. The crude reaction mixture was then recrystallized from MeOH to furnish the desired product in 90% yield.

b) 6-Amino-1-ethyl-4-oxo-1,4-dihydro-quinoline-3-carboxylic acid ethyl ester

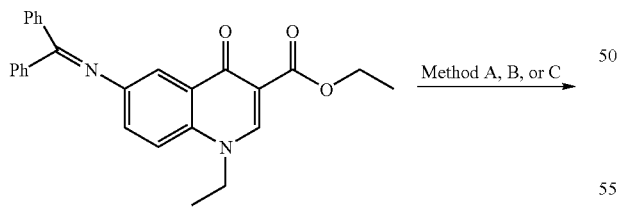

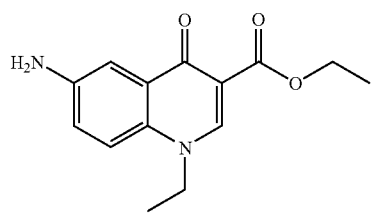

Method A: Transamination with Hydroxylamine

To a solution of the imine adduct in MeOH (0.1 M) at RT was added NaOAc (2.4 eq) and hydroxylamine hydrochloride (1.8 eq). Oxime formation was usually complete in 15 to 30 minutes. The solution was then partitioned between 0.1 M NaOH and CH$_2$Cl$_2$. The organic layer was dried over anhydrous Na$_2$SO$_4$ and concentrated in vacuo. The product was purified by chromatography on silica gel.

Method B: Hydrogenolysis

A solution of the imine adduct, ammonium formate (15 eq) and 5% Pd/C (10 mol %) was heated to 60° C. in MeOH (0.2 M in imine). After 2 hours, reduction was usually complete. The solution was cooled to room temperature and diluted with CH$_2$Cl$_2$ (5× volume of MeOH) to be passed through a plug of celite. The organic solution was washed with 0.1 M NaOH, dried over anhydrous Na$_2$SO$_4$ and concentrated in vacuo. The product was purified by chromatography on silica gel.

Method C: Acidic Hydrolysis

To a solution of the imine adduct in THF (0.3 M) aqueous 2.0 M HCl (added 5% by volume of THF) was added. After 5-20 minutes hydrolysis was complete and the reaction mixture was partitioned betwen 0.5 M HCl and 2:1 hexane/EtOAc. The aqueous layer was separated and made alkaline. The product aniline was extracted with CH$_2$Cl$_2$, dried over anhydrous Na$_2$SO$_4$ and concentrated in vacuo.

Intermediate 23

[2-(2-Hydroxy-ethoxy)-ethyl]-carbamic acid tert-butyl ester

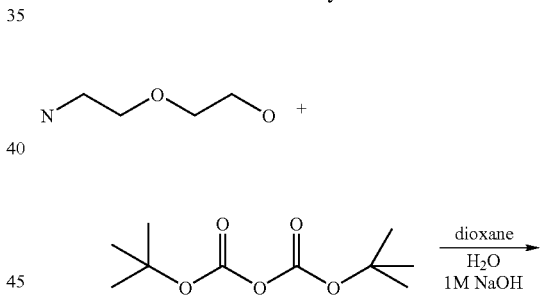

To the solution of dioxane (40 mL), H$_2$O (20 mL) and NaOH (20 mL; 1 M) was added 2-(2-aminoetoxy)ethanol. The reaction mixture was cooled to 0° C. and di-t-Bu dicarbonate (4.8 g) was added. The mixture was stirred for 30 min at 0° C., and then the stirring was continued for 2 hours at room temperature. In next 3 hours two portion of di-t-Bu dicarbonate (2×0.22 g) were added. The mixture was stirred over night at room temperature and then concentrated (20-30 mL). EtOAc (60 mL) was added to the solution and pH was adjusted to 2.5. Aqueous layer was extracted with EtOAc (3×20 mL). Organic layers was washed with H$_2$O (3×30 mL), dried over K$_2$CO$_3$ and evaporated in vacuum to give 3.7 g of the title product as oil.

Intermediate 24

6-[3-(2-Amino-ethoxy)-prop-1-ynyl]-1-ethyl-4-oxo-1,4-dihydro-quinoline-3-carboxylic acid trifluoroacetate salt

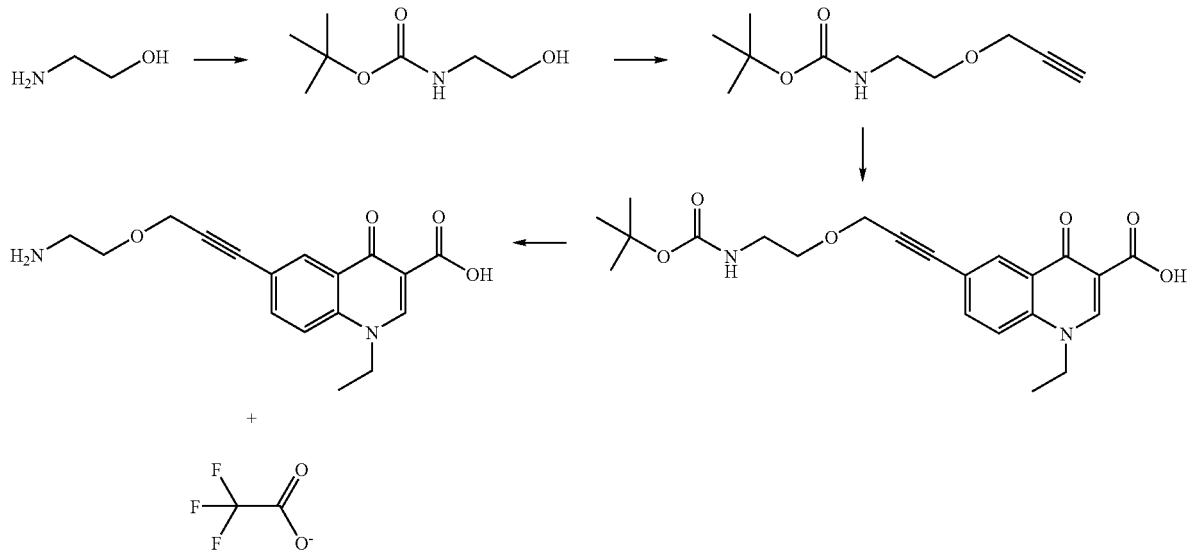

a) (2-Hydroxy-ethyl)-carbamic acid tert-butyl ester

To a stirring solution of ethanolamine (1.96 mL, 32.7 mmol) in dioxane (40 mL) and water (20 mL) saturated solution of NaHCO$_3$ (20 mL) was added. The solution was cooled in ice bath and di-t-butyl dicarbonate (8.0 g) was added portionwise. After 1 hour TLC showed no starting material. EtOAc (50 mL) and water (20 mL) were added, organic layer was separated and evaporated yielding 4.20 g of the oily title compound.

b) (2-Prop-2-ynyloxy-ethyl)-carbamic acid tert-butyl ester

To a stirring solution of Intermediate 24a (1.16 g) in THF (30 mL) at room temperature t-butylammonium iodide (0.15 g), sodium iodide (0.15 g) and propargyl bromide (80% in toluene, 1.20 mL) were added. KOH (0.40 g) was added portionwise during 30 minutes and the suspension was stirred at room temperature for 24 hours. The solvent was evaporated, EtOAc (30 mL) and water (30 mL) were added, organic layer was washed with 10% Na$_2$S$_2$O$_5$ solution and evaporated yielding 1.21 g of the title compound.

c) 6-[3-(2-tert-Butoxycarbonylamino-ethoxy)-prop-1-ynyl]-1-ethyl-4-oxo-1,4-dihydro-quinoline-3-carboxylic acid CuI (55 mg) and triethylamine (14.06 mL) were added into a solution of 1-ethyl-6-iodo-4-oxo-1,4-dihydro-quinoline-3-carboxylic acid (1.0 g) in MeCN (20 mL). The mixture has been stirring at room temperature for 20 minutes. Pd(PPh3)$_2$Cl$_2$ (61 mg) and Intermediate 24b (0.70 g) were added and the mixture has been stirring at 50° C. for 4 hours. The solvents were evaporated, EtOAc (30 mL) and water (30 mL) were added, organic layer was washed with water (30 mL) and brine (30 ml) and evaporated yielding 1.0 g of the title compound.

MS (ES+) m/z: [MH]$^+$=415.24 d) 6-[3-(2-Amino-ethoxy)-prop-1-ynyl]-1-ethyl-4-oxo-1,4-dihydro-quinoline-3-carboxylic acid trifluoroacetate salt Trifluoroacetic acid (0.386 mL) was added into solution of Intermediate 24c (0.42 g) in MeCN (5 mL) at room temperature. The solution has been stirring at room temperature for 48 hours and evaporated yielding 0.80 g of the title compound.

Intermediate 25:

7-Chloro-1-cyclopropyl-6-(2-hydroxy-ethoxy)-4-oxo-1,4-dihydro-quinoline-3-carboxylic acid (A) and

1-Cyclopropyl-6-fluoro-7-(2-hydroxy-ethoxy)-4-oxo-1,4-dihydro-quinoline-3-carboxylic acid (B)

To a mixture of DMSO (5 mL) and ethyleneglycol (6 mL), KO$^t$Bu (1.6 g, 14.23 mmol) was added portion-wise over 10 min, and then heated to 90° C. To the mixture, 7-chloro-1-cyclopropyl-6-fluoro-4-oxo-1,4-dihydro-quinoline-3-carboxylic acid (1.0 g) was added portionwise over 20 min, the temperature was increased to 105° C. and the mixture was stirred for 6 h. Water (30 mL) was added to the reaction solution and the pH of the solution was adjusted to pH=5. The resulting solution was left in the refrigerator overnight. The precipitate obtained was filtered, washed with cold water, and dried affording a 2:1 mixture of Intermediate 25A and Intermediate 25B (1.0 g).

Part of the crude product (700 mg) was dissolved in EtOH (15 mL) by heating to the reflux. The resulting solution was cooled to 30° C. and a first precipitation occurred. The precipitate was filtered, washed with cold EtOH and dried under reduced pressure. Intermediate 24A (204 mg) was obtained as a white solid.

$^1$H-NMR (500 MHz, DMSO-d6) δ: 15.06 (s, 1H), 8.71 (s, 1H), 8.40 (s, 1H), 7.86 (s, 1H), 4.97 (t, 1H), 4.25 (t, 2H), 3.87

(m, 1H), 3.82 (q, 2H), 1.32 (m, 2H), 1.20 (m, 2H); $^{13}$C-NMR (75 MHz, DMSO-d6) δ: 176.61, 165.67, 152.47, 147.54, 135.34, 129.48, 124.95, 120.02, 106.90, 106.66, 71.22, 59.15, 35.99, 7.46.

Intermediate 26

7-Chloro-6-[2-(2-cyano-ethoxy)-ethoxy]-1-cyclopropyl-4-oxo-1,4-dihydro-quinoline-3-carboxylic acid To a suspension of Intermediate 25A (2 g) in acrylonitrile (40 mL) was added DBU (2.3 mL). The reaction mixture was stirred at 80° C. for 24 h. The acrylonitrile was evaporated under reduced pressure. Isopropanol (30 mL) was added to the residue and the pH of the solution was adjusted to pH=5 by adding 2M HCl, during which the product precipitated. The precipitate was filtered, washed with water, and dried affording Intermediate 25 (1.7 g) as a white solid.

MS (ES+) m/z: [MH]$^+$=377.0 $^1$H-NMR (500 MHz, DMSO-d6) δ: 8.68 (s, 1H), 8.38 (s, 1H), 7.84 (s, 1H), 4.38 (t, 2H), 3.91 (t, 2H), 3.86 (m, 1H), 3.75 (t, 2H), 2.79 (t, 2H), 1.32 (m, 2H), 1.20 (m, 2H); $^{13}$C-NMR (75 MHz, DMSO-d6) δ: 176.63, 165.65, 152.18, 147.61, 135.50, 129.44, 124.97, 120.04, 119.11, 106.96, 106.80, 69.02, 68.30, 65.49, 35.99, 18.06, 7.46.

Intermediate 27

6-[2-(2-Carboxy-ethoxy)-ethoxy]-7-chloro-1-cyclopropyl-4-oxo-1,4-dihydro-quinoline-3-carboxylic acid A solution of Intermediate 26 (1.10 g) in a mixture of conc. H$_2$SO$_4$ (10 mL) and H$_2$O (20 mL) was stirred at 75° C. for 24 h. The pH of the reaction mixture was adjusted to 10.2 with 40% NaOH, during which the product precipitated. The precipitate was filtered, washed with water, and dried affording Intermediate 27 (0.8 g) as a white solid.

MS (ES+) m/z: [MH]$^+$=396.0 $^1$H-NMR (300 MHz, DMSO-d6) δ: 15.0 (s, 1H), 11.8 (s, 1H), 8.69 (s, 1H), 8.38 (s, 1H), 7.85 (s, 1H), 4.35 (m, 2H), 3.91-3.82 (m, 3H), 3.74 (dt, 2H), 2.49 (m, 2H), 1.31 (m, 2H), 1.19 (m, 2H).

Intermediate 28

7-{2-[2-(2-carboxy-ethoxy)ethoxy]ethylamino}-1-cyclopropyl-6-fluoro-4-oxo-1,4-dihydro-quinoline-3-carboxylic acid (A) and 6-{2-[2-(2-carboxy-ethoxy)ethoxy]ethylamino}-1-cyclopropyl-7-chloro-4-oxo-1,4-dihydro-quinoline-3-carboxylic acid (B)

Using the similar procedure to that described in Intermediate 7, starting from a mixture of Intermediate 6A and Intermediate 6B, Intermediate 27 was prepared as a mixture of Intermediate 28A and Intermediate 28B in a 1:1 ratio.

Intermediate 29

6-[2-(2-Amino-ethoxy)-ethylamino]-7-chloro-1-cyclopropyl-4-oxo-1,4-dihydro-quinoline-3-carboxylic acid (A) and 7-[2-(2-Amino-ethoxy)-ethylamino]-1-cyclopropyl-6-fluoro-4-oxo-1,4-dihydro-quinoline-3-carboxylic acid (B)

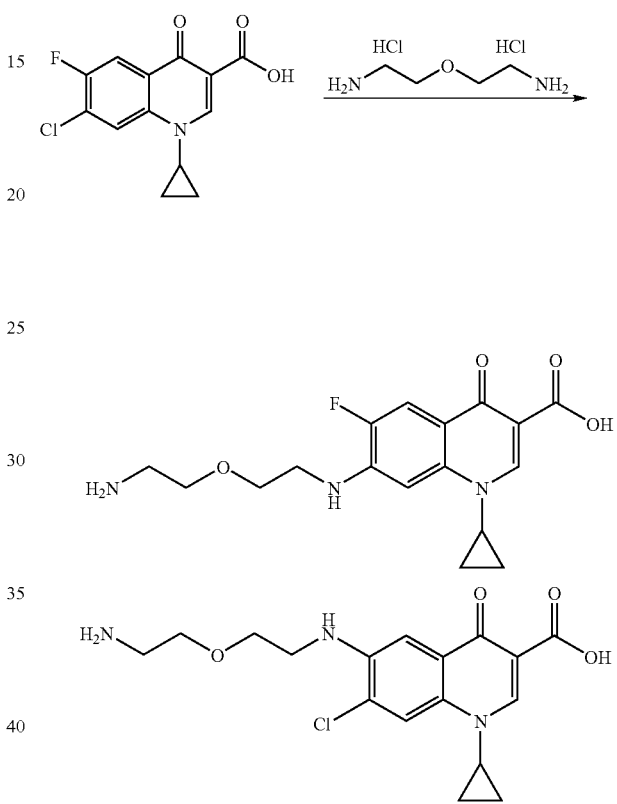

To a solution of 7-chloro-1-cyclopropyl-6-fluoro-4-oxo-1,4-dihydro-quinoline-3-carboxylic acid (0.55 g, 1.95 mmol) in 1-methyl-2-pyrrolidone (40 mL) bis-(2-aminoethyl)-ether dihydrochloride (2.1 g, 11.9 mmol, 6 eq.) and DBU (3.49 mL, 23.4 mmol, 12 eq.) added and the reaction mixture was stirred at 110° C. for 18 hours. The reaction mixture was then diluted with water (70 mL) and the pH was adjusted to 11 and extracted with CH$_2$Cl$_2$ (9×40 mL). Water layer was then acified with H$_2$SO$_4$ to pH 6.8, extracted with 50 mL of CH$_2$Cl$_2$ and then evaporated in vacuum. Crude product was diluted in 2-propanol (60 mL), stirred at 82° C. for 20 minutes and filtrated.

Precipitate was pure salt (Na$_2$SO$_4$). 2-Propanol was evaporated in vacuum and product was purified by column chromatography (fraction, eluent: CH$_2$Cl$_2$-MeOH—NH$_3$—CH$_3$CN=4:4:2:1) yielding 0.5 g of title compounds as a mixture of chloro and fluoro derivatives in ratio 3:1

MS (ES+) m/z: [MH]$^+$=365.8 (A) (75%) MS (ES+) m/z: [MH]$^+$=349.4 (B) (25%).

Intermediate 30

2'-O-Acetyl-4''-O-(2-aminopropyl)-azithromycin 11,12-cyclic carbonate

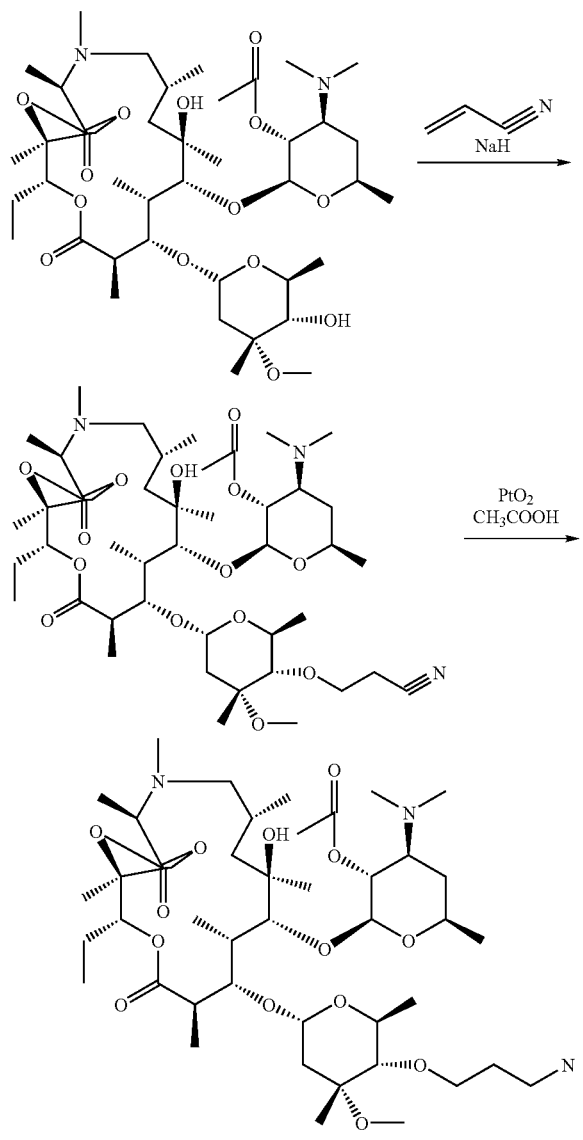

a) 2'-O-Acetyl-4''-O-(2-cyano-ethyl)-azithromycin 11,12-cyclic carbonate

To the degassed solution of 2'-O-acetyl-azithromycin-11,12-cyclic carbonate (10 g, 12.2 mmol) in acrylonitrile (250 mL), t-BuOH (3.465 mL, 36 mmol) and NaH (528 mg, 13.2 mmol) were added in portion-wise at 0° C. The reaction mixture was stirred at 0° C. to for 8 h. Than, acrylonitrile was evaporated and the residue taken up in DCM (50 mL) and extracted with water (3×50 mL). Precipitated polymer between layers was filtered off. The organic layer was dried over $K_2CO_3$ and evaporated under reduced pressure yielding 9.33 g of the title product.

MS (ES+) m/z: $[MH]^+$=870.56.

b) 2'-O-Acetyl-4''-O-(3-amino-propyl)-azithromycin 11,12-cyclic carbonate

Reduction of Intermediate 30a (3 g, 3.45 mmol) in glacial $CH_3COOH$ (120 mL) with $PtO_2$ (1.0 g) in Parr apparatus at 5 bar for 18 hours resulted with the title product (1.46 g).

MS (ES+) m/z: $[MH]^+$=875.0.

Intermediate 31

4''-O-(3-amino-propyl)-azithromycin

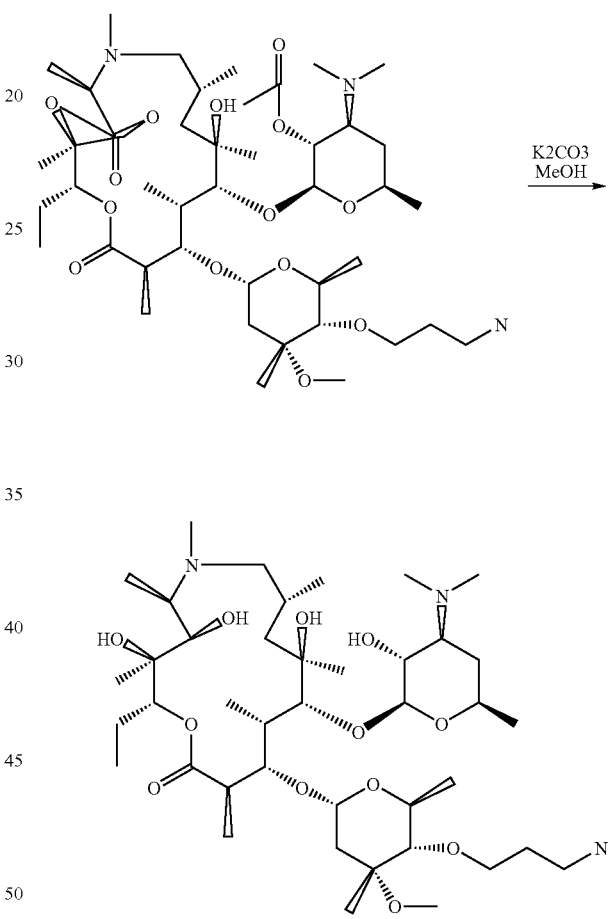

To the solution of Intermediate 30 (1.4 g, 1.6 mmol) in methanol (60 mL) $K_2CO_3$ (2.2 g) dissolved in water (20 mL) was added and the reaction mixture was stirred over night at 50° C. After methanol was evaporated, to the residue water was added (20 mL) and extracted first with EtOAc (2×20 mL) and than with DCM (3×20 mL). Combined DCM extracts were dried over $K_2CO_3$ and evaporated under reduced pressure giving the title product (390 mg).

MS (ES+) m/z: $[MH]^+$=806.2.

Intermediate 32

2'-O-Acetyl-4"-O-(3-oxo-propyl)azithromycin 11,12-cyclic carbonate

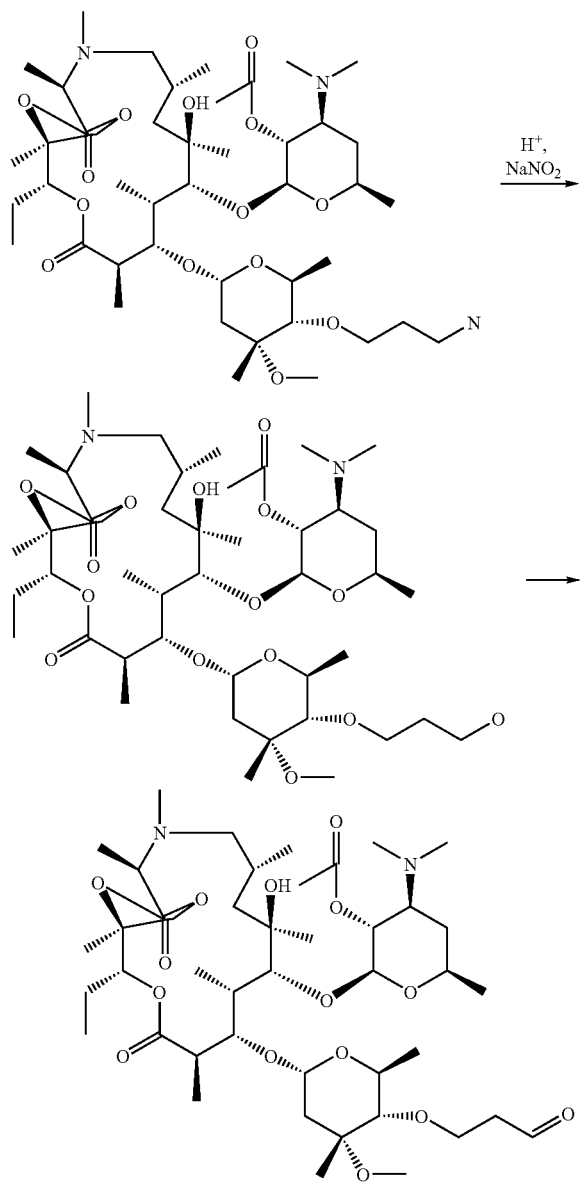

a) 2'-O-Acetyl-4"-O-(3-hydroxy-propyl)-azithromycin 11,12-cyclic carbonate

To a solution of Intermediate 30 (5.0 g, 5.72 mmol) in 10% acetic acid, NaNO$_2$ (2.605 g, 37.75 mmol) in H$_2$O (100 mL) was added portion-wise and reaction mixture was stirred at 0° C. for 3 hours. Than, additional amount of NaNO$_2$ (1.3 g, 18.84 mmol) was added and thr resultant mixture was left over night at 4° C. To the reaction mixture CH$_2$Cl$_2$ was added and pH was adjusted to 10.7 by addition of 40% NaOH. The layers were separated and organic layer was dried over K$_2$CO$_3$ and evaporated under reduced pressure yielding the title compound (4.70 g).

MS (ES+) m/z: [MH]$^+$=875.9. $^1$H NMR (500 MHz, CDCl$_3$) δ: 5.00 (1H, H-1"), 4.85 (1H, H-13), 4.81 (1H, H-2'), 4.66 (1H, H-1'), 4.44 (1H, H-11), 4.29 (1H, H-3), 4.16 (1H, H-5"), 3.97 (1H, —CH$_2$a-2×CH$_2$—O), 3.80 (1H, —CH$_2$—CH$_2$—CH$_2$a-O), 3.77 (1H, H-5'), 3.76 (1H, —CH$_2$b-2×CH$_2$—O), 3.70 (1H, —CH$_2$—CH$_2$—CH$_2$b-O), 3.50 (1H, H-5), 3.35 (3H, 3"OMe), 2.82 (1H, H-10), 2.80 (1H, H-4"), 2.77 (1H, H-2), 2.41 (1H, H-9a), 2.31 (1H, H-2"a), 2.22 (3H, H-9NMe), 2.08 (3H, H-2'OAc), 2.03 (1H, H-9b), 1.95 (1H, H-8), 1.88 (1H, H-4'a), 1.84 (1H, H-4), 1.83 (1H, H-14a), 1.71 (1H, H-4'b), 1.60 (1H, H-7a), 1.55 (1H, H-14b), 1.52 (1H, H-2"b), 1.43 (3H, 12Me), 1.30 (3H, 5"Me), 1.28 (3H, 3"Me), 1.27 (3H, 6Me), 1.25 (3H, 5'Me), 1.19 (3H, 2Me), 1.06 (3H, 10Me), 0.93 (3H, 15Me), 0.91 (3H, 8Me), 0.87 (3H, 4Me). $^{13}$C-NMR (75 MHz, CDCl$_3$) δ: 177.16, 170.36, 153.39, 100.11, 94.87, 87.24, 86.51, 84.83, 84.17, 77.54, 76.54, 74.69, 73.78, 73.44, 68.02, 67.41, 64.46, 63.42, 63.02, 61.62, 49.42, 45.07, 42.91, 42.45, 41.91, 34.99, 34.65, 32.44, 30.61, 27.06, 26.28, 22.26, 22.19, 22.09, 21.38, 18.38, 14.97, 13.86, 10.54, 10.01, 5.30.

b) 2'-O-Acetyl-4"-O-(3-oxo-propyl)azithromycin 11,12-cyclic carbonate

To the degassed solution of Intermediate 32a (0.42 g, 0.48 mmol) in DCM (5 mL) Dess-Martin periodinane (0.225 g, 0.53 mmol) was added and reaction mixture was stirred for 2 hours at RT. After Dess-Martin reagent was filtered off, the residue was extracted with saturated NaHCO$_3$ solution. Organic layer was dried over K$_2$CO$_3$ and evaporated under reduced pressure yielding 0.4 g of the title product.

MS (ES+) m/z: [MH]$^+$=873.6.

Intermediate 33

1-Ethyl-6-iodo-4-oxo-1,4-dihydro-quinoline-3-carboxylic acid

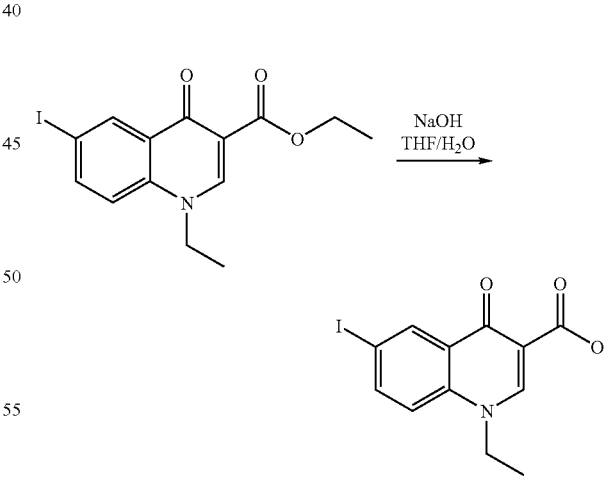

1,4-Dihydro-1-ethyl-6-iodo-4-oxo-quinoline-3-carboxylic acid ethyl ester (7.5 g, 0.02 mol) was suspended in THF (75 mL), NaOH (2 equiv.) solution in water (75 mL) was added and the mixture was stirred at 80° C. for 24 hours. After THF was evaporated, the solution was acidified to pH 5 using HCl. The obtained precipitate was filtrated off and dried under reduced pressure yielding the title compound (7.3 g).

LC/MS(ES+) m/z [MH]$^+$=344.2.

Intermediate 34

1-Ethyl-4-oxo-6-[3-(2-oxo-ethoxy)-propyl]-1,4-dihydro-quinoline-3-carboxylic acid

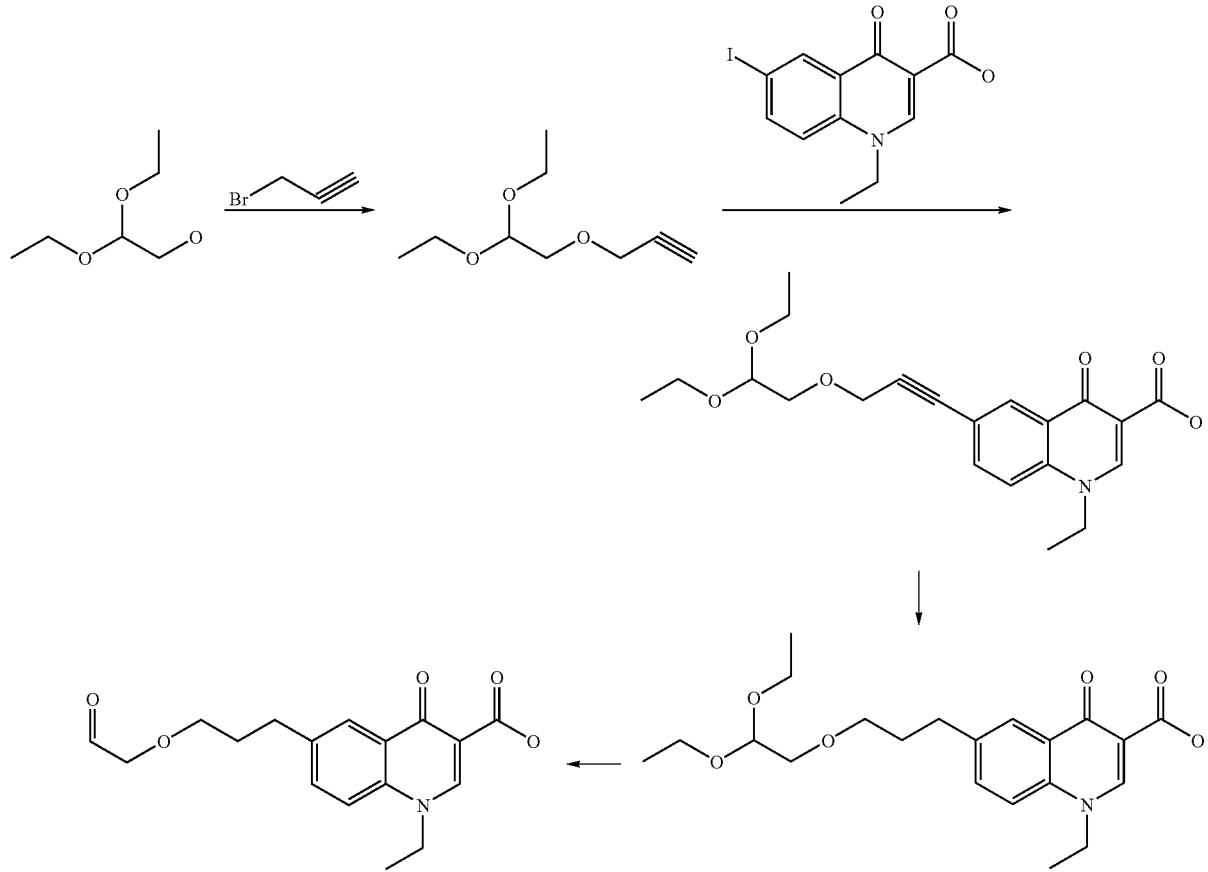

a) 3-(2,2-diethoxy-ethoxy)-propyne (2)

To the degassed solution of NaH (0.06 g, 2.5 mmol) in THF (10 mL) 2,2-diethoxy-ethanol (0.335, 2.5 mmol) was added drop wise. The reaction mixture was stirred at RT for 2 hours and than 3-bromo-propyne (0.29 ml, 3.25 mmol) solution in THF (10 mL) was added. Resulting mixture was stirred at RT over night. Solvent was evaporated, to the residue EtOAc was added and extracted with water (2×20 mL). The organic layer was dried over $K_2CO_3$ and evaporated under reduced pressure yielding the title product (0.42 mg).

b) 6-[3-(2,2-diethoxy-ethoxy)-prop-1-ynyl]-1-ethyl-4-oxo-1,4-dihydro-quinoline-3-carboxylic acid Using the procedure of Intermediate 12b the title compound was obtained (0.48 g), starting from Intermediate 33 (0.5 g, 1.46 mmol) and Intermediate 34a (0.42, 2.5 mmol).

MS (ES+) m/z: [MH]$^+$=388.33. $^1$H NMR (500 MHz, DMSO-d$_6$) δ: 9.07 (1H, Q), 8.35 (1H, Q), 8.07 (1H, Q), 7.98 (1H, Q), 4.66 (1H, O—CH—O), 4.60 (2H, Q-N—CH$_2$—CH$_3$), 4.49 (2H, —O—CH$_2$—C≡), 3.64 (2H, O—CH$_2$—CH$_3$), 3.54(2H, —CH—CH$_2$—O), 3.52 (2H, O—CH$_2$—CH$_3$), 1.42 (3H, Q-N—CH$_2$—CH$_3$), 1.10 (3H, O—CH$_2$—CH$_3$). $^{13}$C NMR (75 MHz, DMSO-d$_6$) δ: 177.12, 165.83, 149.74, 138.89, 136.42, 128.83, 125.75, 119.82, 119.12, 108.39, 100.38, 88.16, 84.29, 70.01, 61.64, 58.46, 49.25, 15.43, 14.65.

c) 6-[3-(2,2-diethoxy-ethoxy)-propyl]-1-ethyl-4-oxo-1,4-dihydro-quinoline-3-carboxylic acid The Intermediate 34b (0.45 g, 0.16 mmol) was dissolved in methanol (20 mL), DCM (4 mL) and 10% Pd/C (0.15 g) were added and the reaction mixture was hydrogenated in Parr apparatus at 5 bar for 20 hours giving the title product (0.4 g).

MS (ES+) m/z: [MH]$^+$=392.09. $^1$H NMR (500 MHz, DMSO-d$_6$) δ: 9.03 (1H, Q), 8.19 (1H, Q), 8.00 (1H, Q), 7.85 (1H, Q), 4.60 (2H, Q-N—CH$_2$—CH$_3$), 4.55 (1H, O—CH—O), 3.61 (2H, O—CH$_2$—CH$_3$), 3.49 (2H, O—CH$_2$—CH$_3$), 3.43 (2H, O—CH$_2$—CH$_2$), 3.35 (2H, —CH—CH$_2$—O), 2.83 (2H, —CH$_2$-Q), 1.87 (2H, —CH$_2$—CH$_2$—CH$_2$—), 1.43 (3H, Q-N—CH$_2$—CH$_3$), 1.10 (3H, O—CH$_2$—CH$_2$). $^{13}$C NMR (75 MHz, DMSO-d$_6$) δ: 177.6, 166.01, 148.62, 140.39, 137.5, 134.66, 125.86, 124.7, 118.19, 107.58, 100.65, 70.98, 69.6, 61.64, 49.10, 31.08, 30.63, 15.36, 14.68.

d) 1-Ethyl-4-oxo-6-[3-(2-oxo-ethoxy)-propyl]-1,4-dihydro-quinoline-3-carboxylic acid Mixture of Intermediate 34c (0.2 g, 0.51 mmol) in HCOOH (4 mL) and H$_2$O (1 mL) was stirred at 0° C. for 1.5 hours. Solvents were evaporated yielding the title product (0.15 g).
MS (ES+) m/z: [MH]$^+$=318. $^1$H NMR (500 MHz, DMSO-d$_6$) δ: 9.60 (1H, CHO—CH—O), 9.03 (1H, Q), 8.17 (1H, Q), 8.00 (1H, Q), 7.85 (1H, Q), 4.60 (2H, Q-N—CH$_2$—CH$_3$), 4.18 (1H, CHO—CH—O), 3.49 (2H, O—CH$_2$—CH$_2$), 2.86 (2H, —CH$_2$-Q), 1.91 (2H, —CH$_2$—CH$_2$—CH$_2$—), 1.42 (3H, Q-N—CH$_2$—CH$_3$). $^{13}$C NMR (75 MHz, DMSO-d$_6$) δ: 201.41, 177.42, 166.03, 148.42, 140.11, 137.3, 134.86, 125.36, 125.15, 118.01, 107.37, 75.32, 69.81, 48.83, 30.84, 30.44, 14.47.

Intermediate 35

6-[3-(2-Amino-ethoxy)-propyl]-1-ethyl-4-oxo-1,4-dihydro-quinoline-3-carboxylic acid trifluoroacetate salt

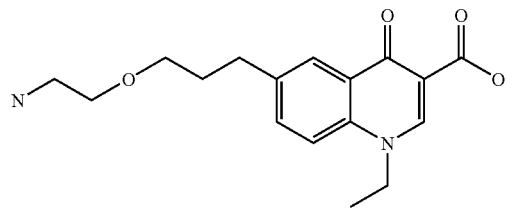

Intermediate 24c was hydrogenated under conditions described for Intermediate 34c, followed by BOC-deprotection by procedure described for Intermediate 5c giving the title compound.

Intermediate 36

9-Dihydro-9-methoxy-4"-O-2-oxoethyl-2',11-bis-O-trimethylsilyl-6-O-methyl-9,12-anhydro-erythromycin A

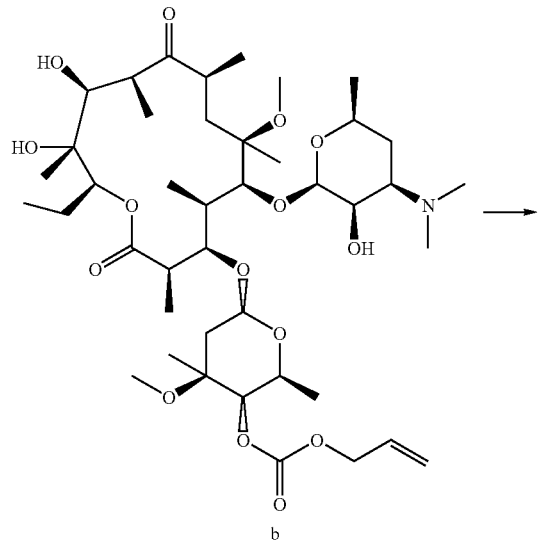
b

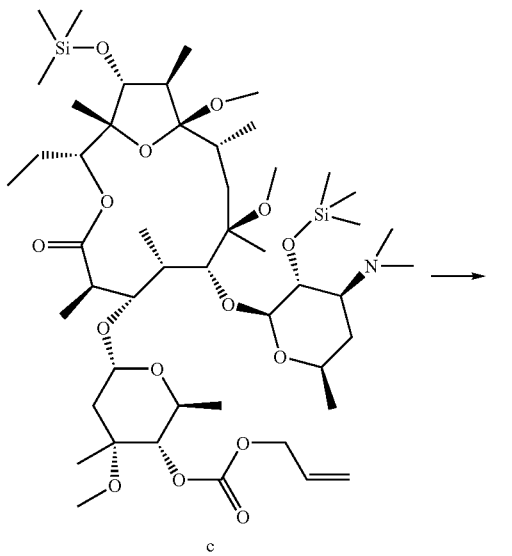
c

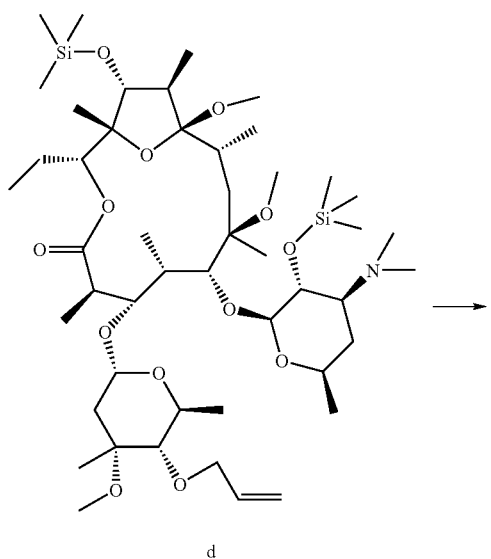
d

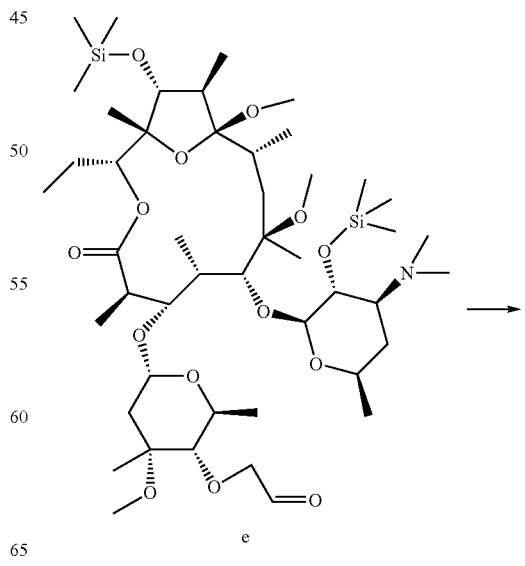
e a) 4"-O-(1-Imidazol-1-yl-carbonyl)-6-O-methyl-erythromycin A

6-O-Methyl-erythromycin A (30 g, 40.1 mmol) in tetrahydrofuran (100 mL) was treated portionwise with carbonyldiimidazole (16 g, 97 mmol) with ice bath cooling. After 1 h the cooling bath was removed. After a further 48 h, tetrahydrofuran (100 mL) and water (200 mL) were added slowly precipitating the title compound, which was collected by filtration and dried to give the title compound (24.7 g). Extraction of the mother liquors with diethyl ether gave further material (8.5 g) which was precipitated from tetrahydrofuran solution with water to give a further portion of the title compound (3.92 g, total of 28.64 g).

MS (ES+) m/z: $[MH]^+$=842.7.

b) 4"-O-(Allyloxycarbonyl)-6-O-methyl-erythromycin A

Intermediate 36a (28.64 g, 34 mmol) in dichloromethane (100 mL) was cooled to 0° C. and treated with allyl alcohol (13.6 mL) and DBU (5.23 mL). The reaction was stirred at 0° C. for 2.5 h and at 20° C. for 1.75 h. The reaction mixture was quenched with 3% aq citric acid (100 mL), the phases separated, and the organic phase washed with sat sodium hydrogen carbonate and brine. After drying and evaporation to dryness, the residue was triturated with petroleum ether (bp 40-60° C.) to give the title compound as a solid (25.08 g).

MS (ES+) m/z: $[MH]^+$=832.8.

c) 4"-O-(Allyloxycarbonyl)-9-dihydro-9-methoxy-2', 11-bis-O-trimethylsilyl-6-O-methyl-9,12-anhydro-erythromycin A Intermediate 36b (22.29 g, 25.6 mmol) in pyridine (100 mL) was treated with chlorotrimethylsilane (26 mL). The reaction was stirred at 20° C. for 6 h and left at 4° C. for 16 h. The reaction mixture was evaporated to dryness under reduced pressure and the residue taken up in methanol (100 mL) After 80 min at 20° C., the solvent was removed by evaporation under reduced pressure and the residue taken up in ethyl acetate and water. the phases were separated, the organic layer dried, and evaporated to dryness under reduced pressure. Toluene (two 500 mL portions) were added and evaporated under reduced pressure to give the crude title compound as a white foam (26.27 g). This material (5.8 g) was purified by chromatography on silica gel eluting with 0-3% 2 M methanolic ammonia in dichloromethane to give the title compound as a white foam (3.0 g).

MS (ES+) m/z: $[MH]^+$=990.8.

d) 4"-O-Allyl-9-dihydro-9-methoxy-2',11-bis-O-trimethylsilyl-6-O-methyl-9,12-anhydro-erythromycin A Intermediate 36c (3.0 g, 3.03 mmol) in tetrahydrofuran (20 mL) was treated with tetrakis triphenylphosphine palladium (0.1 g) at reflux under argon. After 35 min, t-butyl allyl carbonate (F. Houlihan et al, Can. J. Chem. 1985, 63, 153; 1.2 mL) and tetrakis(triphenylphosphine) palladium (0.1 g) were added and the reflux continued for a further 1 h. The reaction was cooled and evaporated to dryness under reduced pressure, and the residue purified by chromatography on silica gel eluting with 0-5% 2 M methanolic ammonia in dichloromethane to give the title product, 1.07 g, as a white foam.

MS (ES+) m/z: $[MH]^+$=946.8.

e) 9-Dihydro-9-methoxy-4"-O-2-oxoethyl-2',11-bis-O-trimethylsilyl-6-O-methyl-9,12-anhydro-erythromycin A To Intermediate 36d (2.0 g) in THF (3 mL) and water (1 mL) under argon was added osmium tetroxide (4% solution in water, 1 mL). After 5 min N-methyl morpholine-N-oxide (0.36 g) was added. After stirring for 1 h, the reaction was cooled in an ice bath and diluted with THF (18 ml) and water (30 mL). Sodium periodate (2.9 g) was added. After stirring for 10 min at 0° C., the reaction was filtered, the solid extracted with ethyl acetate (20 mL) and the phases of the combined filtrates separated. The organic phase was washed with sat. aq. sodium thiosulfate (2×25 mL) and brine (5 mL). After drying with magnesium sulfate, the solution was evaporated to give a white foam. This was taken up in THF (20 mL) and water (30 mL), cooled to 0° C. and sodium periodate (1.5 g) was added. After stirring for 15 min at 0° C., the reaction was filtered, the solid extracted with ethyl acetate (20 mL) and the phases of the combined filtrates separated. The organic phase was washed with sat. aq. sodium thiosulfate (2×25 mL) and brine (5 mL). After drying with magnesium sulfate, the solution was evaporated to give the title compound as a white foam, (1.6 g).

MS (ES+) m/z $[M+H_2O+H]^+$=966.8.

Intermediate 37

2'-O-acetyl-4"-O-2-cyanoethyl-11-O-methyl azithromycin

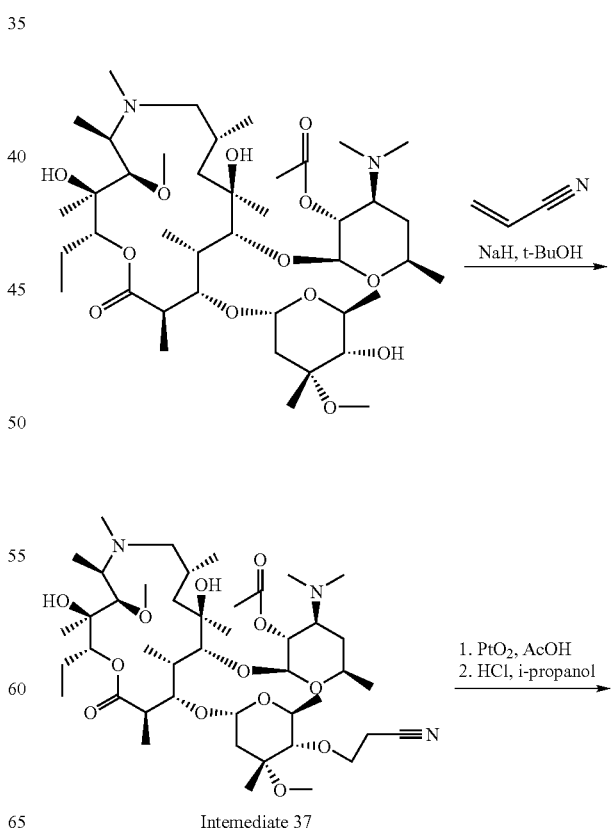

Intermediate 37

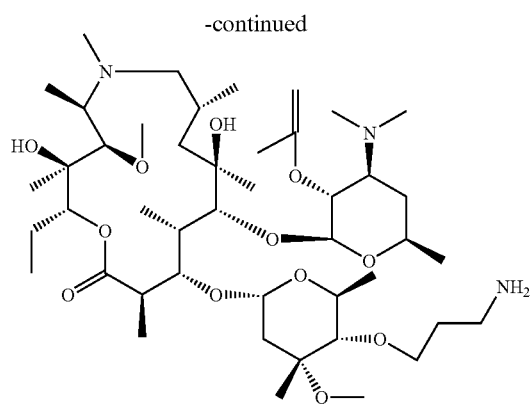

Intermediate 38b

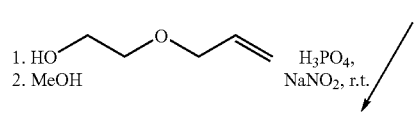

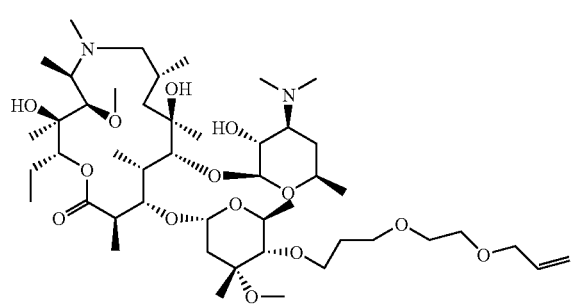

Intermediate 39b

According to the procedure for Intermediate 30A starting from 2'-O-Acetyl-11-O-methylazithromycin (1.0 g, 1.25 mmol) the title compound was obtained (1.05 g).

Intermediate 38

2'-O-Acetyl-4''-O-(3-aminopropyl)-11-O-methly azithromycin trihidrochloride a) 2'-O-Acetyl-4''-O-(3-aminopropyl)-11-O-methly azithromycin According to the procedure for Intermediate 30b starting from Intermediate 37 (0.9 g, 1.05 mmol) the title compound was obtained (670 mg).

b) 2'-O-Acetyl-4''-O-(3-aminopropyl)-11-O-methly azithromycin trihidrochloride

To a solution of Intermediate 38a (0.60 g, 0.70 mmol) in 1-propanol (4 mL), 5N HCl solution in 1-propanol (2.0 mmol) was added. The resulting solution was stirred for 3 min at room temperature, than diisopropyl ether (10 ml) and hexane (20 ml) were added. The resulting precipitate was filtered off and dried thereby affording the title compounds (550 mg).

Intermediate 39

4''-O-[3-(2-Allyloxy-ethoxy)-propyl]-11-O-methyl azithromycin a) 2'-O-Acetyl-4''-O-[3-(2-allyloxy-ethoxy)-propyl]-11-O-methyl azithromycin The Intermediate 38b (0.53 g, 0.54 mmol) was dissolved in allyloxyethanol and the pH was adjusted to 4 with orthophosphoric acid. The solution was cooled to 0° C. under $N_2$ atmosphere, $NaNO_2$ (0.24 g, 3.5 mmol, 6 eq.) was added during 1 hour and the reaction mixture was stirred for an additional 5 hours at room temperature. Then water (70 ml) was added, the pH was adjusted to 10.5, extracted with DCM (40 ml) and combined organic layers were dried over $K_2CO_3$ and evaporated in vacuum yielding the crude title product.

b) 4''-O-[3-(2-Allyloxy-ethoxy)-propyl]-11-O-methyl azithromycin

The Intermediate 39a was dissolved in methanol (50 ml) and stirred at 55-65° C. for 18 hours. The methanol was evaporated under reduced pressure and the crude product purified by column chromatography on silicagel using solvent system: $DCM:MeOH:NH_3$=90:9:0.5, affording the title product (120 mg).

MS (ES+) m/z: $[MH]^+$=905.0.

Intermediate 40

2'-O-Acetyl-4''-O-(2-cyanoethyl)-9-[(E)-1-isopropoxy-cyclohexyloxyimino]-6-O-methyl erythromycin A 11,12-cyclic carbonate

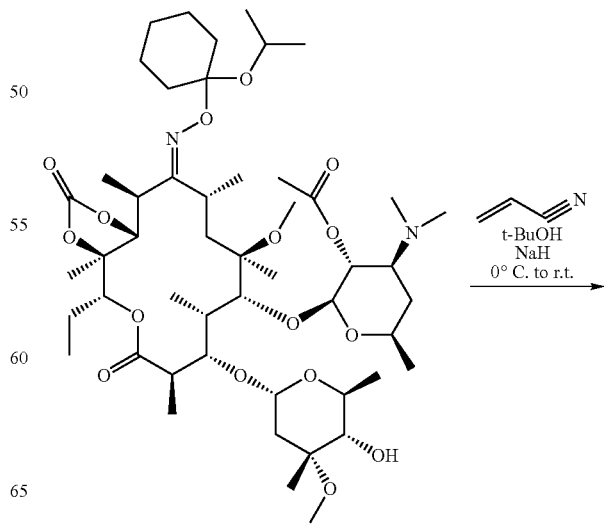

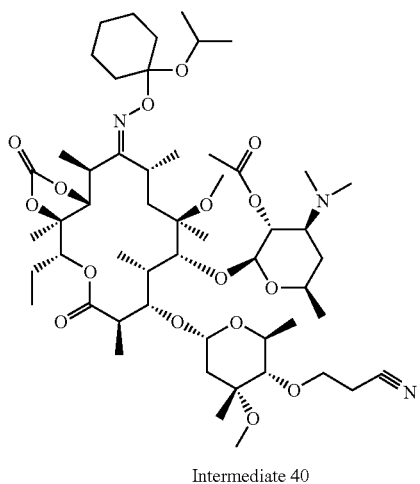

Intermediate 40

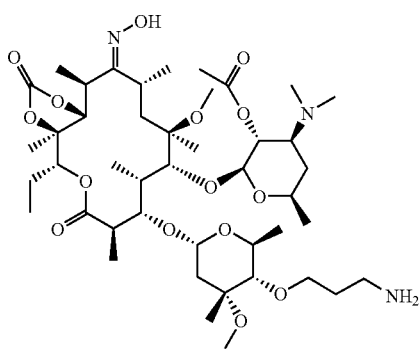

Intermediate 41

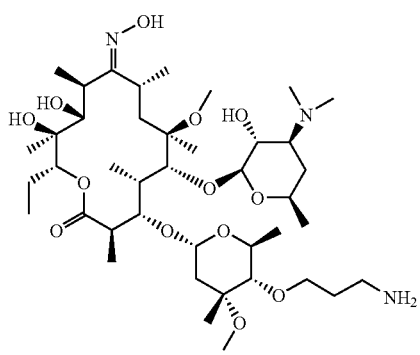

Intermediate 42

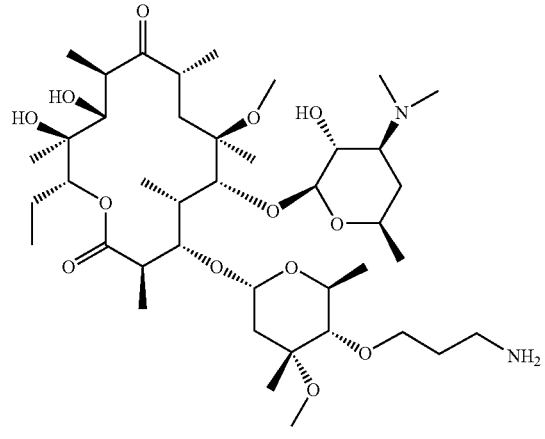

Intermediate 43

According to the procedure for Intermediate 30a starting from 2'-O-acetyl-9-[(E)-1-isopropoxy-cyclohexyloxy-imino]-6-O-methyl erythromycin A 11,12-cyclic carbonate (1.7 g, 1.75 mmol) the title compound was obtained as yellow oily product (2.07 g).

MS m/z: (ES): MH$^+$=1025.0.

Intermediate 41

2'-O-Acetyl-4''-O-(3-aminopropyl)-9-(E)-hydroxy-imino-6-O-methyl erythromycin A 11,12-cyclic carbonate According to the procedure for Intermediate 30b starting from Intermediate 40 (1.35 g, 2.0 mmol) the title compound was obtained (1.35 g).

MS m/z: (ES): MH$^+$=888.9.

Intermediate 42

4''-O-(3-aminopropyl)-9-(E)-hydroxyimino-6-O-methyl erythromycin A

According to the procedure for Intermediate 31 starting from Intermediate 41 (1.34 g, 1.51 mmol) the title compound was obtained (0.96 g).

MS m/z: (ES): MH$^+$=820.8 $^{13}$C-NMR(75 MHz, CDCl$_3$) δ: 175.2, 169.0, 101.9, 95.6, 87.0, 79.9, 78.1, 77.7, 76.2, 73.4, 73.0, 72.2, 70.7, 69.7, 67.4, 64.2, 63.9, 50.5, 49.1, 44.4, 39.6, 39.1, 38.4, 36.8, 34.9, 32.7, 32.0, 28.2, 24.8, 21.2, 21.1, 20.6, 19.3, 18.1, 15.4, 14.5, 10.0, 8.56.

Intermediate 43

4''-O-(3-aminopropyl)-6-O-methyl erythromycin A

To the solution of Intermediate 42 (0.39 g, 0.48 mmol) in EtOH (5 ml), water (6 ml), HCOOH (0.051 μl, 1.34 mmol) and Na$_2$S$_2$O$_5$ (0.365 g, 1.92 mmol) were added at room temperature. Reaction mixture was stirred at 80° C. for 30 minutes and than another portion of Na$_2$S$_2$O$_5$ (0.365 g, 1.92 mmol) was added. Stirring proceeded at 80° C. for 4 hours. Solvent was evaporated and residue dissolved in DCM (20 ml) and water (20 ml), the pH was adjusted to 9.3 by addition of aqueous ammonia and extracted with DCM. The combined organic layers were washed with water, dried over K$_2$CO$_3$ and evaporated yielding the title product (0.36 g). Crude product was purified by column chromatography (DCM:MeOH: NH₄OH=90:15:1.5) yielding the title compound (0.132 g, 34.2% yield).

MS m/z: (ES): MH⁺=805.4 $^{13}$C-NMR(75 MHz, CDCl₃) δ: 221.1, 175.8, 102.8, 96.3, 87.4, 81.4, 78.6, 78.4, 76.6, 74.3, 73.5, 72.9, 71.2, 69.1, 68.2, 64.9, 64.5, 50.6, 49.6, 45.3, 45.0, 40.0, 39.9, 39.3, 39.0, 37.2, 35.5, 33.2, 28.5, 21.8, 21.7, 21.0, 19.6, 18.8, 18.0, 16.0, 15.9, 12.3, 10.6, 9.1.

Intermediate 44

6-[3-(2-carboxy-ethoxy)-propyl]-1-dimethylamino-4-oxo-1,4-dihydro-quinoline-3-carboxylic acid b) 1-Dimethylamino-6-(3-hydroxy-propyl)-4-oxo-1, 4-dihydro-quinoline-3-carboxylic acid To a suspension of Intermediate 44a (1.25 g, 4.37 mmol) in DCM (35 ml) and MeOH (45 ml), 10% Pd/C (0.500 g) was added and hydrogenated in Parr apparatus at 4 bar of H₂-pressure for 18 hours. The catalyst was filtered off, washed with DCM and the solvent evaporated under reduced pressure. Crude product was precipitated from DCM-diisopropyl ether, affording the title product (0.85 g (67%).

MS (ES) m/z: [MH]⁺=290.5.

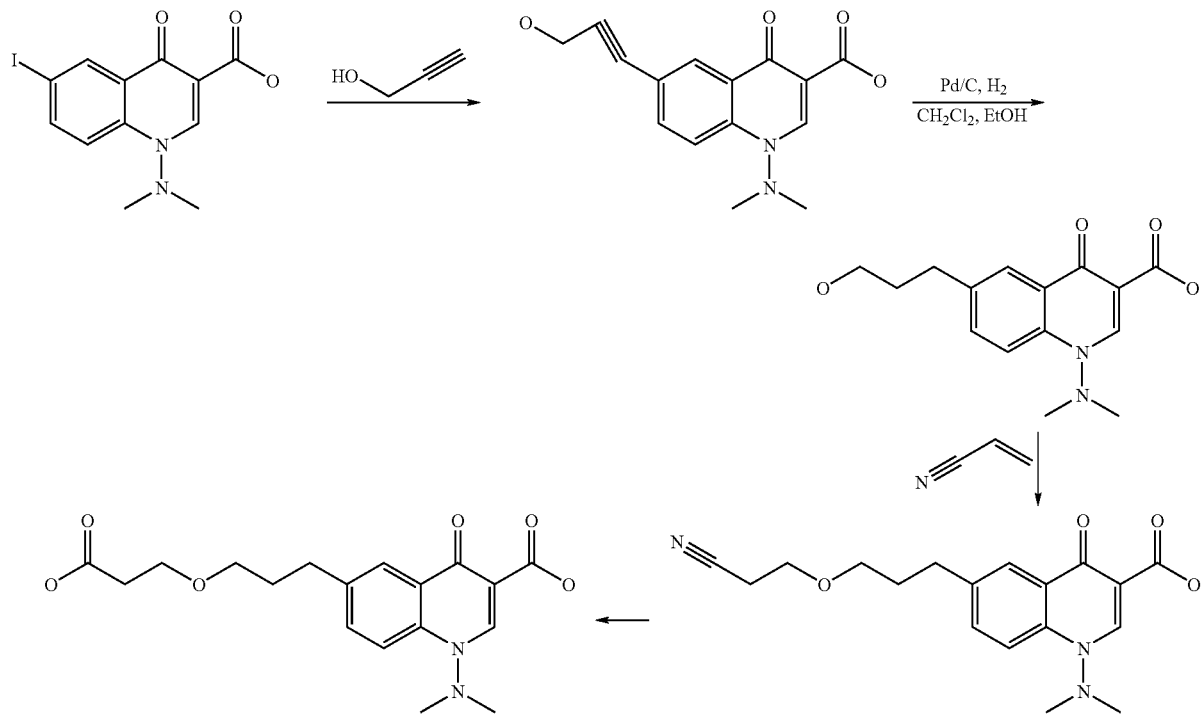

a) 1-Dimethylamino-6-(3-hydroxy-prop-1-ynyl)-4-oxo-1,4-dihydro-quinoline-3-carboxylic acid To a solution of 1-dimethylamino-6-iodo-4-oxo-1,4-dihydro-quinoline-3-carboxylic acid (2.77 g, 7.73 mol) in MeCN (70 ml), CuI (0.15 g, 0.773 mol) and TEA (37.5 ml, 270 mol) were added and stirred for 20 minutes and then warmed up to 50° C. To the reaction mixture propargyl alcohol (1.08 ml, 2.4 mmol) and Pd(PPh₃)₂Cl₂ (0.27 g, 0.39 mol) were added and stirred at 50° C. for 3 hours. Then water (130 ml) and diisopropyl-ether (100 ml) were added, the pH was adjusted to 12, the layers were separated and H₂O layer extracted with diisopropyl-ether (2×50 ml). To the water layer EtOH (14 ml) and charcoal were added, heated to the reflux temperature, and filtered through celite. Then the pH of H₂O solution was adjusted to 6, extracted with DCM (200 ml), combined organic layers were evaporated to obtain the crude product. Precipitation from DCM-hexane afforded the title product (1.25 g, 56%).

MS (ES) m/z: [MH]⁺=286.4.

c) 6-[3-(2-Cyano-ethoxy)-propyl]-1-dimethylamino-4-oxo-1,4-dihydro-quinoline-3-carboxylic acid (0.70 g) were added and the mixture has been stirring at 50° C. for 4 hours. The solvents were evaporated, EtOAc (30 mL)

A suspension of intermediate 44b (0.774 g, 2.66 mol) in 10% NaOH (7.5 ml, 26.66 mmol) was cooled to 5-10° C. After 10 min, acrylonitrile (0.88 ml, 13.3 mmol) was added dropwise and reaction mixture was stirred at 15-20° C. for 2 hours. Then water (5 ml) was added and the pH was adjusted to 6.3 to afford precipitate. Precipitate was filtered off, washed with water dried affording the title product (0.63 g, 70%).

MS (ES) m/z: [MH]⁺=343.6.

d) 6-[3-(2-Carboxy-ethoxy)-propyl]-1-dimethylamino-4-oxo-1,4-dihydro-quinoline-3-carboxylic acid To the concentrated H₂SO₄ (4.7 ml), cooled to 0-5° C., Intermediate 44c (0.912 g 2.66 mmol) was added in portions, keeping temperature at 0-5° C. The reaction mixture was stirred at 10-20° C. for 1 hour and than at room temperature for and additional 18 hours. To the reaction mixture, water (7.5 ml) was added dropwise keeping temperature at 10-20° C. and stirred for an additional 24 hours at 70° C. The reaction mixture was cooled at room temperature and diluted with water (35 ml) giving the title product as precipitate (0.78 g, 81%).

MS (ES) m/z: [MH]$^+$=362.6 [MH]$^+$.

Intermediate 45

4"-O-[3-(3-Allyloxy-propoxy)-propyl]-azithromycin

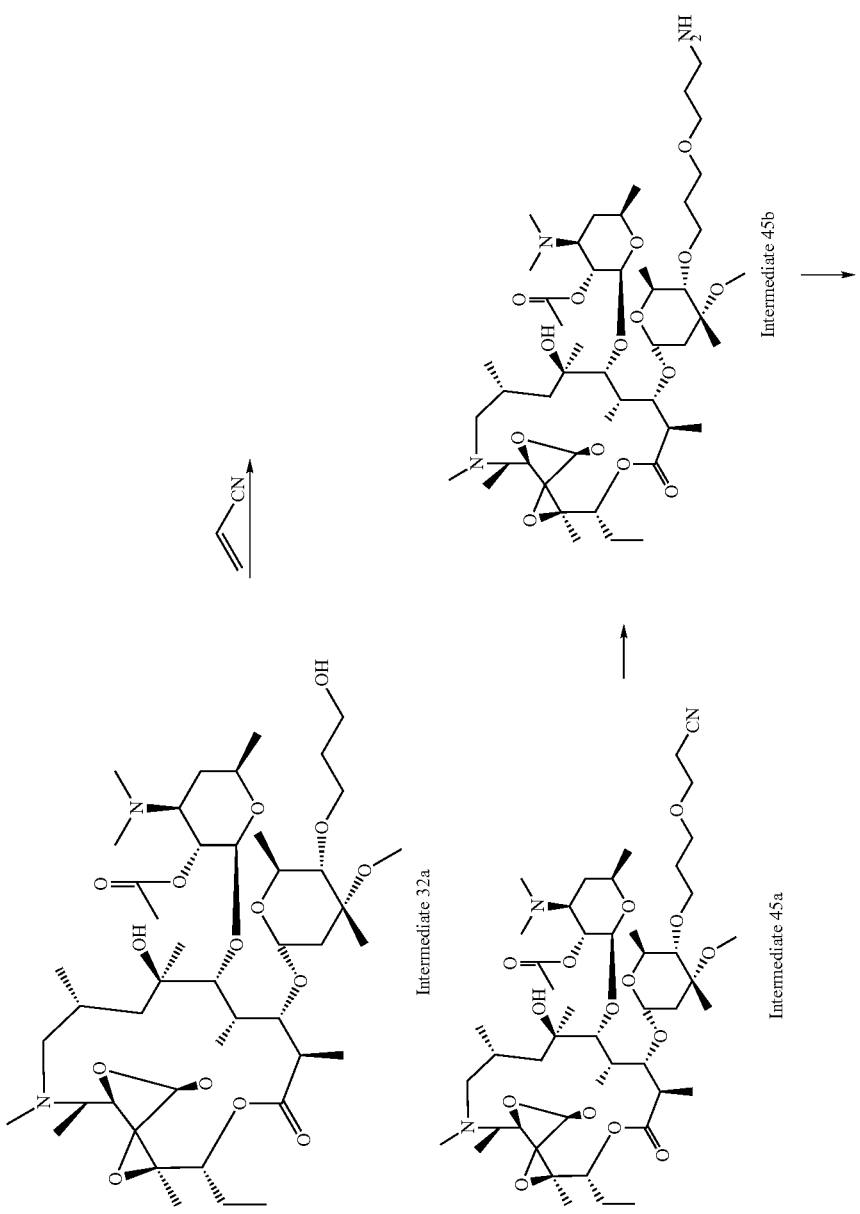

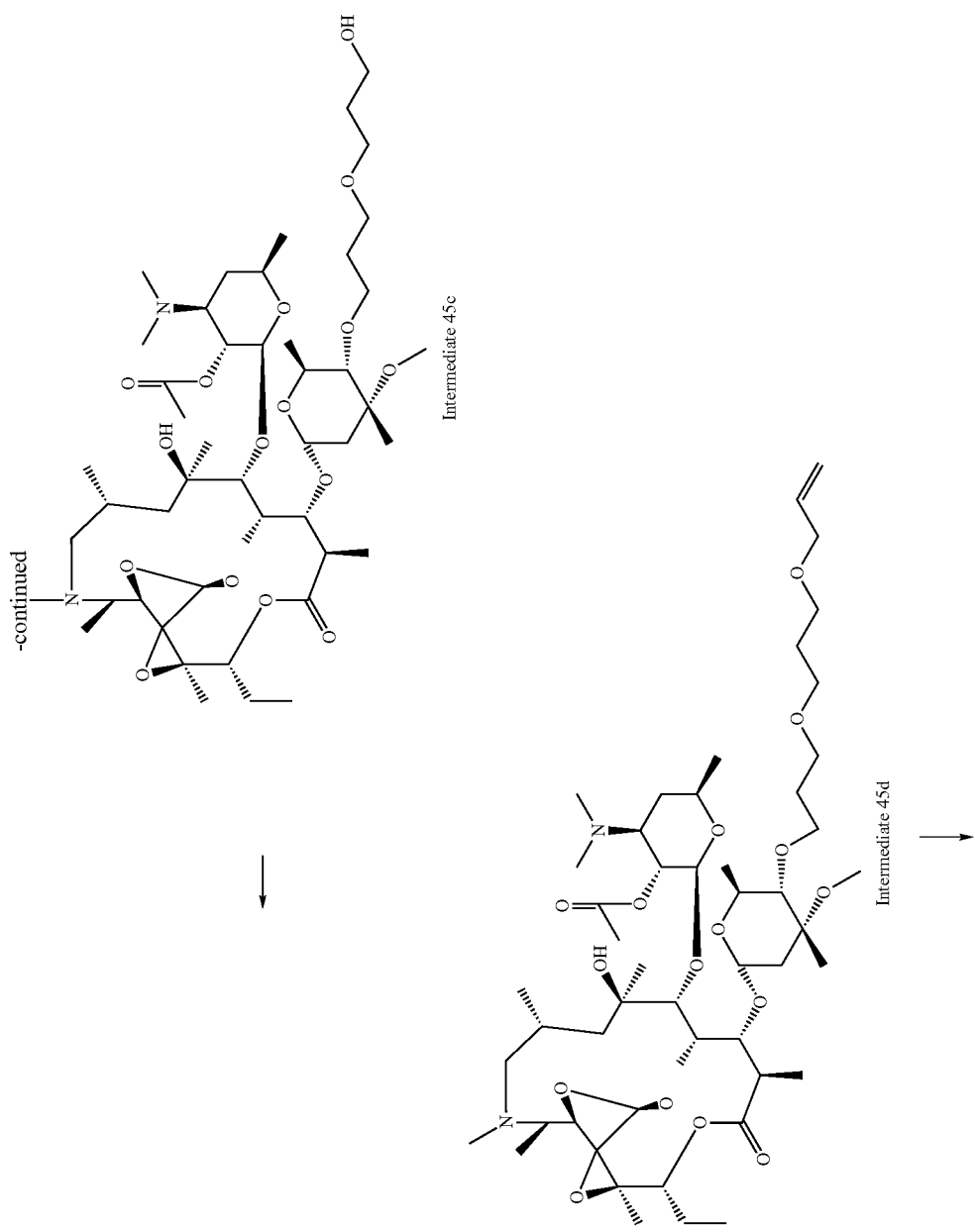

-continued
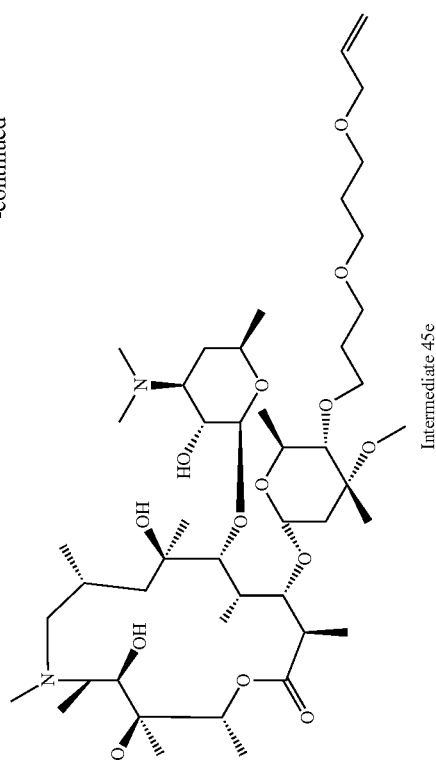
Intermediate 45e a) 2'-O-Acetyl-4"-O-[3-(2-cyanoethoxy)propyl)]-azithromycin 11,12-cyclic carbonate Intermediate 32a (0.5 g, 0.57 mmol) was dissolved in acrylonitrile (10 ml, 0.14 mol, 250 eq.) under $N_2$ atmosphere, t-BuOH (0.18 ml, 1.8 mmol, 3.2 eq.) was added and the reaction mixture cooled to 0° C. Than NaH (0.014 g, 0.57 mmol, 1 eq.) was added and the reaction mixture was stirred at room temperature for 30 minutes. Acrylonitrile was evaporated in vacuum, EtOAc (30 ml) and water (30 ml) were added, layers were separated and organic one washed with brine (30 ml), dried over $K_2CO_3$ and evaporated in vacuum yielding the title compound (0.51 g).

MS (ES) m/z: $[MH]^+$ 928.1.

b) 2'-O-Acetyl-4"-O-[3-(3-aminopropoxy)propyl)]-azithromycin 11,12-cyclic carbonate Intermediate 45a (0.77 g, 0.83 mmol) was dissolved in HOAc (30 ml), $PtO_2$ (0.2 g) was added, and hydrogenation performed at 5 bar $H_2$ pressure overnight. The catalyst was filtered off through cellite and solvent evaporated in vacuum yielding oily product (1.5 g) that was used in the next step without purification.

MS (ES) m/z: $[MH]^+$=932.2 c) 2'-O-Acetyl-4"-O-[3-(3-hydroxypropoxy)propyl)]-azithromycin 11,12-cyclic carbonate According to the procedure described for Intermediate 32a starting from Intermediate 45b (1.5 g, 1.6 mmol) the crude title compound was obtained (1.11 g). The crude product was purified by column chromatography using solvent system EtOAc:n-hexane:diethylamine=100:100:20, yielding the title compound 57 mg.

MS (ES) m/z: $[MH]^+$=933.1.

d) 2'-O-Acetyl-4"-O-[3-(3-allyloxy-propoxy)-propyl]-azithromycin 11,12-cyclic carbonate To a mixture of allyl-tert-butyl carbonate (1.28 g, 8.1 mmol, 29 eq.) and Intermediate 45c (260 mg, 0.28 mmol.) catalysts tris(dibenzylideneacetone)dipalladium (29 mg, 0.028 mmol, 0.1 eq). and 1,4-bis(diphenylphosphino)butane (29 mg, 0.068 mmol, 0.2 eq.) were added and the reaction mixture was stirred at 80° C. for 4 hours. Then tetrakistriphenylphosphine palladium (640 mg, 0.068 mmol, 0.25 eq.) was added and stirring continued for 1 hour. Solvent was evaporated and residue purified by column chromatography (eluent: first 200 ml of hexane, then 100 ml of EtOAc and finally 100 ml of EtOAc:n-hexane:diethylamine=1:1:0.2) yielding the title compound (290 mg).

MS (ES) m/z: $[MH]^+$=973.3.

e) 4"-O-[3-(3-Allyloxy-propoxy)-propyl]-azithromycin

Intermediate 45d (290 mg, 0.3 mmol) was dissolved in MeOH (10 ml), solution of $K_2CO_3$ (620 mg, 4.5 mmol, 15 eq.) in water (5 ml) added and the reaction stirred at 55° C. for 2 hours. Then MeOH was evaporated, EtOAc (30 ml) was added and washed twice with aqueous $NaHCO_3$ (15 ml). Organic layer was dried over $K_2CO_3$, evaporated in vacuum and the residue purified by column chromatography (eluent $DCM:MeOH:NH_3$=90:9:0.5) yielding oily title product (170 mg).

MS (ES) m/z: $[MH]^+$=905.2.

Intermediate 46

4"-O-[3-(2-allyloxy-ethoxy)-propyl]-azithromycin

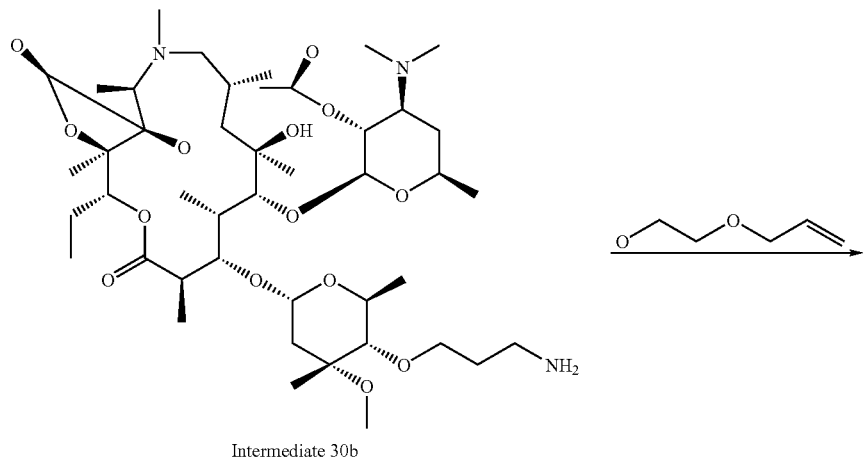

Intermediate 30b

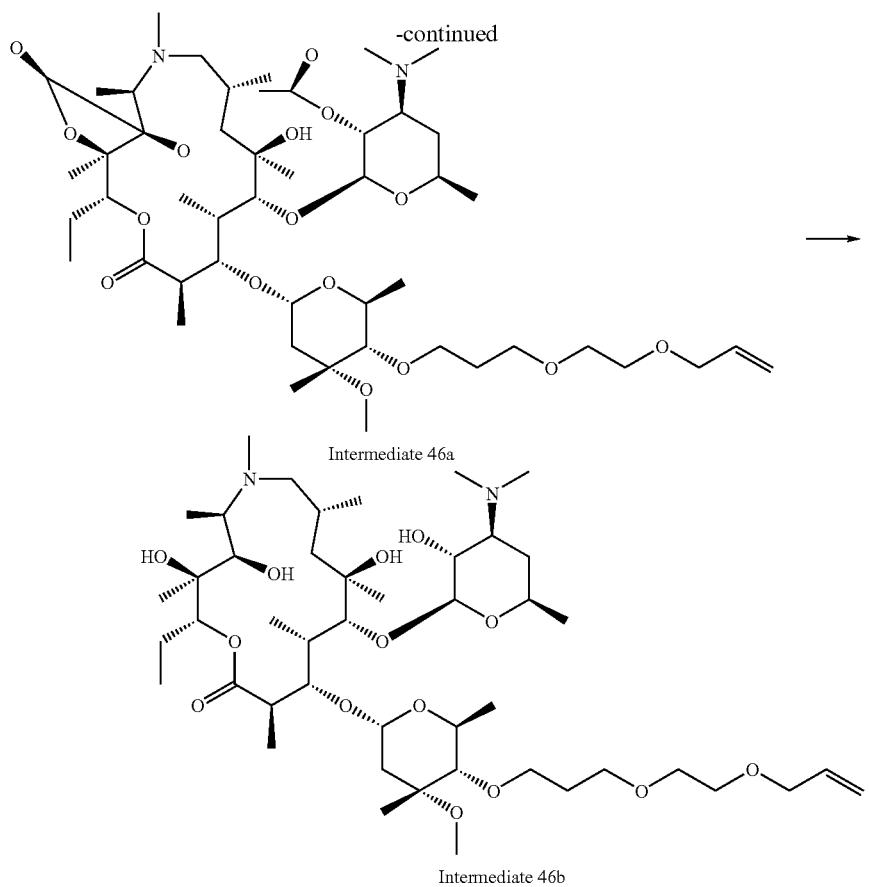

Intermediate 46a

Intermediate 46b a) 2'-O-Acetyl-4"-O-[3-(2-allyloxy-ethoxy)-propyl]-azithromycin 11,12-cyclic carbonate To a solution of hydrochloride salt of Intermediate 30b (1 g, 1.1 mmol) in 2-allyloxy-ethanol (35 ml, 0.33 mol, 300 eq.), $H_3PO_4$ (0.2 ml) was added under $N_2$ atmosphere. Then $NaNO_2$ (1 g, 12 equivalents) was added portionwise during three hours. Reaction mixture diluted with EtOAc (20 ml) and washed with saturated aqueous solution of $NaHCO_3$ (3×30 ml). Evaporation of the organic layer yielded yellow oil (5.6 g) that was used in the next step without purification.

b) 4"-O-[3-(2-allyloxy-ethoxy)-propyl]-azithromycin

According to the procedure of Intermediate 45e starting form Intermediate 46a (5.6 g, ~1 g of product, 1.14 mmol) the title compound was obtained (0.16 g).

MS (ES) m/z: $[MH]^+=891.3$.

Intermediate 47

6-(3-Aminopropyl)-1-(dimethylamino)-4-oxo-1,4-dihydro-3-quinolinecarboxylic acid hydrochloride

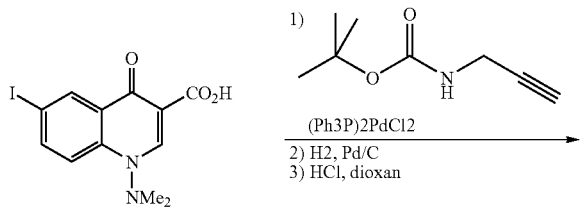

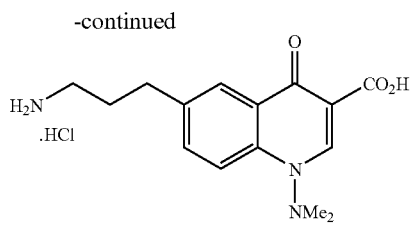

a) 6-(3-t-Butoxycarbonylaminopropyn-1-yl)-1-(dimethylamino)-4-oxo-1,4-dihydro-3-quinolinecarboxylic acid A stirred suspension of 1-dimethylamino-6-iodo-4-oxo-1,4-dihydro-quinoline-3-carboxylic acid (20.46 g) and copper (I) iodide (1.08 g) in triethylamine (260 mL) and acetonitrile (380 mL) was degassed and covered with argon. After 15 min N-t-butoxycarbonylpropargylamine (Casara et al. *J. Chem. Soc. Perkin Trans.* 1 1985; 2201-2208) (10.6 g) and dichlorobis(triphenylphosphine)palladium (II) (1.26 g) were added. After 30 min the mixture was evaporated under reduced pressure and redissolved in aqueous potassium carbonate (16 g in 300 mL). The mixture was washed with diethyl ether (3×), filtered and acidified with citric acid. The solid was filtered off, washed with water and dried to give the title compound (16.5 g).

MS (ES) m/z: $[MH]^+=386.0$.

b) 6-(3-t-Butoxycarbonylaminopropyl)-1-(dimethylamino)-4-oxo-1,4-dihydro-3-quinolinecarboxylic acid A solution of Intermediate 47a (17.26 g) and sodium hydroxide (2.7 g) in methanol (150 mL) and water (300 mL) was treated with 10% palladium on carbon (1 g) and hydrogenated at room temperature and atmospheric pressure overnight. The reaction mixture was filtered, acidified with citric acid, the solid filtered off, washed with water and dried to give the title compound (16.2 g).

MS (ES) m/z: [MH]$^+$=390.0 c) 6-(3-Aminopropyl)-1-(dimethylamino)-4-oxo-1,4-dihydro-3-quinolinecarboxylic acid hydrochloride A solution of Intermediate 47b (16.2 g) in dichloromethane (500 mL) at 20° C. was treated with 4M hydrogen chloride in 1,4-dioxan (100 mL). After 1.5 h the solid was filtered off, washed with acetone and dried to yield the title compound (13.5 g);

$^1$H NMR (250 MHz; DMSO-d$_6$) δ$_H$ 1.94 (2H, m), 2.85 (4H, m), 2.97 (6H, s), 7.87 (1H, dd, J=1.8 & 8.8 Hz), 8.01 (3H, s), 8.20 (1H, d, J=1.8 Hz), 8.24 (1H, d, J=8.8 Hz), 9.28 (1H, s). MS (ES) m/z: [MH]$^+$290.2.

Intermediate 48

4"-O-(2-oxoethyl)-6-O-methyl-erythromycin A a) 4"-O-Allyl-6-O-methyl-erythromycin A

The Intermediate 36c (15.0 g, 15.2 mmol) in dry tetrahydrofuran (100 mL) under argon was treated with tetrakis(triphenylphosphine)palladium (0.36 g) and the resultant mixture heated at reflux for 1.5 h. Allyl t-butyl carbonate (5 mL) (F. Houlihan et al, *Can. J. Chem.* 1985, 63, 153) was added and heating continued for a further 3.75 h. After cooling and standing overnight at 20° C. the tetrahydrofuran was evaporated and the dark brown residue taken up in 40/60 petroleum ether (100 mL). The solution was treated with charcoal, filtered and evaporated. The solid was then taken up in acetonitrile and re-evaporated and dried under vacuum overnight to yield 15.89 g. 12.8 g of this product was dissolved in acetonitrile (25 mL) and 10% aqueous acetic acid (130 mL). After stirring at 20° C. for 6 h diethyl ether (50 mL) was added and the layers separated, the organic layer was extracted with water and the combined aqueous extracts made basic by the addition of potassium carbonate. The organic product was extracted with ethyl acetate (2×100 mL), dried and evaporated to give the title compound as a solid (10.59 g).

MS (ES+) m/z: [MH]$^+$=788.7.

b) 4"-O-(2-oxoethyl)-6-O-methyl-erythromycin A

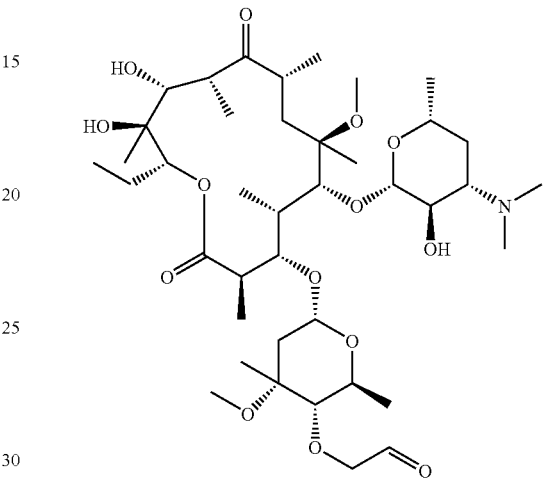

Intermediate 48a (95.8 g, 121 mmol) in dichloromethane (1 L) and methanol (100 mL) was cooled to −78° C. and trifluoroacetic acid (18 mL) added. Ozonized oxygen was bubbled through until a blue colour developed (1.25 h). Argon was bubbled through the mixture to flush out the ozone then dimethyl sulfide (35 mL) and triethylamine (50.4 mL) were added. The reaction was stirred at −78° C. for 30 min then removed from the cooling bath. After 0.5 h the reaction was warmed to 0° C. in a water bath and stirred for a further 0.5 h.

The reaction mixture was washed with water (500 mL), dried (sodium sulfate) and evaporated to dryness. The residue was dissolved in toluene and evaporated three times to give the title compound (103.7 g) which was used without purification.

MS (ES+) m/z: [M+MeOH[+H]$^+$=822.7, MS (ES−) m/z: [M+HCO2]$^−$=834.6.

Intermediate 49

4''-O-[2-(2-Allyloxy-ethoxy)-propyl]-azithromycin

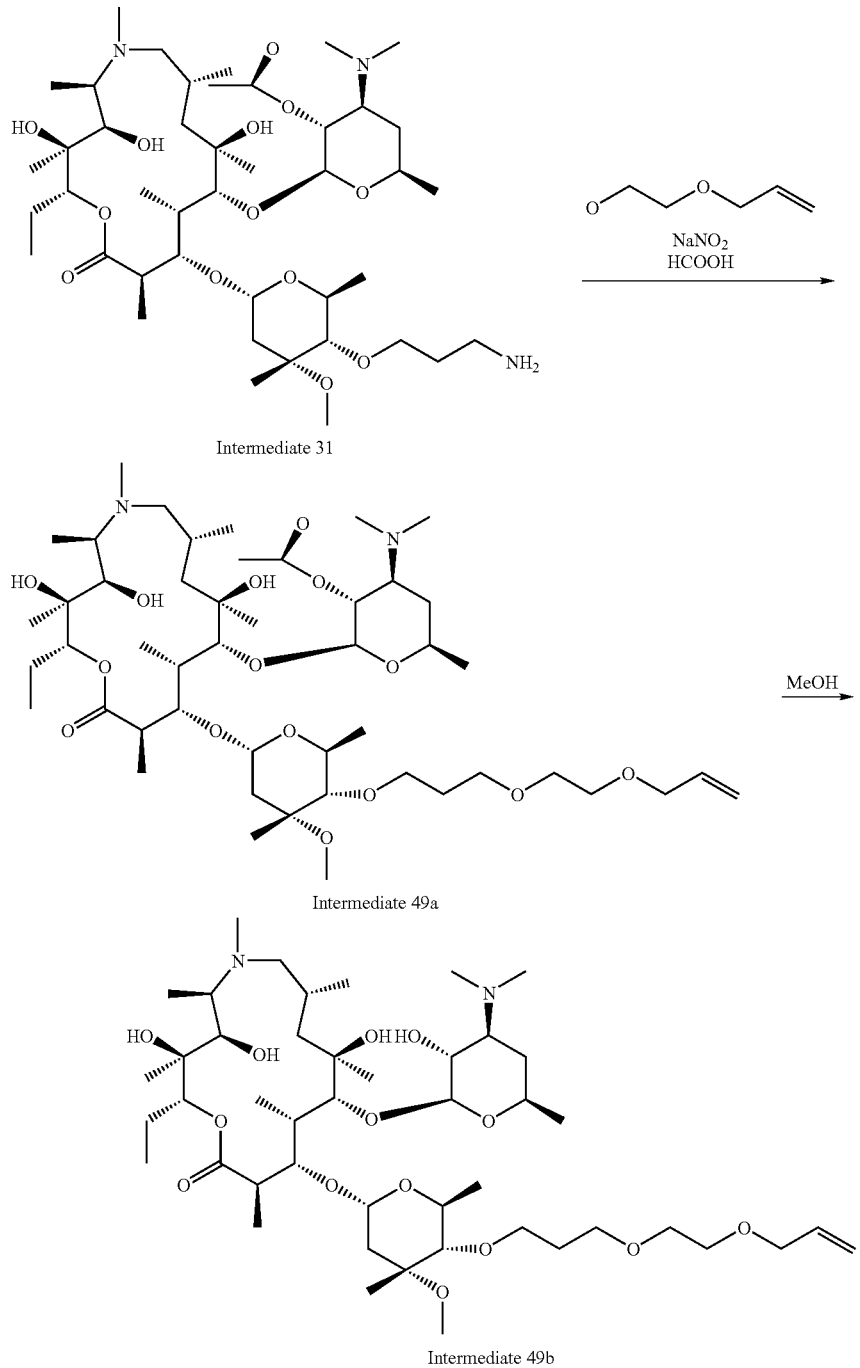

a) 2'-O-Acetyl-4''-O-[3-(2-allyloxy-ethoxy)-propyl]-azithromycin

A solution of Intermediate 31 (0.95 g, 1.12 mmol) in 2-allyloxy-ethanol (12.9 mL, 0.12 mol, 100 equiv.) was cooled to −15° C. under the $N_2$ atmosphere. To the reaction mixture HCOOH (0.2 ml, 5.3 mmol, 4.5 eq.) was added followed by portionwise addition of $NaNO_2$ (0.49 g, 7.1 mmol, 6 eq.) during 10 minutes. The reaction mixture was stirred at −15° C. for 7 hours and then at 4° C. for further 48 hours. Reaction mixture was diluted with EtOAc (20 ml) and extracted with saturated aqueous $NaHCO_3$ (2×30 ml). Organic layer was acidified to pH 3 and extracted with water (20 ml). To the water layer DCM was added (25 mL) and the pH was adjusted to 5.3. Combined organic layers at pH 5.3 were evaporated in vacuum yielding the title product (0.4 g).

MS (ES) m/z: [MH]$^+$=933.2.

b) 4"-O-[3-(2-Allyloxy-ethoxy)-propyl]-azithromycin

Intermediate 49a (0.4 g, 0.45 mmol) was dissolved in MeOH (10 ml) and stirred at 50° C. for 16 hours. Solvent was evaporated in vacuum and product was purified by column chromatography (SP, 20 g, eluent DCM/MeOH=10:3) yielding 78 mg (80% pure by LC/MS) and 196 mg (66% pure by LC/MS) of the title product.

MS (ES) m/z: [MH]$^+$=891.2.

Intermediate 50

4"-O-(3-Aminopropyl)-6-O-methyl-erythromycin A 11,12-cyclic carbamate

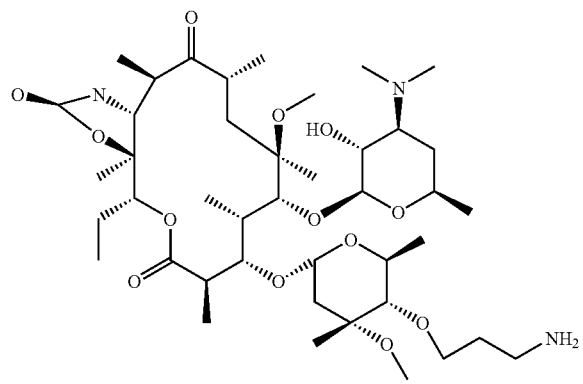

a) 2'-O-Acetyl-6-O-methyl-erythromycin A 11,12-cyclic carbonate

2'-O-Acetyl-6-O-methyl-erythromycin A (31.68 g, 40.1 mmol) was dissolved in DCM (300 ml) at 0° C., pyridine (19.4 ml, 6 eq) was added followed by portion-wise addition of triphosgene (11.91 g, 1 eq) in DCM (30 ml) over 15 minutes. The mixture was stirred at 0° C. for 3 hours, then at room temperature for additional 3 hours and left at −20° C. overnight. Brine (300 ml) was added, layers were separated, the organic one was washed with brine (100 ml), dried over K$_2$CO$_3$ and evaporated yielding the crude residue (38.75 g). The residue was dissolved in DCM (50 ml) and added dropwise to DIPE (380 ml). The resulting suspension was stirred for 10 minutes, filtrated off, washed with DIPE (40 ml) and dried yielding the title compound (28.53 g).

MS (ES) m/z: [MH]$^+$=816.9.

b) 2'-O-Acetyl-4"-O-(2-cyanoethyl)-6-O-methyl-erythromycin A 11,12-cyclic carbonate According to the procedure of Intermediate 30a starting from Intermediate 50a (10.43 g, 12.8 mmol) and acrylonitrile (78 ml, 92 equiv.) the title compound was obtained (9.23 g).

MS (ES) m/z: [MH]$^+$=869.3.

c) 4"-O-(2-Cyanoethyl)-6-O-methyl-10,11-anhydro erythromycin A

Intermediate 50b (9.23 g, 10.6 mmol) was dissolved in EtOAc (45 ml) and toluene (45 ml). DBU (1.59 ml, 1 eq) was added in three portions during 15 minutes at 70° C. and the mixture was stirred at the same temperature overnight. Additional DBU (0.53 ml, 0.3 eq) was added and the mixture was stirred at 70° C. for an additional 3 hours. The solvent was evaporated, the oily residue dissolved in MeOH (200 ml) and stirred at room temperature overnight. Then MeOH was evaporated and the crude product purified by column chromatography (eluent: DCM/MeOH/NH$_3$=90:9:0.5) giving the title compound (1.40 g).

d) 2'-O-Acetyl-4"-O-(2-cyanoethyl)-6-O-methyl-10,11-anhydro erythromycin A

The title compound was prepared (1.36 g) according to the procedure described in *J. Org. Chem.* 1988, 53, 2340, starting from Intermediate 50c (1.40 g, 1.79 mmol).

MS (ES) m/z: [MH]$^+$=825.9.

e) 2'-O-Acetyl-4"-O-(2-cyanoethyl)-6-O-methyl-10,11-anhydro-12-O-imidazoyl erythromycin A Intermediate 50d (1.36 g, 1.65 mmol) was dissolved in DMF (12 ml), CDI (1.067 g, 4 eq) was added followed by portionwise addition of NaH (132 mg, 2 eq) through 10 minutes at 0° C. Mixture was stirred at the same temperature for further 40 minutes, then water (40 ml) was added and the resulting suspension stirred for 5 minutes. The precipitate was filtrated off through, washed with water (10 ml) and dried yielding the title compound (1.310 g).

MS (ES) m/z: [MH]$^+$=920.0.

f) 4"-O-(2-Cyanoethyl)-6-O-methyl-erythromycin A 11,12-cyclic carbamate

Intermediate 50e (1.31 g) was dissolved in MeCN (15 ml) and THF (1.5 ml), NH$_3$ (w=25%, 19 ml) was added and the mixture was stirred at room temperature overnight. Then water (50 ml) and EtOAc (50 ml) were added, organic layer was separated, dried over K$_2$CO$_3$, filtrated and evaporated yielding 2'-O-acetyl protected Intermediate 50f (1.140 g), which was dissolved in MeOH (40 ml), stirred at 50° C. for 3 hours and at room temperature overnight. Then MeOH was evaporated and the residue purified by column chromatography (eluent: DCM/MeOH/NH$_3$=90:9:0.5) yielding the title compound (0.537 g).

MS (ES) m/z: [MH]$^+$=826.8.

g) 4"-O-(3-Aminopropyl)-6-O-methyl-erythromycin A 11,12-cyclic carbamate

According to the procedure of Intermediate 30b starting from Intermediate 50f (537 mg) the title compound was obtained (478 mg).

MS (ES) m/z: [MH]$^+$=830.8.

Example 1

General Procedures for Reductive Amination a) Reductive Amination with NaBH$_3$CN Crude aldehyde (0.14 mmol) was dissolved in 0.9 mL of methanol. Three equivalents of the appropriate amine (0.40 mmol) was added as a 1 M solution in methanol (0.40 mL), followed by 0.43 mL of 1 M solution of acetic acid in methanol. The pH was checked and adjusted to about 6 with acetic acid, if necessary. NaCNBH₃ was added as a freshly prepared 0.3 M solution in methanol (0.19 mL), and the mixture was stirred at room temperature for 2 hours. The reaction was quenched with a few drops of water, concentrated under reduced pressure and the product was purified by silica gel chromatography (1-5% MeOH-0.5-1% triethylamine-DMC.

b) Reductive Amination with Formic Acid

This method was adapted from the work of Debono et al. (J. Antibiot. 1989, 42, 1253-1267). A solution of aldehyde (1.17 mmol), amine (1.75 mmol), and 22.5 mL of EtOAc was heated to 70° C. with stirring. Formic acid (1.28 mmol) was added dropwise to the solution, and the temperature was lowered to 65° C. Stirring and heating was continued for 5 hours. After cooling to room temperature, the reaction solution was washed 2×25 mL of saturated aqueous NaHCO₃ and then 1×20 mL of saturated aqueous NaCl. The combined extracts were dried over anhydrous MgSO₄, filtered, and evaporated under reduced pressure to furnish crude product as a yellow foam. This material was taken up in 100 mL of hot Et₂O; insolubles were filtered and saved. The filtrate was treated with 30 mL of hot hexane, and again the resulting insoluble matter was filtered and saved. The filtrate was concentrated to about 7.5 mL by boiling off excess solvent. The resulting solution was allowed to cool to room temperature and then cooled to 5° C. for several hours. A colorless precipitate formed. The filtrate was combined with the insolubles that were saved, and the mixture was then purified on 45 cc of silica gel. Elution with 9:1 DCM-MeOH containing 1% NH₄OH afforded an additional amount of the product.

c) Reductive Amination with NaBH(OAc)₃

To a magnetically stirred solution of aldehyde (2.65 mmol) in methanol (8 mL) was added appropriate amine (5.3 mmol). After being stirred at room temperature for 30 min, the solution was treated with HOAc (0.15 mL, 2.65 mmol) and cooled to 0° C. In MeOH (2 mL) NaBH₃CN (167 mg, 2.66 mmol) was then added over a period of 10 min. Stirring and cooling was continued for 10 min. The reaction mixture was worked up and the crude product, if necessary, was chromatographed on silica gel column.

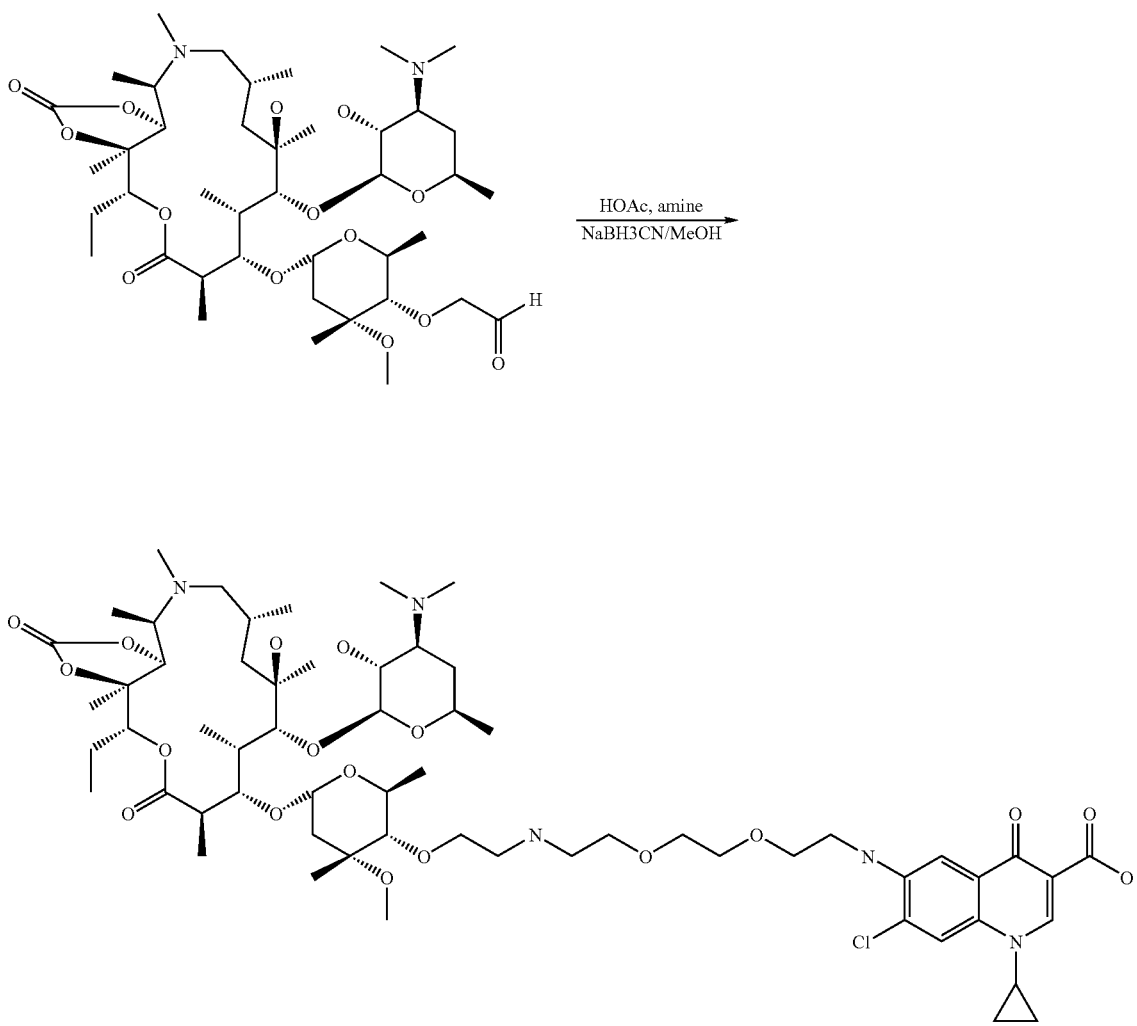

Example 2

4"-O-[2-(2-{2-[2-(3-Carboxy-7-chloro-1-cyclopropyl-4-oxo-1,4-dihydro-quinolin-6-yl-amino)-ethoxy]-ethoxy}-ethylamino)-ethyl]-azithromycin 11,12-cyclic carbonate Using the procedure of Example 1a, Intermediate 17 and Intermediate 11A gave the title compound.
MS (ES+) m/z: [MH]$^+$=1210.8.

Example 3

4"-O-(2-{2-[2-(3-Carboxy-7-chloro-1-cyclopropyl-4-oxo-1,4-dihydro-quinolin-6-ylamino)-ethoxy]-ethylamino}-ethyl)-azithromycin 11,12-cyclic carbonate

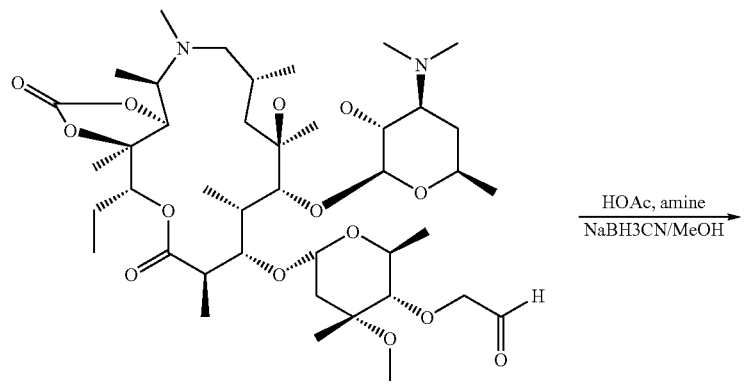

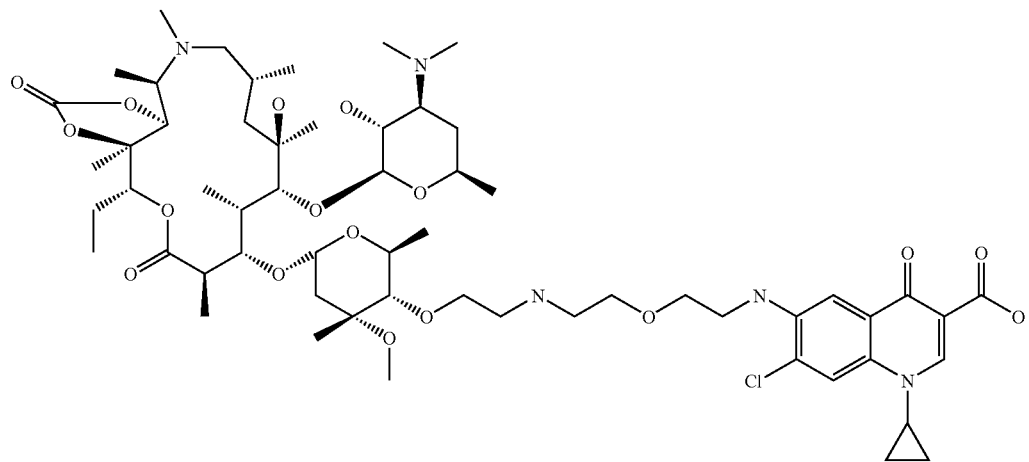

Using the procedure of Example 1a, Intermediate 17 and Intermediate 29A gave the title compound.
MS (ES+) m/z: [MH]$^+$=1166.7.

Example 4

4"-O-[3-(2-{2-[2-(3-Carboxy-7-chloro-1-cyclopropyl-4-oxo-1,4-dihydro-quinolin-6-ylamino)-ethoxy]-ethoxy}-ethylamino)-propyl]-azythromycin 11,12-cyclic carbonate

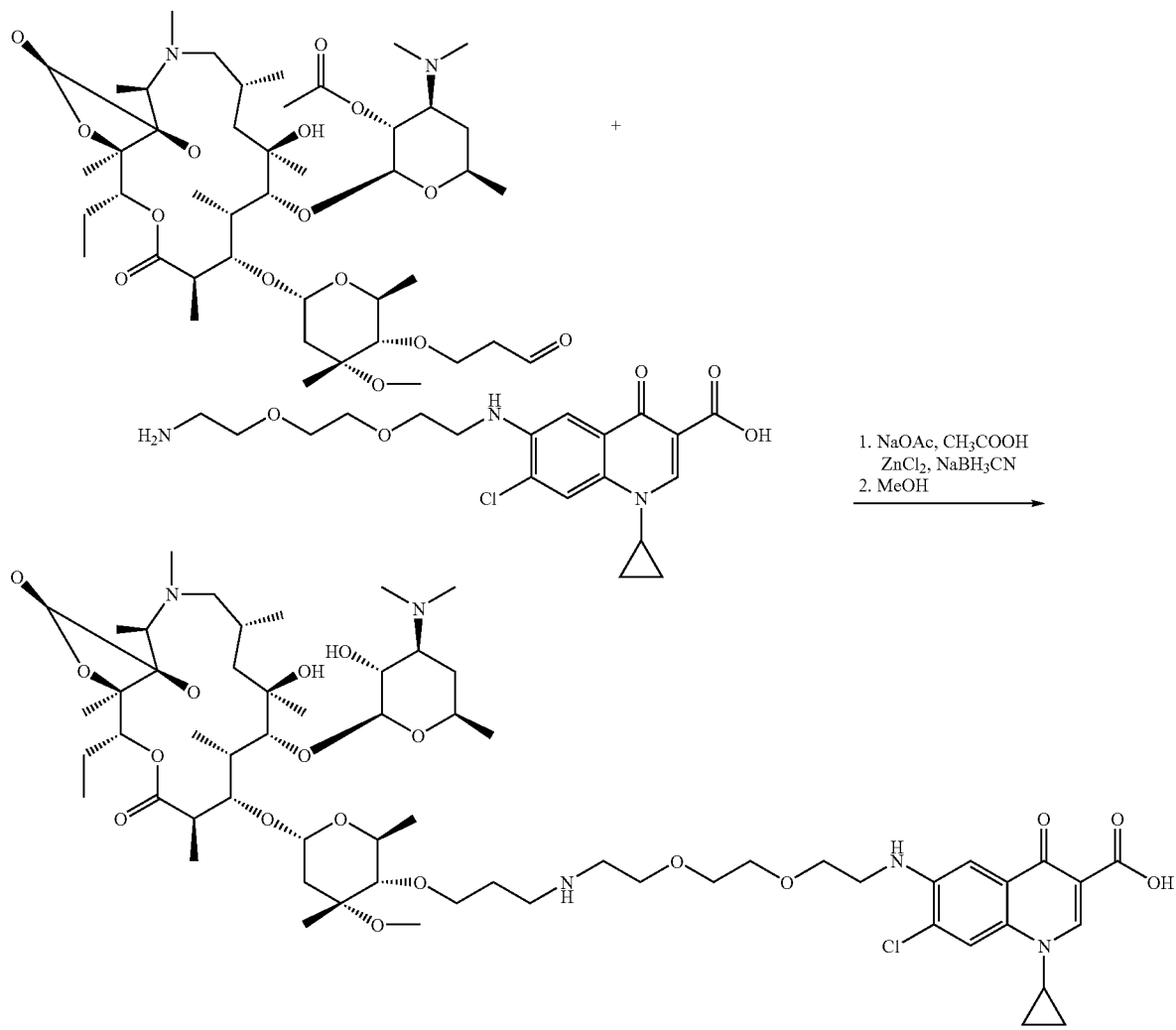

To a mixture of Intermediate 11A (0.047 g, 0.11 mmol), NaOAc (0.018 g, 0.22 mmol, 2 eq.) and acetic acid (0.22 mL, 3.9 mmol, 35 eq.) a dry solution of Intermediate 32 (0.1 g, 0.11 mmol) in MeOH/DCM=1/1 (4 mL) was added. To obtained mixture NaBH$_3$CN (0.014 g, 0.22 mmol) was added after 20 minutes. The reaction mixture was stirred at RT for 24 hours under N$_2$ atmosphere. Reaction mixture was filtered off and solvent evaporated under reduced pressure. To the residue EtOAc (20 mL) was added and extracted with aqueous NaHCO$_3$ (20 mL). Organic layer was dried over K$_2$CO$_3$ and evaporated under reduced pressure yielding 0.05 g of yellow solid to which MeOH (15 mL) was added and the reaction mixture was stirred at 45° C. over night, solvent was evaporated and product purified by column chromatography (sp column, 1 g, eluent DCM:MeOH:NH$_3$=90:9:0.5). Precipitation from EtOAc:n-hexane yielded 0.021 g of the title compound.

MS (ES+) m/z: [MH]$^+$=1224.9.

Example 5

4"-O-(3-{2-[3-(3-Carboxy-1-ethyl-4-oxo-1,4-dihydro-quinolin-6-yl)-propoxy]-ethylamnio}-propyl)-azithromycin

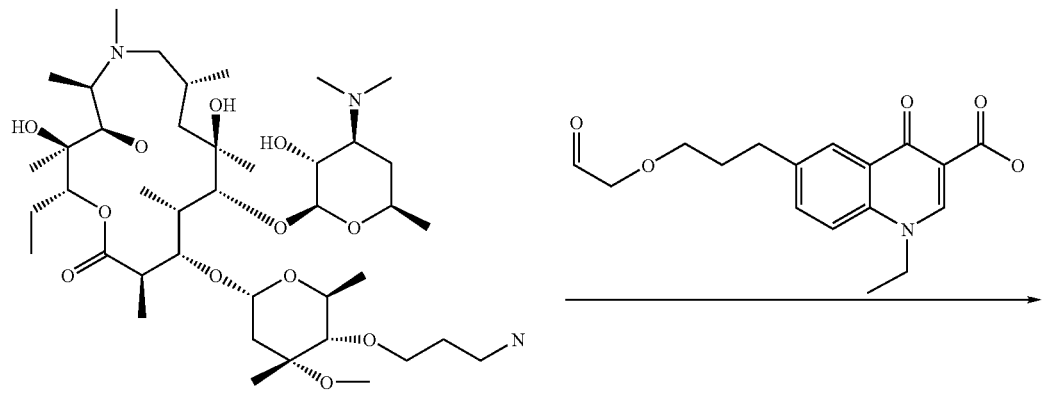

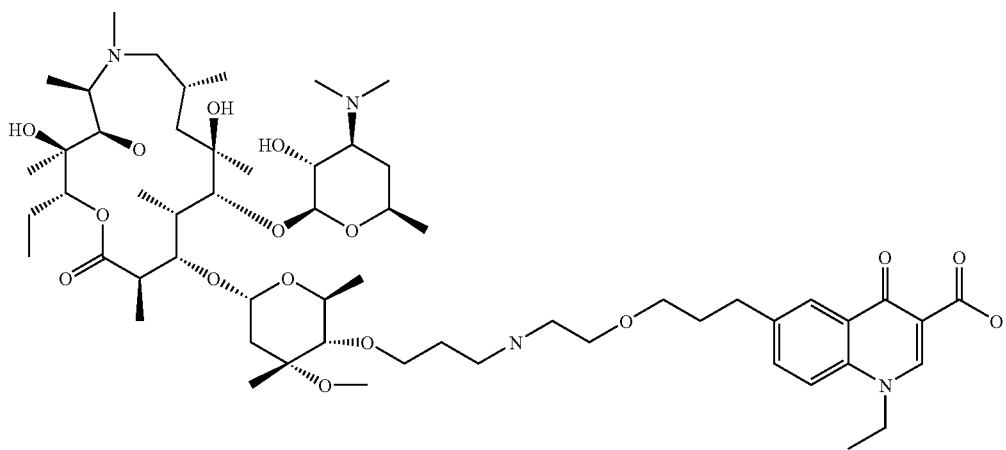

To the degassed solution of Intermediate 34 (0.08 g, 0.25 mmol) in MeOH (10 mL) Et$_3$N (10 μL, 0.072 mmol) and Intermediate 31 (0.2 g, 0.25 mmol) were added. After 2 hours NaBH$_4$ (20 mg, 0.53 mmol) was added. The reaction mixture was stirred for 12 hours at RT. Solvent was evaporated and to the residue DCM was added and extracted with water (2×20 mL). The layers were separated and organic layer was dried over K$_2$CO$_3$, solvent was evaporated in vacuum. Precipitation from EtOAc/n-hexane yielded crude title product (0.03 g), which after purification by column chromatography (eluent: DCM/MeOH/NH$_4$OH=90:15:1.5) yielded the title product (5 mg).

MS (ES+) m/z: [MH]$^+$=1107.47.

Example 6

4"-O-{2-[(2-{[3-(3-Carboxy-1-ethyl-4-oxo-1,4-dihydro-6-quinolinyl)-propyl]oxy}ethyl)-amino]ethyl}-6-O-methyl-erythromycin A

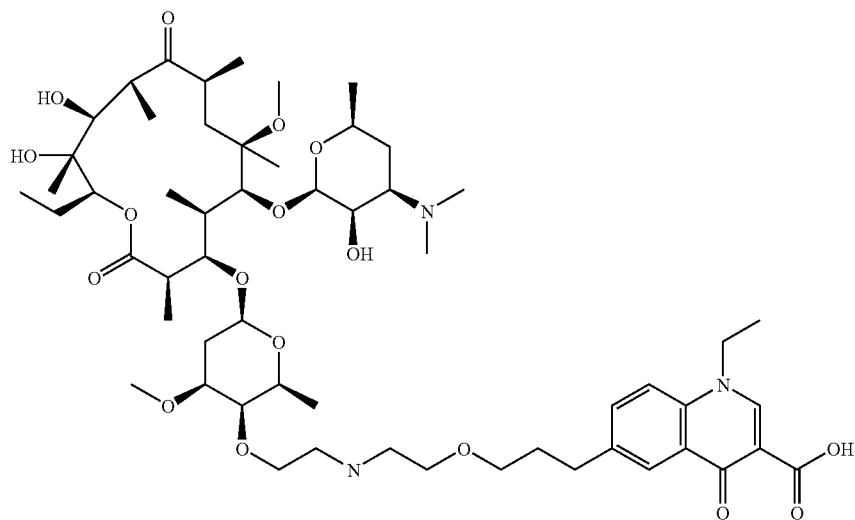

To Intermediate 36 (0.35 g) in methanol (3 mL) under argon 3A molecular sieves (0.5 g), acetic acid (0.1 mL) and sodium acetate (0.1 g) were added. To resulting mixture Intermediate 35 (0.416 g) in methanol (3 mL) and DMF (2 mL) were added. After stirring for 5 min, a methanolic solution of sodium cyanoborohydride (1M, 0.6 mL) was added. After 1 h the reaction was filtered, the solid washed with methanol and the combined filtrates evaporated to dryness. The residue was taken up in acetonitrile (25 mL) and formic acid (0.15 mL in 25 mL water) was added. The solution was stored at 4° C. for 16 h. The solution was evaporated to dryness and the residue was purified by preparative HPLC (acetonitrile/water/0.1% formic acid eluent) to give the title product (0.018 g).

MS (ES+) m/z: [MH]$^+$=1093.1.

Example 7

4"-O-(3-{2-[(E)-3-(3-Carboxy-1-ethyl-4-oxo-1,4-dihydro-quinolin-6-yl)-allyloxy]-ethoxy}-propyl)-11-O-methyl azithromycin

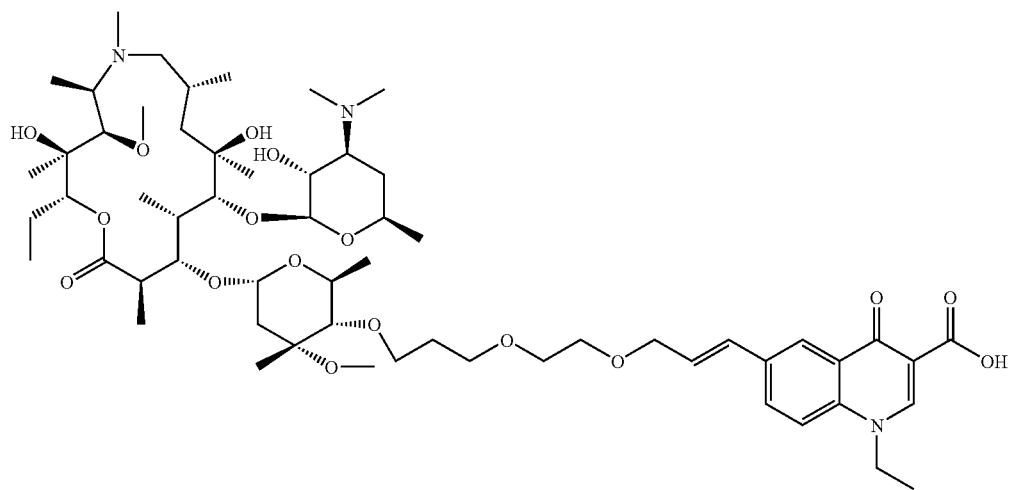

To a solution of Intermediate 39b (94 mg, 0.11 mmol) in DMF (3 ml) under $N_2$ atmosphere, Pd(OAc)$_2$ (0.01 g, 0.2 eq.) and TOTF (0.027 g, 0.4 eq.) were added. After 30 minutes of stirring Intermediate 33 (0.11 g, 0.31 mmol, 2.5 eq.) and Et$_3$N (0.124 ml, 0.09 mmol) were added, $N_2$ was removed and the reaction mixture was stirred at 65° C. for 1 hour and then at 75° C. for further 18 hours. After catalysts was filtered off, to filtrate isopropylacetate (20 ml) and aqueous NaHCO$_3$ (2×15 ml) were added, layers were separated and organic layer evaporated in vacuum to yield the crude title product. The crude product was first purified by column chromatography (SP column 10 g, eluent DCM:MeOH:NH$_3$=90:9:0.5) and than precipitated from EtOAc:n-hexane yielding the title compound (70 mg).

MS (ES) m/z: [MH]$^+$=1120.5.

Example 8

4"-O-(3-{2-[3-(3-Carboxy-1-ethyl-4-oxo-1,4-dihydro-quinolin-6-yl)-propoxy]-ethoxy}-propyl)-11-O-methyl azithromycin

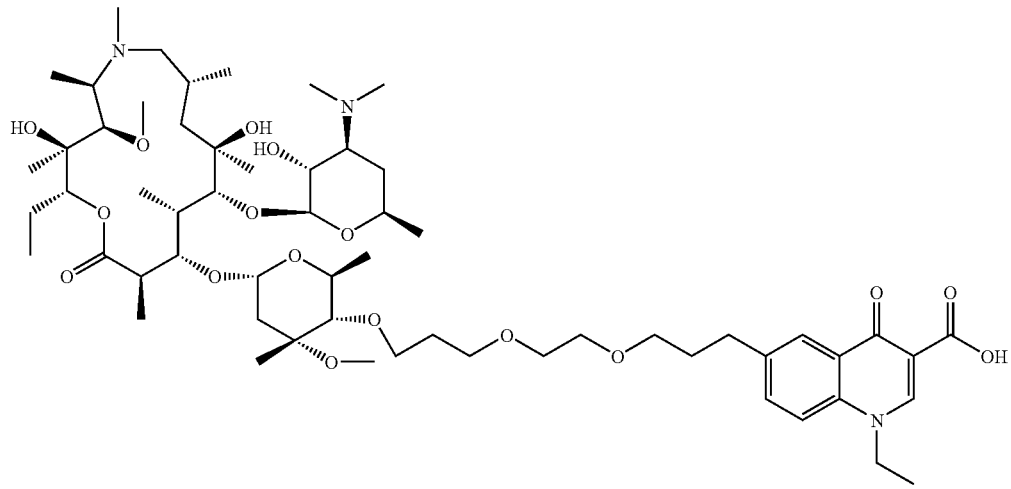

To a solution of Example 7 (0.6 g, 0.09 mmol) in DCM (5 ml) and EtOH (15 ml), 10% Pd/C (0.015 g) was added. The resulting mixture was hydrogenated in Parr apparatus at 3 bar under $H_2$ pressure for 5 hours. The catalyst was filtrated off and solvent evaporated in vacuum. Product was first purified by column chromatography (SP column 5 g, eluent: DCM:MeOH:$NH_3$=90:9:0.5) and then precipitated from EtOAc:n-hexane affording the title compound (21 mg).

MS (ES) m/z: [MH]$^+$=1122.5.

Example 9

4"-O-(3-{3-[3-(3-Carboxy-1-dimethylamino-4-oxo-1,4-dihydro-quinolin-6-yl)-propoxy]-propionylamino}-propyl)-6-O-methyl-erythromycin A

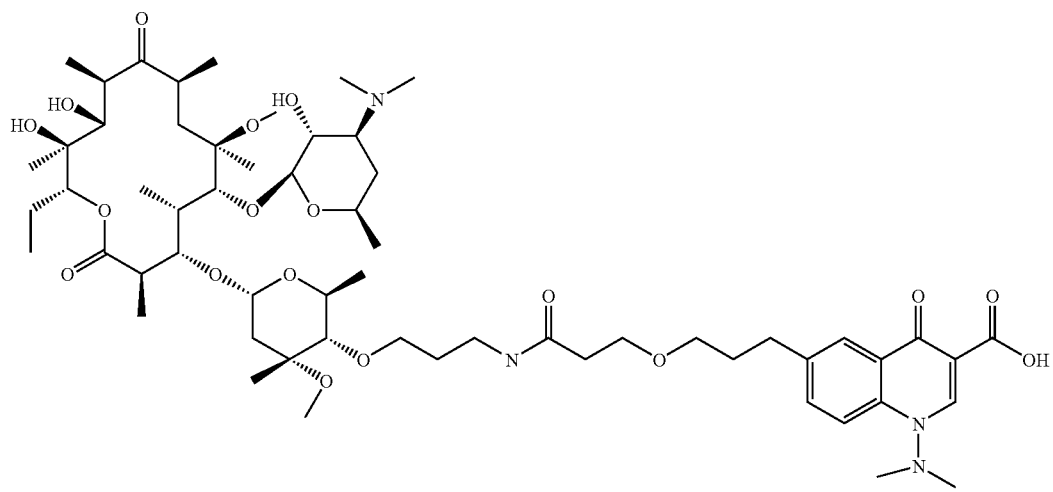

To the solution of Intermediate 43 (0.064 g, 0.08 mmol) in DCM (2 ml), Intermediate 44d (0.029 g, 0.08 mmol) dissolved in DCM (2 ml), TEA (0.112 ml, 0.8 mmol), HOBT (0.022 g, 0.16 mmol) and EDCxHCl (0.061 g, 0.32 mmol) were added. Reaction mixture was stirred at room temperature over night. To the reaction mixture water (10 ml) was added, layers were separated and the organic one was evaporated to give oily product (0.118 g) that was further purified by SPE technique using solvent system: $CHCl_3$/MeOH/$NH_4OH$=6:1:0.1 to afford the title product (11 mg).

MS (ES) m/z: $[MH]^+$=1149.5.

Example 10

4"-O-[3-(3-{2-[2-(3-carboxy-7-chloro-1-cyclopropyl-4-oxo-1,4-dihydro-quinolin-6-ylamino)-ethoxy]-ethoxy}-propionylamino)-propyl]-azithromycin-11,12-cyclic carbonate

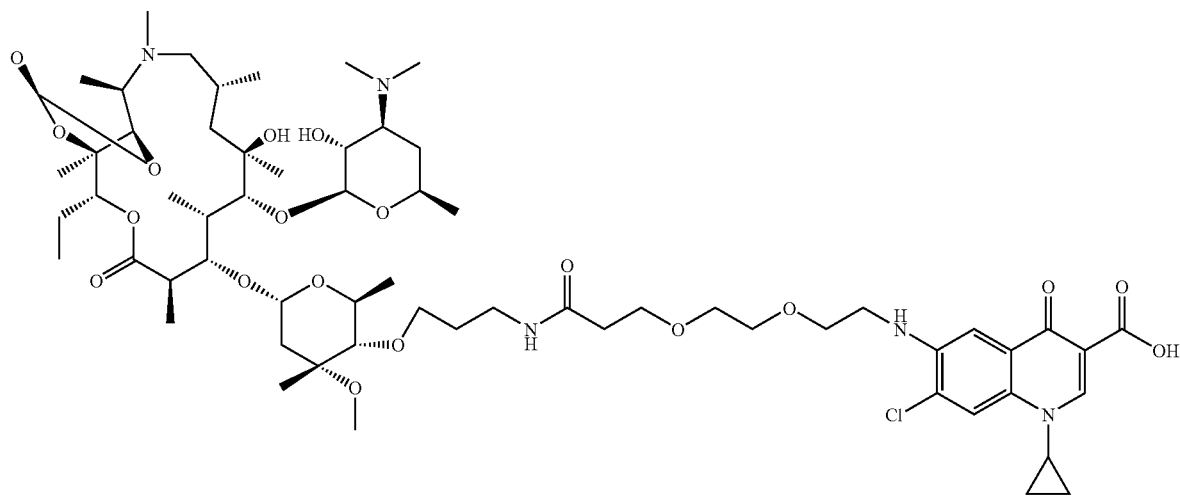

To a solution of Intermediate 30b (0.15 g, 0.17 mmol) in DCM (3 ml), Intermediate 7 (0.18 g, 0.41 mmol, 2.4 eq.) and DMAP (15 mg, 0.12 mmol, 0.7 eq.) were added. Then DCC (0.17 g, 0.82 mmol, 4.8 eq.) was added in portions during 30 minutes and stirred at room temperature for 3 hours. Reaction mixture was filtered, solvent evaporated in vacuum, isopropylacetate (15 ml) added and extracted with saturated aqueous $NaHCO_3$ (2×20 ml). To organic layer water (30 ml) was added and the pH was adjusted to 4.2. Layers were separated and to the water layer DCM (20 ml) was added and the pH was adjusted to 5. After layers separation to the organic one water (10 ml) was added and the pH was adjusted to 8. The combined organic layers at pH 8 were dried over $K_2CO_3$ and evaporated in vacuum. The crude residue was precipitated from EtOAc:n-hexane yielding 2'-O-acetyl protected title compound (0.15 g).

2'-O-Acetyl deprotection was performed in MeOH (20 ml) at 55° C. for 18 hours. Then MeOH was evaporated and the residue first purified by column chromatography (SP column, eluent: DCM:MeOH:$NH_3$=90:9:1.5) and than precipitated from EtOAc:n-hexane yielding the title compound (75 mg).

MS (ES) m/z: $[MH]^+$=1252.9.

Example 11

4"-O-[3-(3-{2-[2-(3-carboxy-7-chloro-1-cyclopropyl-4-oxo-1,4-dihydro-quinolin-6-ylamino)-ethoxy]-ethoxy}-propionylamino)-propyl]-azithromycin

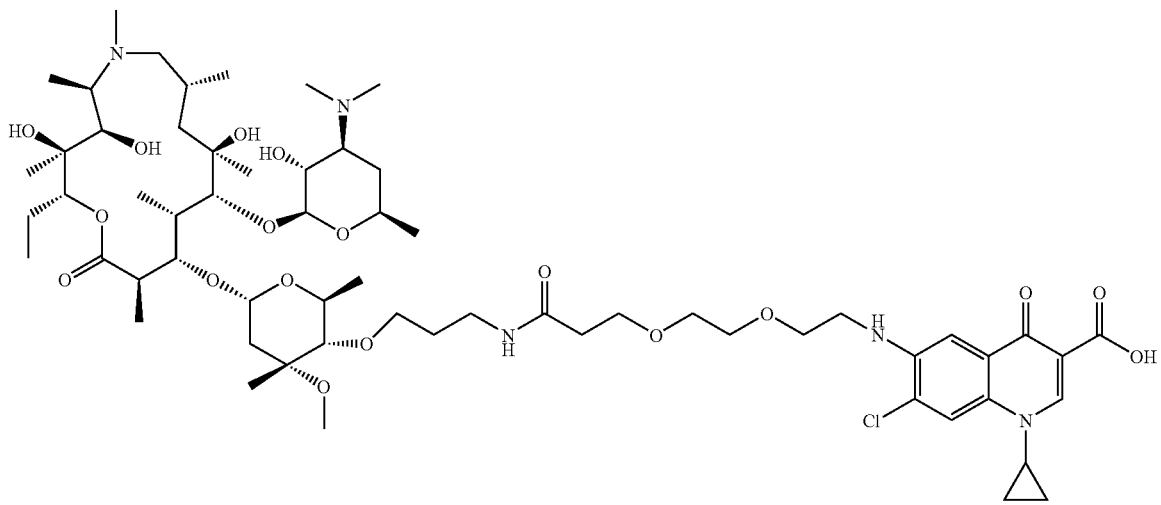

To a solution of Example 10 (0.05 g, 0.04 mmol) in MeOH (1 ml), solution of $K_2CO_3$ (0.08 g, 0.6 mmol, 15 eq.) in water (0.33 ml) was added and the reaction mixture was stirred at 55° C. for 1.5 hours. Then MeOH was evaporated, EtOAc (5 ml) added and extracted with saturated aqueous solution of $NaHCO_3$ (10 ml). Combined organic layers were dried over $K_2CO_3$, evaporated in vacuum and obtained residue precipitated from EtOAc:n-hexane yielding the title compound (39 mg).

MS (ES) m/z: $[MH]^+=1226.9$.

Example 12

4"-O-(3-{3-[3-(3-Carboxy-1-cyclopropyl-4-oxo-1,4-dihydro-quinolin-6-yl)-allyloxy]-propoxy}-propyl)-azithromycin

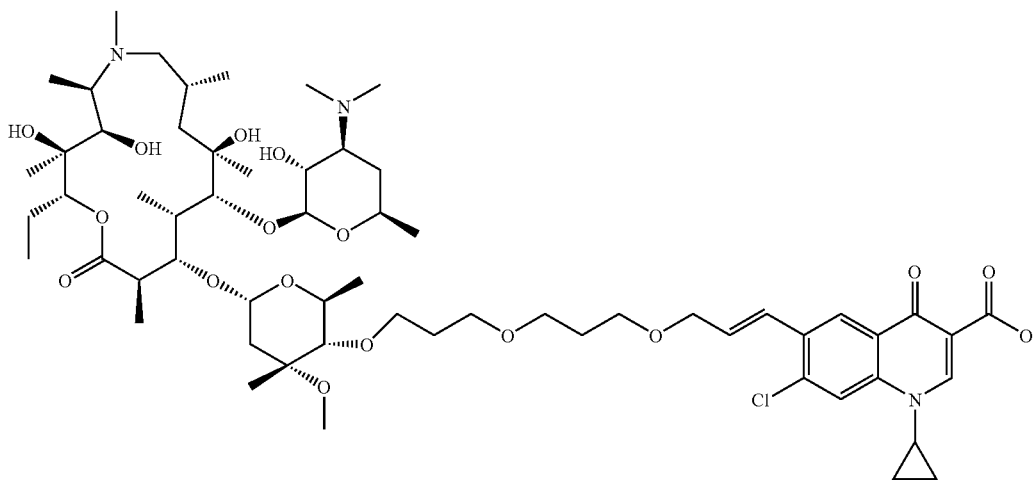

According to the procedure of Example 7 starting from Intermediate 45e (150 mg, 0.17 mmol) and 1-cyclopropyl-6-iodo-4-oxo-1,4-dihydro-quinoline-3-carboxylic acid (150 mg, 0.42 mmol, 2.5 eq.) the title compound was obtained (157 mg).

MS (ES) m/z: [MH]$^+$=1132.5.

Example 13

4"-O-(3-{3-[3-(3-Carboxy-1-cyclopropyl-4-oxo-1,4-dihydro-quinolin-6-yl)-propoxy]-propoxy}-propyl)-azithromycin phy (SP column 5 g, eluent: DCM:MeOH:NH$_3$=90:3:0.5) and then precipitated from EtOAc:n-hexane yielding the title compound (28 mg).

MS (ES) m/z: [MH]$^+$=1134.5.

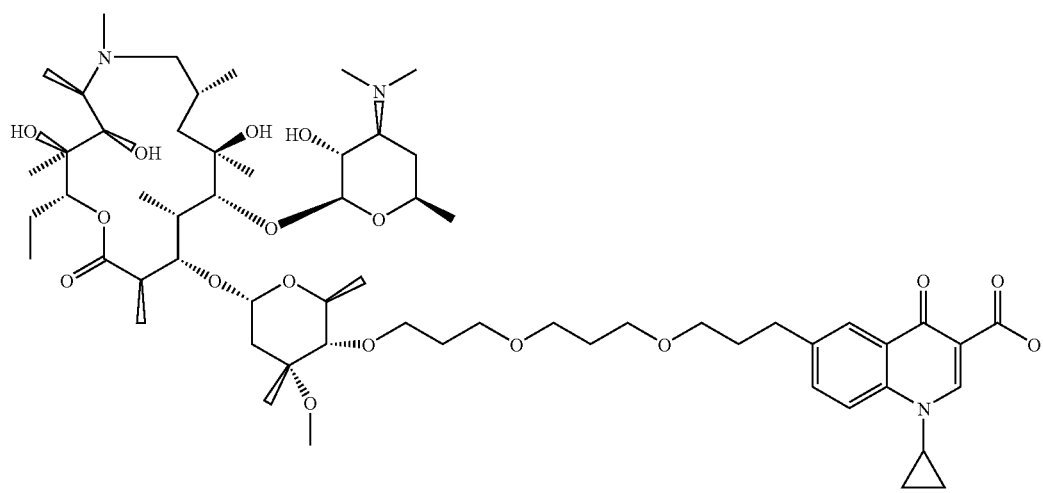

Compound of Example 12 (90 mg, 0.08 mmol) dissolved in MeOH (20 ml) and 10% Pd/C (45 mg) was added. Hidrogenation was performed at H$_2$-pressure of 5 bar for 15 hours. The catalyst was filtrated off and solvent evaporated in vacuum. Product was first purified by column chromatogra-

Example 14

4"-O-(3-{2-[3-(3-Carboxy-1-dimethylamino-4-oxo-1,4-dihydro-quinolin-6-yl)-allyloxy]-ethoxy}-propyl)-azithromycin

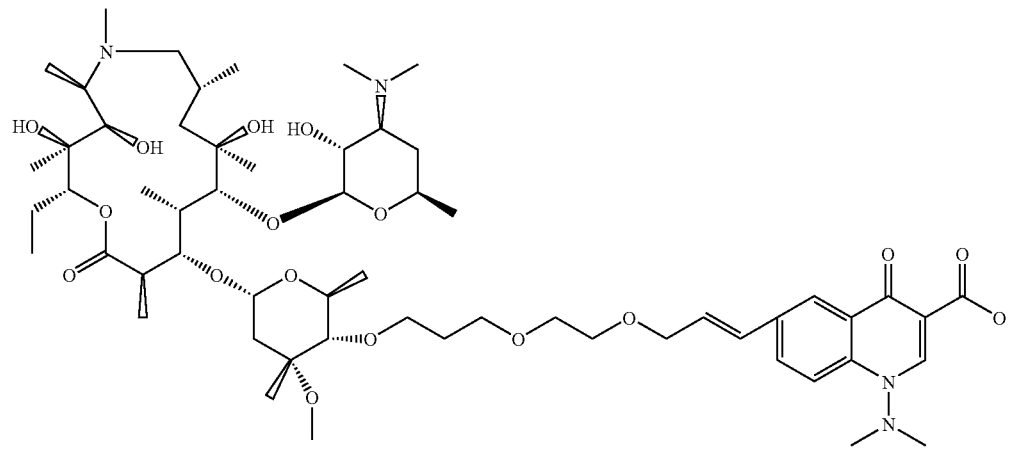

According to the procedure of Example 7 starting from Intermediate 46b (130 mg, 0.13 mmol) and 1-dimethylamino-6-iodo-4-oxo-1,4-dihydro-quinoline-3-carboxylic acid (130 mg, 0.36 mmol, 2.5 eq.) the title compound was obtained (70 mg).

MS (ES) m/z: [MH]$^+$=1121.7.

Example 15

4″-O-(3-{2-[3-(3-Carboxy-1-dimethylamino-4-oxo-1,4-dihydro-quinolin-6-yl)-propoxy]-ethoxy}-propyl)-azithromycin

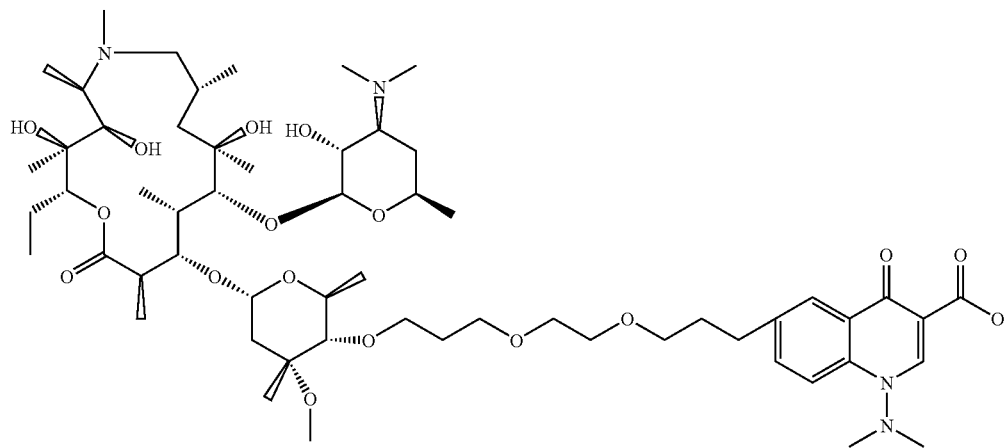

According to the procedure of Example 13 starting from Example 14 (70 mg, 0.06 mmol) the title compound was obtained (22 mg).

MS (ES) m/z: [MH]$^+$=1123.4.

Example 16

4″-O-(2-{2-[2-(3-Carboxy-6-fluoro-1-cyclopropyl-4-oxo-1,4-dihydro-quinolin-7-ylamino)-ethoxy]-ethylamino}-ethyl)-azithromycin 11,12-cyclic carbonate

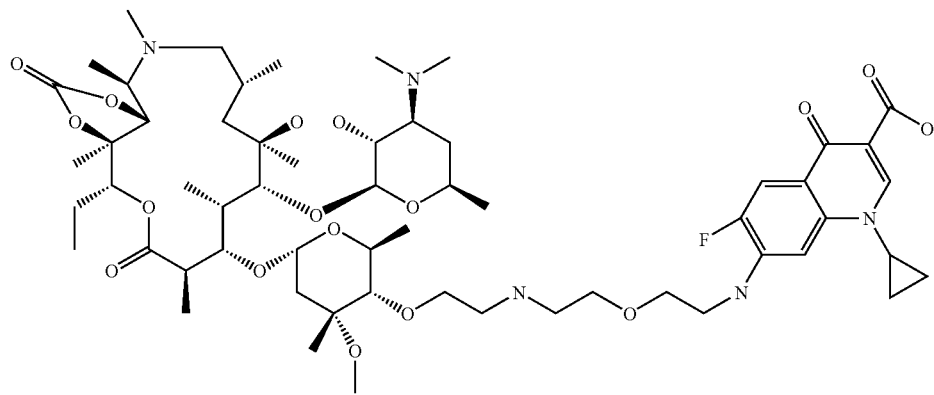

According to the procedure of Example 1a starting from Intermediate 17 (100 mg, 012 mmol) and Intermediate 29B (250.8 mg, 0.72 mmol) the title compound was obtained (91.3 mg).

MS (ES) m/z: [MH]$^+$=1150.5.

Example 17

4"-O-(2-{2-[2-(3-Carboxy-6-fluoro-1-cyclopropyl-4-oxo-1,4-dihydro-quinolin-7-ylamino)-ethoxy]-ethylamino}-ethyl)-azithromycin

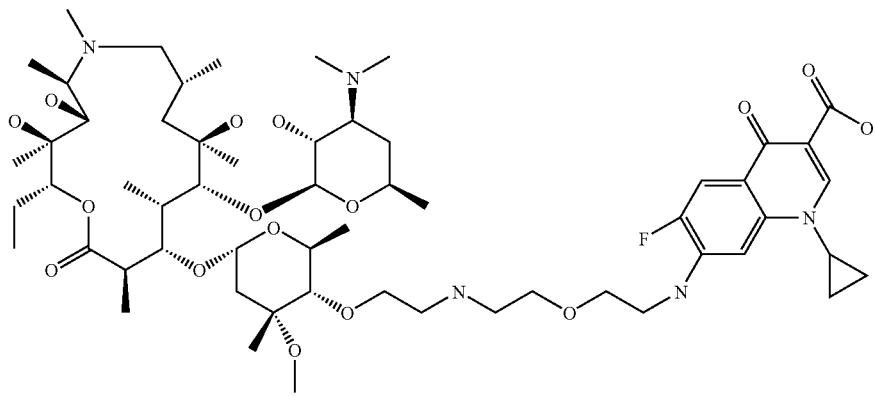

To Example 16 (9.6 mg, 0.008 mmol) dissolved in MeOH/H$_2$O (1:1, 0.2 ml) LiOH (1.5 mg, 0.06 mmol) was added and stirred at room temperature over night. Extraction with EtOAc afforded the title product (1.6 mg).

MS (ES) m/z: [MH]$^+$=1124.5.

Example 18

4"-O-{2-({2-[(2-{[2-(3-Carboxy-1-ethyl-4-oxo-1,4-dihydro-6-quinolinyl)ethyl]oxy}ethyl)oxy]ethyl}amino)ethyl}-6-O-methyl-erythromycin A formate A solution of Intermediate 48b (0.395 g) in methanol (10 mL) was added to 6-[2-({2-[(2-aminoethyl)oxy]ethyl}oxy)ethyl]-1-ethyl-4-oxo-1,4-dihydro-3-quinolinecarboxylic acid hydrochloride (0.231 g) (described in international patent application WO2005/108413). To this was then added sodium acetate (0.123 g) and 3 A molecular sieves (0.2 g), and the mixture was stirred for 10 min. Then sodium cyanoborohydride (0.063 g) and acetic acid (3 drops) were added and stirring continued for 3 h. The reaction was then filtered through Celite, and concentrated in vacuo. This residue was first purified by chromatography (silica gel, 3-18% (9:1 MeOH/0.880 ammonia) in dichloromethane eluent), then by mass directed automatic preparative HPLC. The product was dissolved in acetonitrile/water/0.880 ammonia and lyophilised to give the title compound as a white powder (0.242 g).

MS (ES+) m/z: [MH]$^+$1123.0.

Example 19

4''-O-{2-({2-[(2-{[2-(3-Carboxy-1-ethyl-4-oxo-1,4-dihydro-6-quinolinyl)ethyl]oxy}ethyl)oxy]ethyl}methylamino)ethyl}-6-O-methyl-erythromycin A

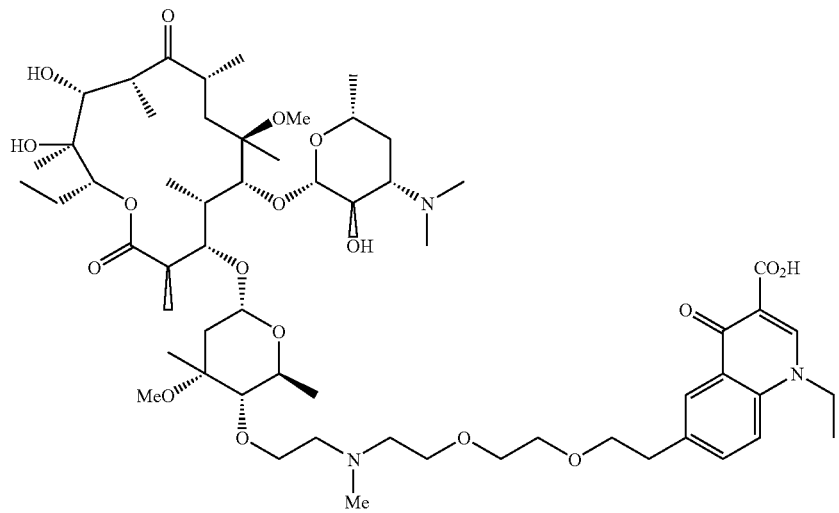

To a solution of Example 18 (0.21 g) in chloroform (10 mL) was added formic acid (0.027 mL) and formaldehyde (37% by weight in water) (0.03 mL). The mixture was heated to 60° C. for 0.5 h then concentrated in vacuo to give a residue which was purified by mass directed automatic preparative HPLC to give the product as the formic acid salt. This material was dissolved in acetonitrile/water/0.880 ammonia and lyophilised to give the title compound as a white powder (0.146 g).

MS (ES+) m/z: $[MH]^+=1136.9$.

Example 20

4''-O-(2-{[2-({3-[3-Carboxy-1-(dimethylamino)-4-oxo-1,4-dihydro-6-quinolinyl]propyl}amino)ethyl]sulfonyl}ethyl)-6-O-methyl erythromycin A 11,12-carbonate

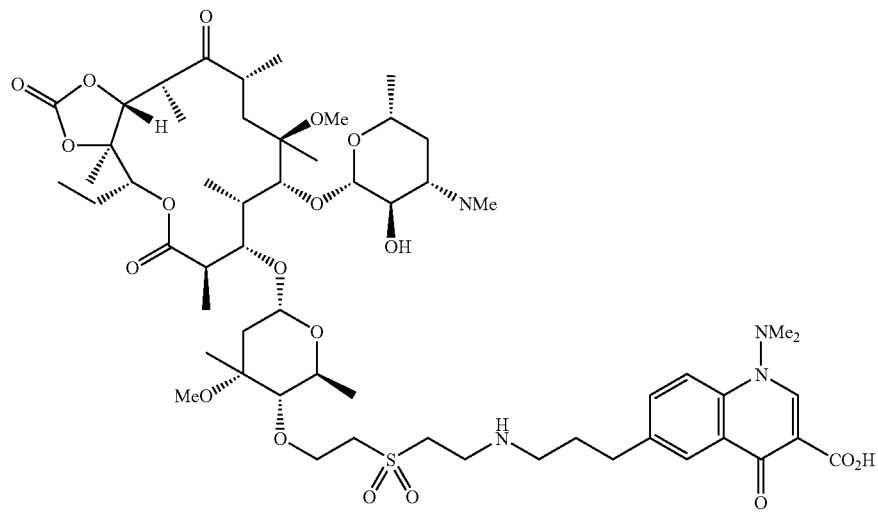

a) 2'-O-Acetyl-4"-O-2-(ethenylsulfonyl)ethyl-6-O-methyl erythromycin A 11,12-carbonate bis formate 2'-O-Acetyl-6-O-methyl erythromycin A 11,12-cyclic carbonate (0.8 g) in dimethyl sulfoxide (2 mL), acetonitrile (1.5 mL) and tert-butanol (0.1 mL) was cooled to 0° C. under argon and sodium hydride (60% in oil, 40 mg) added followed after 2 min by divinyl sulfone (0.20 mL). The reaction was allowed to warm to 20° C. and stirred for 16 h. Saturated aqueous sodium hydrogen carbonate was added and the mixture extracted with ethyl acetate. The organic layer was dried (sodium sulphate) and evaporated to a solid, 1.2 g. This was treated with warm acetonitrile (8 mL), and the insoluble solid removed by filtration. The filtrate was evaporated to a solid (0.6 g) which was suspended in acetonitrile (2.5 mL). The soluble material was purified by mass directed automatic preparative HPLC to give the title compound (0.044 g).

MS (ES+) m/z: [MH]$^+$=934.8.

b) 2'-O-Acetyl-4"-O-(2-{[2-({3-[3-carboxy-1-(dimethylamino)-4-oxo-1,4-dihydro-6-quinolinyl]propyl}amino)ethyl]sulfonyl}ethyl)-6-O-methyl erythromycin A 11,12-carbonate Example 20, step a (0.044 g) in dimethyl sulfoxide (0.6 mL), triethylamine (0.022 mL) and water (½ drop) was treated with Intermediate 47c (0.03 g). The reaction was heated to 40° C. for 45 min and 45° C. for 135 min. The crude product was purified by mass directed automatic preparative HPLC and freeze dried from water (6 mL) and 0.880 ammonia (0.2 mL) to give the title compound (0.015 g).

MS (ES+) m/z: [MH]$^+$=1224.0.

c) 4"-O-(2-{[2-({3-[3-Carboxy-1-(dimethylamino)-4-oxo-1,4-dihydro-6-quinolinyl]propyl}amino)ethyl]sulfonyl}ethyl)-6-O-methyl erythromycin A 11,12-carbonate Example 20, step b (0.015 g) in methanol (5 mL) was heated at 45° C. for 17 h, to give, after evaporation to dryness, the title compound as an off white foam; 0.014 g.

MS (ES+) m/z: [MH]$^+$=1181.9.

Example 21

4"-O-(3-{2-[3-(3-Carboxy-1-ethyl-4-oxo-1,4-dihydro-quinolin-6-yl)-allyloxy]-ethoxy}-propyl)-azithromycin

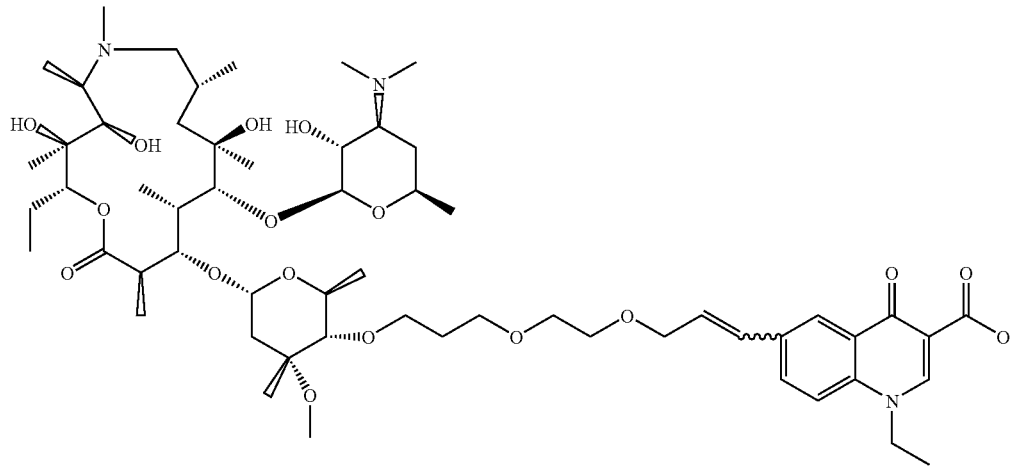

To a solution of Intermediate 49b (62 mg, 0.07 mmol) in DMF (2 ml), Pd(OAc)$_2$ (3.1 mg, 0.014 mmol, 0.2 equiv.) and tri-o-tolyl phosphine (8.5 mg, 0.028 mmol, 0.4 equiv.) were added under N$_2$ atmosphere. After 45 minutes 6-iodo-1-ethyl-4-oxo-1,4-dihydro-quinoline-3-carboxylic acid (48 mg, 0.14 mmol, 2 eq.) and Et$_3$N (0.038 ml, 0.28 mmol, 4 eq.) were added. N$_2$ atmosphere was removed and the reaction mixture was further stirred at 65° C. for 48 hours. Catalysts were filtered off, EtOAc (10 ml) and aqueous NaHCO$_3$ (3×10 ml) were added. Organic layer was acidified to pH 3 and extracted with water (2×20 ml). pH of combined water layers was adjusted to 10 and extracted with EtOAc (20 ml). Organic layer was evaporated in vacuum. Precipitation from EtOAc/n-hexane yielded the title product (50 mg).

MS (ES) m/z: [MH]$^+$=1106.4 (92.5%)

Example 22

4"-O-(3-{2-[3-(3-Carboxy-1-ethyl-4-oxo-1,4-dihydro-quinolin-6-yl)-propoxy]-ethoxy}-propyl)-azithromycin

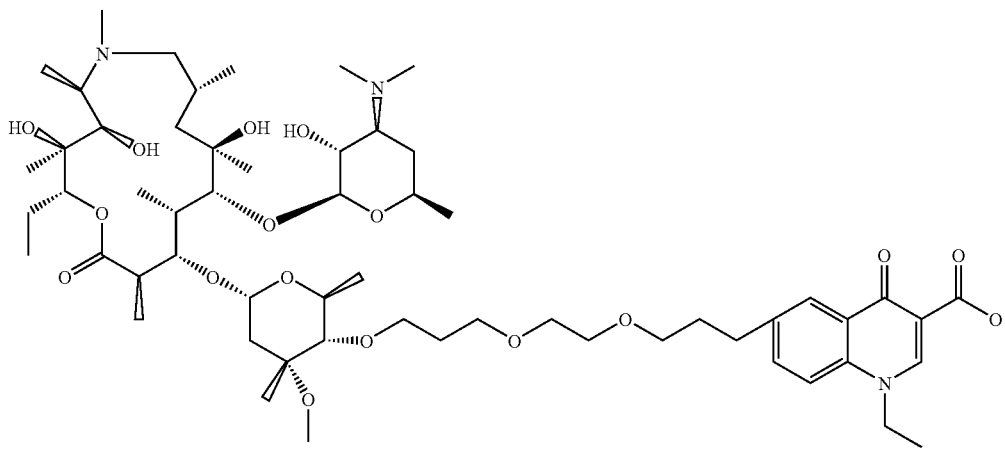

According to the procedure of Example 13 starting from Example 21 (44 mg, 0.04 mmol) the crude title compound was obtained. Precipitation from EtOAc/n-hexane yielded the title compound (35 mg).

MS (ES) m/z: [MH]$^+$=1108.4 (92%).

Example 23

4"-O-(3-{3-[2-(3-Carboxy-7-chloro-1-cyclopropyl-4-oxo-1,4-dihydro-quinolin-6-ylamino)-ethoxy]-propionylamino}-propyl)-6-O-methyl erythromycin A 11,12-cyclic carbamate

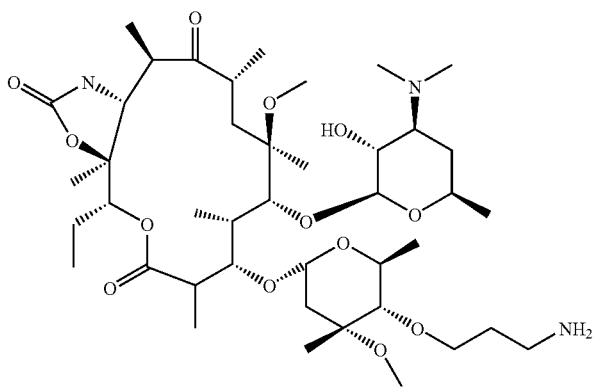

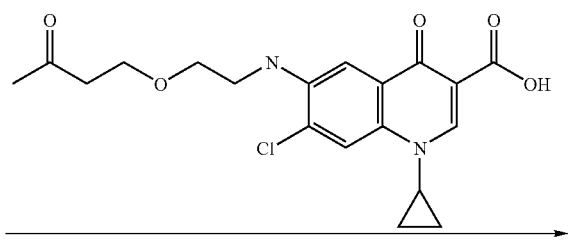

-continued

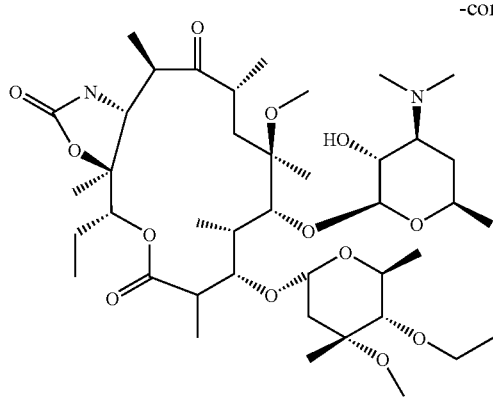

To a suspension of 6-[2-(2-carboxy-ethoxy)-ethylamino]-7-chloro-1-cyclopropyl-4-oxo-1,4-dihydro-quinoline-3-carboxylic acid (described in international publication WO 2004/101585A1, Intermediate 17) (24 mg, 61.4 μmol) in dry DCM (0.5 ml), TEA (86 μl, 10 eq) and HOBT (17 mg, 2 eq) were added followed by addition of Intermediate 50g (51 mg, 1 eq) in DCM (1 ml). Then EDC×HCl (47 mg, 4 eq) was added and the mixture was stirred at room temperature overnight. To this mixture, water (2 ml) was added, and the organic layer was separated and evaporated. The crude residue (73 mg) was dissolved in DCM (0.5 ml) and DIPE (4 ml) was added. The resulting precipitate was filtered off. Purification was done by preparative HPLC using a gradient system for elution: (0.1% HCOOH in $H_2O/CH_3CN$) in which $HCOOH:CH_3CN$ was changed from 95:5 to 50:50 giving the title compound (3.7 mg).

MS (ES) m/z: $[MH]^+$=1206.6.

Biological Data

The MIC (μg/ml) of test compounds against various organisms was determined including: *Staphylococcus aureus, Streptococcus pneumoniae, Streptococcus pyogenes, Enterococcus faecalis, Haemophylus influenzae, Moraxella catarrhalis.*

Examples 2-6, 9-13, 15-16 and 18-20 have an MIC≦0.125 μg/ml against sensitive *S. pneumoniae* and sensitive *S. pyogenes* and an MIC≦1 μg/ml against *E. faecalis.*

Examples 4-6, 8-10, 12, 13, 15, 18-20 have an MIC≦1 μg/ml against *M. catarrhalis.*

Examples 2-6, 8, 10-13, 15, 16, 18-20 have an MIC≦0.25 μg/ml against erythromycin resistant strain of *Streptococcus pneumoniae.*

Examples 2-6, 8-13, 15, 16, 18-20 have an MIC≦0.25 μg/ml against erythromycin resistant strain of *Streptococcus pyogenes.*

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. A compound of formula (I)

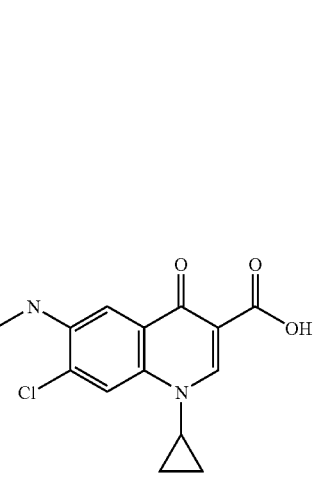

wherein

A is a bivalent radical selected from the group consisting of —C(O)—, —C(O)NH—, —NHC(O)—, —N($R^7$)—$CH_2$—, —$CH_2$—N($R^7$)—, —CH(N$R^8R^9$)— and —C(=N$R^{10}$)—;

$R^1$ is —O($CH_2$)$_d$X$R^{11}$;

$R^2$ is hydrogen or a hydroxyl protecting group;

$R^3$ is hydrogen, $C_{1-4}$alkyl, or $C_{3-6}$alkenyl optionally substituted by 9 to 10 membered fused bicyclic heteroaryl;

$R^4$ is hydroxyl, $C_{2-6}$alkenyloxy optionally substituted by 9 to 10 membered fused bicyclic heteroaryl, or $C_{1-6}$alkoxy optionally substituted by $C_{1-6}$alkoxy or —O($CH_2$)$_e$N$R^7R^{12}$;

$R^5$ is hydroxyl, or $R^4$ and $R^5$ taken together with the intervening atoms form a cyclic group having the following structure:

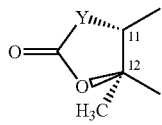

wherein Y is a bivalent radical selected from —CH$_2$—, —CH(CN)—, —O—, —N(R$^{13}$)— and —CH(SR$^{13}$)—;

R$^6$ is hydrogen or fluorine;

R$^7$ is hydrogen or C$_{1-6}$alkyl;

R$^8$ and R$^9$ are each independently hydrogen, C$_{1-6}$alkyl, —C(=NR$^{10}$)NR$^{14}$R$^{15}$ or —C(O)R$^{14}$, or R$^8$ and R$^9$ together form =CH(CR$^{14}$R$^{15}$)$_f$aryl, =CH(CR$^{14}$R$^{15}$)$_f$heterocyclyl, =CR$^{14}$R$^{15}$ or =C(R$^{14}$)C(O)OR$^{14}$, wherein the alkyl, aryl and heterocyclyl groups are optionally substituted by up to three groups independently selected from R$^{16}$;

R$^{10}$ is —OR$^{17}$, C$_{1-6}$alkyl, —(CH$_2$)$_g$aryl, —(CH$_2$)$_g$heterocyclyl or —(CH$_2$)$_h$O(CH$_2$)$_i$OR$^7$, wherein each R$^{10}$ group is optionally substituted by up to three groups independently selected from the group consisting of R$^{16}$;

R$^{11}$ is a heterocyclic group having the following structure:

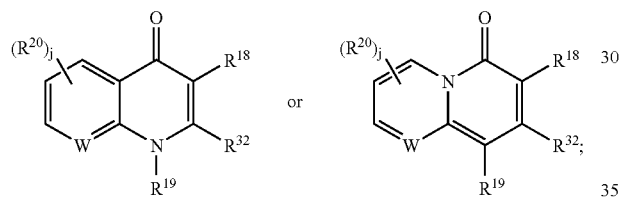

R$^{12}$ is hydrogen or C$_{1-6}$alkyl;

R$^{13}$ is hydrogen or C$_{1-4}$alkyl substituted by a group selected from the group consisting of optionally substituted phenyl, optionally substituted 5 or 6 membered heteroaryl and optionally substituted 9 to 10 membered fused bicyclic heteroaryl;

R$^{14}$ and R$^{15}$ are each independently hydrogen or C$_{1-6}$alkyl;

R$^{16}$ is halogen, cyano, nitro, trifluoromethyl, azido, —C(O)R$^{21}$, —C(O)OR$^{21}$, —OC(O)R$^{21}$, —OC(O)OR$^{21}$, —NR$^{22}$C(O)R$^{23}$, —C(O)NR$^{22}$R$^{23}$, —NR$^{22}$R$^{23}$, hydroxyl, C$_{1-6}$alkyl, —S(O)$_k$C$_{1-6}$alkyl, C$_{1-6}$alkoxy, —(CH$_2$)$_m$aryl or —(CH$_2$)$_m$heteroaryl, wherein the alkoxy group is optionally substituted by up to three groups independently selected from the group consisting of —NR$^{14}$R$^{15}$, halogen and —OR$^{14}$, and the aryl and heteroaryl groups are optionally substituted by up to five groups independently selected from the group consisting of halogen, cyano, nitro, trifluoromethyl, azido, —C(O)R$^{24}$, —C(O)OR$^{24}$, —OC(O)OR$^{24}$, —NR$^{25}$C(O)R$^{26}$, —C(O)NR$^{25}$R$^{26}$, —NR$^{25}$R$^{26}$, hydroxyl, C$_{1-6}$alkyl and C$_{1-6}$alkoxy;

R$^{17}$ is hydrogen, C$_{1-6}$alkyl, C$_{3-7}$cycloalkyl, C$_{3-6}$alkenyl or a 5 or 6 membered heterocyclic group, wherein the alkyl, cycloalkyl, alkenyl and heterocyclic groups are optionally substituted by up to three substituents independently selected from the group consisting of optionally substituted 5 or 6 membered heterocyclic group, optionally substituted 5 or 6 membered heteroaryl, —OR$^{27}$, —S(O)$_n$R$^{27}$, —NR$^{27}$R$^{28}$, —CONR$^{27}$R$^{28}$, halogen and cyano;

R$^{18}$ is hydrogen, —C(O)OR$^{29}$, —C(O)NHR$^{29}$, —C(O)CH$_2$NO$_2$, or —C(O)CH$_2$SO$_2$R$^7$;

R$^{19}$ is hydrogen; C$_{1-4}$alkyl optionally substituted by hydroxyl, cyano, C$_{1-4}$alkoxy, NH$_2$, —NH(C$_{1-4}$alkyl) or —N(C$_{1-4}$alkyl)$_2$; C$_{2-4}$alkenyl optionally substituted by hydroxyl, cyano, C$_{1-4}$alkoxy, NH$_2$, —NH(C$_{1-4}$alkyl) or —N(C$_{1-4}$alkyl)$_2$; C$_{1-4}$alkoxy; C$_{3-7}$cycloalkyl; —NH$_2$; —NH(C$_{1-4}$alkyl); —N(C$_{1-4}$alkyl)$_2$; (C$_{1-4}$alkyl)OC(O)N(C$_{1-4}$alkyl); or optionally substituted phenyl or benzyl;

R$^{20}$ is halogen, C$_{1-4}$alkyl, C$_{1-4}$thioalkyl, C$_{1-4}$alkoxy, —NH$_2$, —NH(C$_{1-4}$alkyl) or —N(C$_{1-4}$alkyl)$_2$;

R$^{21}$ is hydrogen, C$_{1-10}$alkyl, —(CH$_2$)$_p$aryl or —(CH$_2$)$_p$heteroaryl;

R$^{22}$ and R$^{23}$ are each independently hydrogen, —OR$^{14}$, C$_{1-6}$alkyl, —(CH$_2$)$_q$aryl or —(CH$_2$)$_q$heterocyclyl;

R$^{24}$ is hydrogen, C$_{1-10}$alkyl, —(CH$_2$)$_r$aryl or —(CH$_2$)$_r$heteroaryl;

R$^{25}$ and R$^{26}$ are each independently hydrogen, —OR$^{14}$, C$_{1-6}$alkyl, —(CH$_2$)$_s$aryl or —(CH$_2$)$_s$heterocyclyl;

R$^{27}$ and R$^{28}$ are each independently hydrogen, C$_{1-4}$alkyl or C$_{1-4}$alkoxyC$_{1-4}$alkyl;

R$^{29}$ is hydrogen or C$_{1-6}$alkyl optionally substituted by up to three groups independently selected from the group consisting of halogen, C$_{1-4}$alkoxy, —OC(O)C$_{1-6}$alkyl and —OC(O)OC$_{1-6}$alkyl, or —(CH$_2$)$_q$heterocyclyl, —(CH$_2$)$_q$heteroaryl, —(CH$_2$)$_q$aryl, —(CH$_2$)$_q$C$_{3-7}$cycloalkyl;

R$^{30}$ is hydrogen, C$_{1-4}$alkyl, C$_{3-7}$cycloalkyl, optionally substituted phenyl or benzyl, acetyl or benzoyl;

R$^{31}$ is hydrogen or R$^{20}$, or R$^{31}$ and R$^{19}$ are linked to form the bivalent radical selected from the group consisting of —O(CH$_2$)$_2$—, —(CH$_2$)$_t$—, —NR$^7$(CH$_2$)$_a$—, —OCH$_2$NR$^7$—, —SCH$_2$NR$^7$—, —CH$_2$NR$^7$CH$^2$—, —CH$_2$OCH$_2$—, —CH$_2$SCH$_2$, and —(CH$_2$)$_a$NR$^7$—;

R$^{32}$ is hydrogen, or R$^{32}$ and R$^{19}$ are linked to form the bivalent radical selected from the group consisting of —S(CH$_2$)$_b$—, —N(R$^7$)(CH$_2$)$_b$—, and —O(CH$_2$)$_b$—;

R$^{33}$ is C$_{1-8}$alkyl, C$_{2-6}$alkenyl or C$_{2-6}$alkynyl;

X is —U(CH$_2$)$_v$B(CH$_2$)$_v$D-, —U(CH$_2$)$_v$B—R$^{33}$, —U(CH$_2$)$_v$B(CH$_2$)$_v$D(CH$_2$)$_v$E-, or —U(CH$_2$)$_v$B(CH$_2$)$_v$D-R$^{33}$— or X is a group selected from the group consisting of:

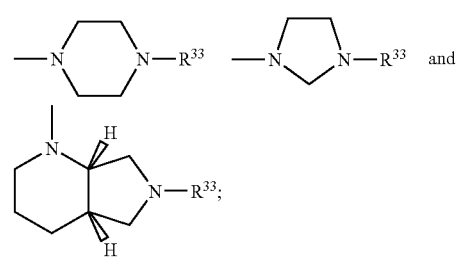

U, B, D and E are independently divalent radicals selected from —N(R$^{30}$)—, —O—, —S(O)$_z$—, —N(R$^{30}$)C(O)—, —C(O)N(R$^{30}$)— and —N[C(O)R$^{30}$]—;

W is —C(R$^{31}$)— or —N—;

a is 1 or 2 b is an integer from 1 to 3;

d is an integer from 2 to 6;

e is an integer from 2 to 4;

f, g, h, m, p, q, r and s are each independently integers from 0 to 4;

i is an integer from 1 to 6;

j, k, n and z are each independently integers from 0 to 2;

t is 2 or 3;

v is an integer independently selected for each occurrence from 1 to 8;

or a pharmaceutically acceptable salt thereof.

2. The compound according to claim 1, or a pharmaceutically acceptable salt thereof, wherein A is —C(O)— or —N($R^7$)—$CH_2$—.

3. The compound according to claim 1, or a pharmaceutically acceptable salt thereof, wherein d is 2 or 3.

4. The compound according to claim 1, or a pharmaceutically acceptable salt thereof, wherein v is 2 or 3.

5. The compound according to claim 1 wherein $R^{11}$ is a heterocyclic group having the following structure:

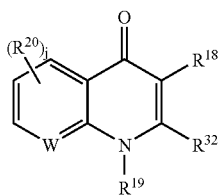

wherein the heterocyclic is linked in the 6 or 7 position, $R^{18}$ is hydrogen, —C(O)$OR^{29}$, —C(O)$NHR^{29}$, —C(O)$CH_2NO_2$, or —C(O)$CH_2SO_2R^7$;

$R^{19}$ is hydrogen; $C_{1-4}$alkyl; $C_{3-7}$cycloalkyl, —$NH_2$, —NH($C_{1-4}$alkyl) or —N($C_{1-4}$alkyl)$_2$;

$R^{20}$ is halogen;

$R^{29}$ is hydrogen or $C_{1-6}$alky;

$R^{32}$ is hydrogen;

W is —CH or —N—;

or a pharmaceutically acceptable salt thereof.

6. The compound according to claim 1, or a pharmaceutically acceptable salt thereof, wherein $R^{18}$ is hydrogen, —C(O)OH, —C(O)$NH_2$, —C(O)$CH_2NO_2$, or —C(O)$CH_2SO_2H$.

7. The compound according to claim 6, or a pharmaceutically acceptable salt thereof, wherein $R^{18}$ —C(O)OH.

8. The compound according to claim 1, or a pharmaceutically acceptable salt thereof, wherein X is —N($R^{30}$)($CH_2$)$_v$O($CH_2$)$_v$O—$R^{33}$—; —N($R^{30}$)($CH_2$)$_v$O($CH_2$)$_v$N($R^{30}$)—; —N($R^{30}$)($CH_2$)$_v$O($CH_2$)$_v$O($CH_2$)$_v$N($R^{30}$)—; —O($CH_2$)$_v$O$R^{33}$—; —N($R^{30}$)($CH_2$)$_v$O—$R^{33}$—; —NHC(O)($CH_2$)$_v$O—$R^{33}$—; —NHC(O)($CH_2$)$_v$ O($CH_2$)$_v$O($CH_2$)$_v$N($R^{30}$)—; or $SO_2$($CH_2$)$_v$N($R^{30}$)—$R^{33}$—, $R^{30}$ is H or $CH_3$, and $R^{33}$ is $C_{1-8}$alkyl or $C_{2-6}$alkenyl.

9. The compound according to claim 8, or a pharmaceutically acceptable salt thereof wherein $R^{33}$ is —($CH_2$)—, —($CH_2$)$_2$—, ($CH_2$)$_3$—, or —$CH_2CH$=$CH$— and each v is independently 1, 2, or 3.

10. The compound according to claim 1, or a pharmaceutically acceptable salt thereof, wherein $R^{11}$ is a heterocyclic group of the following formula:

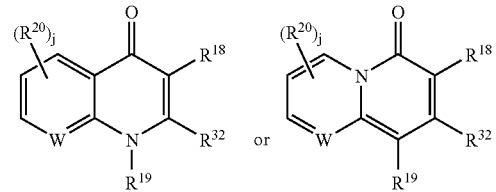

wherein the heterocyclic is linked in the 6 or 7 position and j, $R^{18}$, $R^{19}$, $R^{20}$ and $R^{32}$ are as defined in claim 1.

11. A compound selected from:

4"-O-[2-(2-{2-[2-(3-Carboxy-7-chloro-1-cyclopropyl-4-oxo-1,4-dihydro-quinolin-6-ylamino)-ethoxy]-ethoxy}-ethylamino)-ethyl]-azithromycin 11,12-cyclic carbonate;

4"-O-(2-{2-[2-(3-Carboxy-7-chloro-1-cyclopropyl-4-oxo-1,4-dihydro-quinolin-6-ylamino)-ethoxy]-ethylamino}-ethyl)-azithromycin 11,12-cyclic carbonate;

4"-O-[3-(2-{2-[2-(3-Carboxy-7-chloro-1-cyclopropyl-4-oxo-1,4-dihydro-quinolin-6-ylamino)-ethoxy]-ethoxy}-ethylamino)-propyl]-azythromycin 11,12-cyclic carbonate;

4"-O-(3-{2-[3-(3-Carboxy-1-ethyl-4-oxo-1,4-dihydro-quinolin-6-yl)-propoxy]-ethylamino}-propyl)-azithromycin;

4"-O-{2-[(2-{[3-(3-Carboxy-1-ethyl-4-oxo-1,4-dihydro-6-quinolinyl)-propyl]oxy}ethyl)-amino]ethyl}-6-O-methyl-erythromycin A;

4"-O-(3-{2-[(E)-3-(3-Carboxy-1-ethyl-4-oxo-1,4-dihydro-quinolin-6-yl)-allyloxy]-ethoxy}-propyl)-11-O-methyl azithromycin;

4"-O-(3-{2-[3-(3-Carboxy-1-ethyl-4-oxo-1,4-dihydro-quinolin-6-yl)-propoxy]-ethoxy}-propyl)-11-O-methyl azithromycin;

4"-O-(3-{3-[3-(3-Carboxy-1-dimethylamino-4-oxo-1,4-dihydro-quinolin-6-yl)-propoxy]-propionylamino}-propyl)-6-O-methyl-erythromycin A;

4"-O-[3-(3-{2-[2-(3-carboxy-7-chloro-1-cyclopropyl-4-oxo-1,4-dihydro-quinolin-6-ylamino)-ethoxy]-ethoxy}-propionylamino)-propyl]-azithromycin-11,12-cyclic carbonate;

4"-O-[3-(3-{2-[2-(3-carboxy-7-chloro-1-cyclopropyl-4-oxo-1,4-dihydro-quinolin-6-ylamino)-ethoxy]-ethoxy}-propionylamino)-propyl]-azithromycin;

4"-O-(3-{3-[3-(3-Carboxy-1-cyclopropyl-4-oxo-1.4-dihydro-quinolin-6-yl)-allyloxy]-propoxy}-propyl)-azithromycin;

4"-O-(3-{3-[3-(3-Carboxy-1-cyclopropyl-4-oxo-1.4-dihydro-quinolin-6-yl)-propoxy]-propoxy}-propyl)-azithromycin;

4"-O-(3-{2-[3-(3-Carboxy-1-dimethylamino-4-oxo-1,4-dihydro-quinolin-6-yl)-allyloxy]-ethoxy}-propyl)-azithromycin;

4"-O-(3-{2-[3-(3-Carboxy-1-dimethylamino-4-oxo-1,4-dihydro-quinolin-6-yl)-propoxy]-ethoxy}-propyl)-azithromycin;

4"-O-(2-{2-[2-(3-Carboxy-6-fluoro-1-cyclopropyl-4-oxo-1,4-dihydro-quinolin-7-ylamino)-ethoxy]-ethylamino}-ethyl)-azithromycin 11,12-cyclic carbonate;

4"-O-(2-{2-[2-(3-Carboxy-6-fluoro-1-cyclopropyl-4-oxo-1,4-dihydro-quinolin-7-ylamino)-ethoxy]-ethylamino}-ethyl)-azithromycin;

4"-O-{2-({2-[(2-{[2-(3-Carboxy-1-ethyl-4-oxo-1,4-dihydro-6-quinolinyl)ethyl]oxy}ethyl)oxy]ethyl}amino)ethyl}-6-O-methyl-erythromycin A formate;

4"-O-{2-({2-[(2-{[2-(3-Carboxy-1-ethyl-4-oxo-1,4-dihydro-6-quinolinyl)ethyl]oxy}ethyl)oxy]ethyl}methylamino)ethyl}-6-O-methyl-erythromycin A;

4"-O-(2-{[2-({3-[3-Carboxy-1-(dimethylamino)-4-oxo-1,4-dihydro-6-quinolinyl]propyl}amino)ethyl]sulfonyl}ethyl)-6-O-methyl erythromycin A 11,12-carbonate;

4"-O-(3-{2-[3-(3-Carboxy-1-ethyl-4-oxo-1,4-dihydro-quinolin-6-yl)-allyloxy]-ethoxy}-propyl)-azithromycin;

4"-O-(3-{2-[3-(3-Carboxy-1-ethyl-4-oxo-1,4-dihydro-quinolin-6-yl)-propoxy]-ethoxy}-propyl)-azithromycin; and 4"-O-(3-{3-[2-(3-Carboxy-7-chloro-1-cyclopropyl-4-oxo-1,4-dihydro-quinolin-6-ylamino)-ethoxy]-propionylamino}-propyl)-6-O-methyl erythromycin A 11,12-cyclic carbamate;

or a pharmaceutically acceptable salt thereof.

12. A process for the preparation of a compound as claimed in claim 1, which comprises:

a) reacting a compound of formula (II)

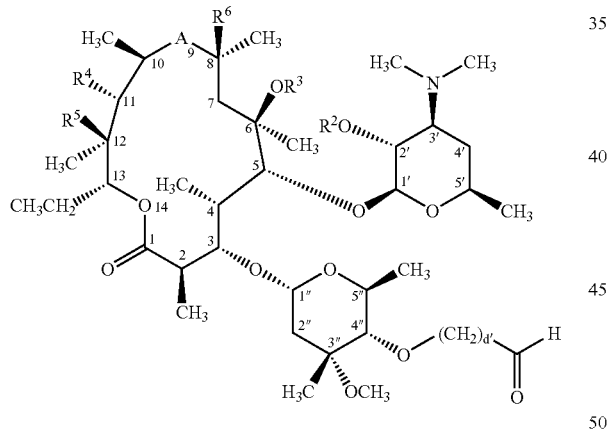

with a suitable amine (IIIa), (IIIb), (IIIc), or (IIId), (IIIa) HN(R$^{30}$)(CH$_2$)$_v$B$^a$(CH$_2$)$_v$D$^a$-R$^{11a}$, (IIIb) HN(R$^{30}$)(CH$_2$)$_v$B$^a$—R$^{33}$—R$^{11a}$, (IIIc) HN(R$^{30}$)(CH$_2$)$_r$B$^a$(CH$_2$)$_r$D$^a$(CH$_2$)$_r$E$^a$-R$^{11a}$, (IIId) HN(R$^{30}$)(CH$_2$)$_v$B$^a$(CH$_2$)$_v$D$^a$-R$^{33}$—R$^{11a}$ wherein B$^a$, D$^a$, E$^a$, R$^{33}$, R$^{11a}$ and v are as defined in claim 1 or are independently groups convertible to B, D, E and R$^{11}$ giving the compound of claim 1, wherein U is the divalent radical —N(R$^{30}$)—; or b) reacting a compound of formula (V), wherein L is a leaving group

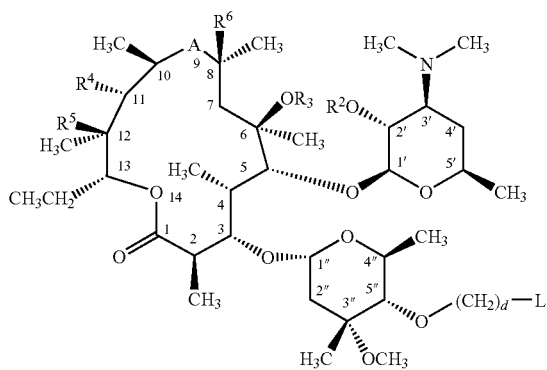

with a compound of formula X$^a$R$^{11a}$ (VI), wherein X$^a$ and R$^{11a}$ are as defined in claim 1 or a group convertible to R$^{11}$ and X giving the compound of claim 1, wherein U is a group selected from —N(R$^{30}$)—, —O— and —S—, and d is an integer from 2 to 6; or c) reacting a compound of formula (VII),

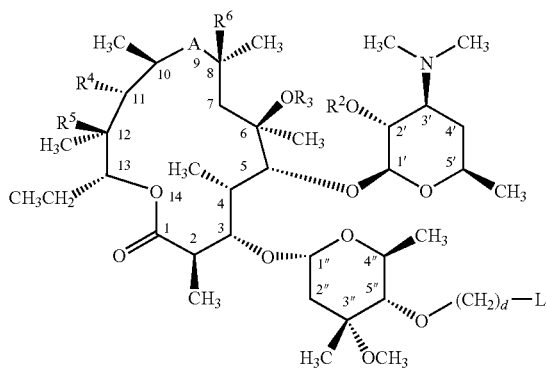

wherein d is 2 and L is selected from —NH$_2$, —CH$_2$OH, —CHO and —COOH with a compound of Formula X$^a$R$^{11a}$(VI), wherein R$^{11a}$ is R$^{11}$ as defined in claim 1 or a group convertible to R$^{11}$ and X, giving the compound of claim 1 wherein U is a group selected from —N(R$^{30}$)—, —O—, —N(R$^{30}$)C(O)— and —C(O)N(R$^{30}$)—, and d is 2; or d) reacting a protected compound of Formula (IX)

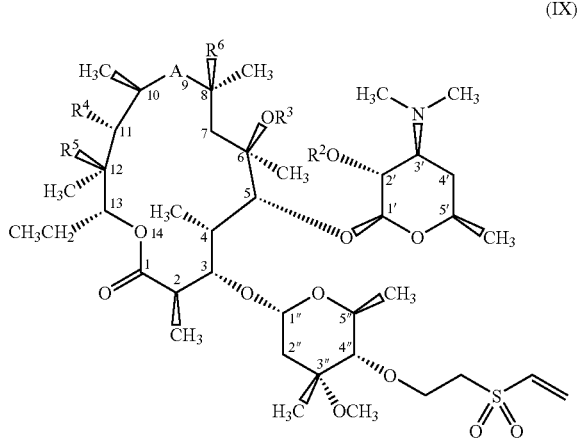

with an amine (IIIe), (IIIf), (IIIg), or (IIIh),
(IIIe) $HN(R^{30})(CH_2)_vD^a$-$R^{11a}$,
(IIIf) $HN(R^{30})(CH_2)_vR^{33}$—$R^{11a}$,
(IIIg) $HN(R^{30})(CH_2)_vD^a(CH_2)_vE^a$-$R^{11a}$, or
(IIIh) $HN(R^{30})(CH_2)_vD^a$-$R^{33}$—$R^{11a}$
wherein $D^a$, $E^a$, $R^{33}$, $R^{11a}$ and v are as defined claim 1 or are independently groups convertible to D, E and $R^{11}$ giving compound of claim 1, wherein X—$R^{11a}$ is —$SO_2(CH_2)_2$ $N(R^{30})(CH_2)_vD^a$-$R^{11a}$, —$SO_2(CH_2)_2N(R^{30})(CH_2)_v$ $R^{33}$—$R^{11a}$,
—$SO_2(CH_2)_2N(R^{30})(CH_2)_vD^a(CH_2)_vE^a$-$R^{11a}$, or —$SO_2$ $(CH_2)_2N(R^{30})(CH_2)_vD^a$-$R^{33}$—$R^{11a}$ and d is 2;

e) oxidizing a compound of formula (I) wherein U or B is —$S(O_z)$— and z is 0, giving a compound of claim 1 wherein U or B is —$S(O_z)$— and z is 1 or 2 or f) reductive alkylation of a compound of formula (I) wherein U, B, D, or E is —$N(R^{30})$— and $R^{30}$ is hydrogen, giving a compound of claim 1 wherein U, B, D, or E is —$N(R^{30})$— and $R^{30}$ is $C_{1-4}$alkyl; and thereafter, optionally converting the resultant compound of formula (I) into a pharmaceutically acceptable salt thereof.

13. A method for the treatment of a bacterial infection in the human or non-human animal body comprising administration to a body in need of such treatment of an effective amount of a compound as claimed claim 1, or a pharmaceutically acceptable salt thereof.

14. The method of claim 13, wherein the body is a human body.

15. The method of claim 13, wherein the bacterial infection is due to *Staphylococcus aureus*, *Streptococcus pneumoniae*, *Streptococcus pyogenes*, *Enterococcusfaecalis*, *Haemophylus influenzae*, or *Moraxella catarrhalis*.

16. The method of claim 15, wherein the bacterial infection is due to *Streptococcus pneumoniae*, or *Streptococcus pyogenes*.

17. The method of claim 15, wherein the bacteria is resistant to erythromycin.

18. A pharmaceutical composition comprising the compound of claim 1, or a pharmaceutically acceptable salt thereof and a pharmaceutically acceptable excipient, diluent and/or carrier.

* * * * *